(12) United States Patent
Takayama et al.

(10) Patent No.: US 12,250,957 B2
(45) Date of Patent: Mar. 18, 2025

(54) METHOD FOR PRODUCING FERMENTED LIQUID COMPRISING SHORT-CHAIN FATTY ACID

(71) Applicant: HIGHER MOUNT CO., LTD., Gifu (JP)

(72) Inventors: Hirotaka Takayama, Gifu (JP); Emi Takayama, Gifu (JP)

(73) Assignee: HIGHER MOUNT CO., LTD., Gifu (JP)

(*) Notice: Subject to any disclaimer, the term of this patent is extended or adjusted under 35 U.S.C. 154(b) by 465 days.

(21) Appl. No.: 17/629,469

(22) PCT Filed: Jul. 22, 2020

(86) PCT No.: PCT/JP2020/028427
§ 371 (c)(1),
(2) Date: Jan. 24, 2022

(87) PCT Pub. No.: WO2021/020271
PCT Pub. Date: Feb. 4, 2021

(65) Prior Publication Data
US 2022/0248718 A1    Aug. 11, 2022

(30) Foreign Application Priority Data
Jul. 26, 2019   (JP) .................. 2019-137719

(51) Int. Cl.
*A23L 2/38*       (2021.01)
*A23L 11/50*      (2021.01)
(Continued)

(52) U.S. Cl.
CPC .............. *A23L 2/382* (2013.01); *A23L 11/50* (2021.01); *A23L 33/105* (2016.08); *A23L 33/12* (2016.08); *A23V 2002/00* (2013.01)

(58) Field of Classification Search
CPC ........ A23L 2/382; A23L 11/50; A23L 33/105; A23L 33/12; A23L 33/135; A23L 29/065; A23L 33/10; C12P 7/52
See application file for complete search history.

(56) References Cited

FOREIGN PATENT DOCUMENTS

CN    106615672 A  *  5/2017
CN    108402453 A     8/2018
(Continued)

OTHER PUBLICATIONS

CN 106615672 A (clarivate Machine translation) (Year: 2016).*
(Continued)

*Primary Examiner* — Elizabeth Gwartney
*Assistant Examiner* — Andrew E Merriam
(74) *Attorney, Agent, or Firm* — Oliff PLC

(57) ABSTRACT

A method for producing a fermented liquid having an acidity of pH 3 to 4, including colloidal particles having a particle size not exceeding 50 nm and short-chain fatty acids. The method includes providing fermentation apparatus including a plurality set of temperature-controlled fermentation containers at each stage of the multi-stage fermentation process; using a soft water as a starter, a seed bacterial liquid comprising seven species of fermentation bacteria (International Accession No. NITE BP-02945 to NITE BP-02951) including spore-forming *Clostridium* bacteria, controlled under a low temperature condition, and three kinds of fermented media derived from natural materials, produced by individually fermenting respective first medium of dried soybeans, second medium of mixed medium of dried plants consisting Taiso, Kukoshi, and Ukon, and third material of honey material; and producing the fermented liquid by multi-stage fermentation process.

7 Claims, 24 Drawing Sheets

| Taxonomical position | Bacteria form | Gram's stain | Spore-forming | Color of colony | International Accession No. |
|---|---|---|---|---|---|
| Aneurinibacillus sp. | Bacillus | Positive | Negative | Cream color | NITE BP-02945 |
| Brevibacillus sp. | Bacillus | Negative | Negative | Cream color | NITE BP-02946 |
| Pseudoclavibacter sp. | Bacillus | Positive | Negative | Cream color | NITE BP-02947 |
| Paenibacillus sp. | Bacillus | Negative | Positive | Cream color | NITE BP-02948 |
| Clostridium sp. | Bacillus | Positive | Positive | Cream color | NITE BP-02949 |
| Clostridium sp. | Bacillus | Positive | Positive | Cream color | NITE BP-02950 |
| Clostridium sp. | Bacillus | Positive | Positive | Cream color | NITE BP-02951 |

(51) Int. Cl.
   *A23L 33/105* (2016.01)
   *A23L 33/12* (2016.01)

(56) References Cited

FOREIGN PATENT DOCUMENTS

| JP | H05-304889 A | 11/1993 |
| JP | 2001-120180 A | 5/2001 |
| JP | 2005-218390 A | 8/2005 |
| JP | 2008-273895 A | 11/2008 |
| JP | 2009-178084 A | 8/2009 |
| JP | 4540376 B2 | 9/2010 |
| JP | 2010-540623 A | 12/2010 |
| JP | 2011-167190 A | 9/2011 |
| JP | 2013-524791 A | 6/2013 |
| JP | 2013-132290 A | 7/2013 |
| JP | 2014-168441 A | 9/2014 |
| JP | 2016-000039 A | 1/2016 |

OTHER PUBLICATIONS

MIRAI undiluted solution | Product Information Products | Toyama Sky Co., Ltd. Natural & Beauty, downloaded on May 2, 2024 from https://web.archive.org/web/20161024065043/http://toyama-sky.co.jp/products/mirai/00866-2/ (Year: 2016).*

Sep. 24, 2020 International Search Report issued in International Patent Application No. PCT/JP2020/028427.

Sep. 24, 2020 Written Opinion issued in International Application No. PCT/JP2020/028427.

Feb. 1, 2022 International Preliminary Report on Patentability issued in International Application PCT/JP2020/028427.

* cited by examiner

FIG. 5
A
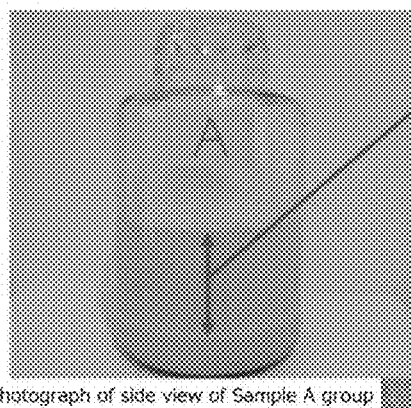
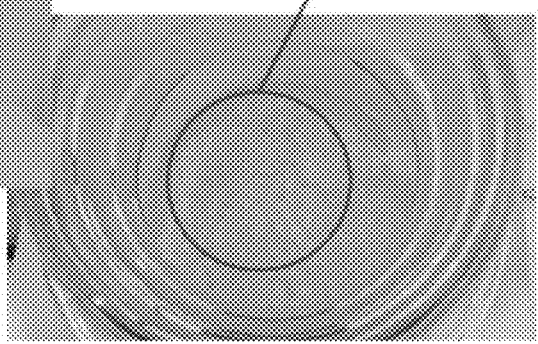
B
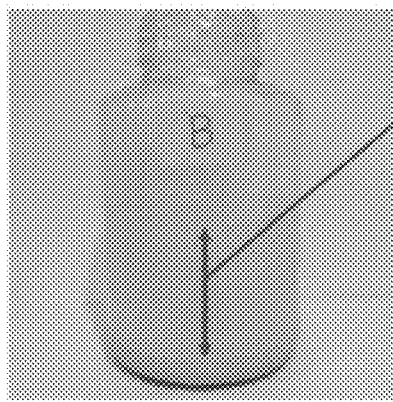
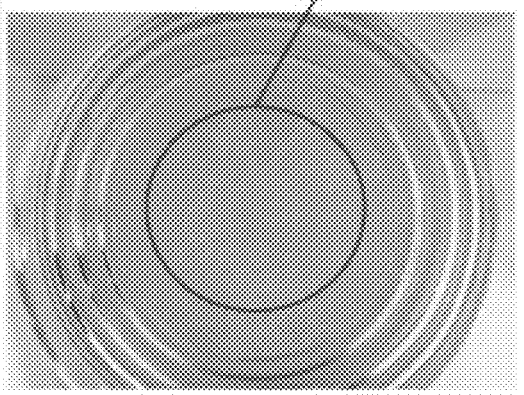

FIG. 6

| Taxonomical position | Bacteria form | Gram's stain | Spore-forming | Color of colony | International Accession No. |
|---|---|---|---|---|---|
| Aneurinibacillus sp. | Bacillus | Positive | Negative | Cream color | NITE BP-02945 |
| Brevibacillus sp. | Bacillus | Negative | Negative | Cream color | NITE BP-02946 |
| Pseudoclavibacter sp. | Bacillus | Positive | Negative | Cream color | NITE BP-02947 |
| Paenibacillus sp. | Bacillus | Negative | Positive | Cream color | NITE BP-02948 |
| Clostridium sp. | Bacillus | Positive | Positive | Cream color | NITE BP-02949 |
| Clostridium sp. | Bacillus | Positive | Positive | Cream color | NITE BP-02950 |
| Clostridium sp. | Bacillus | Positive | Positive | Cream color | NITE BP-02951 |

FIG. 7
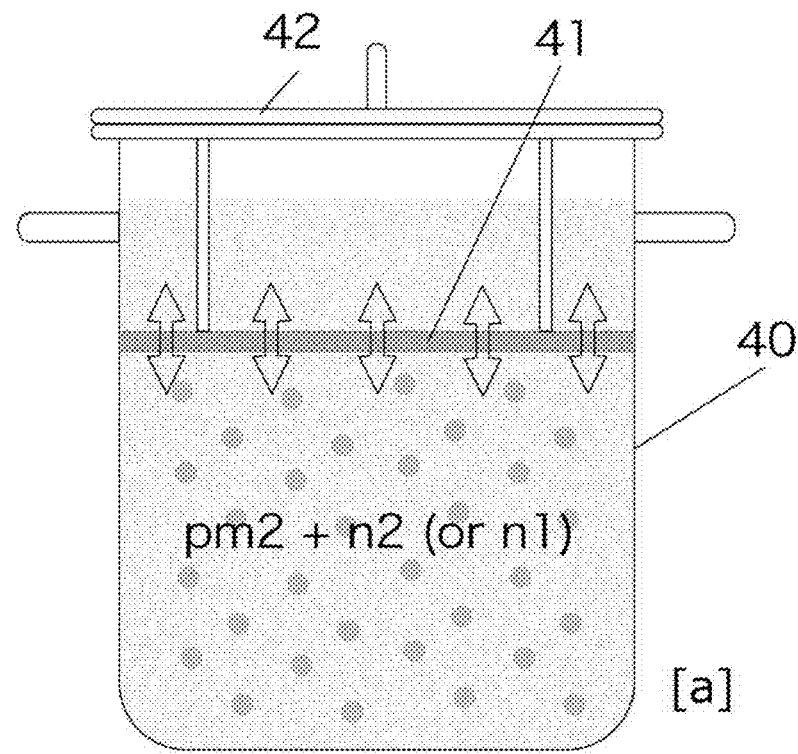
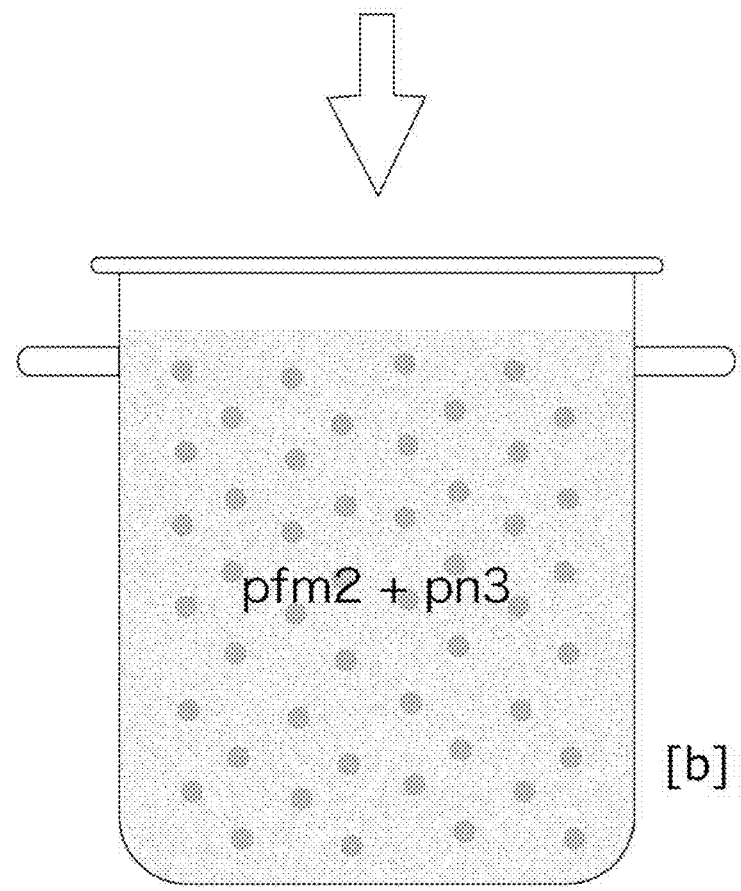

FIG. 8
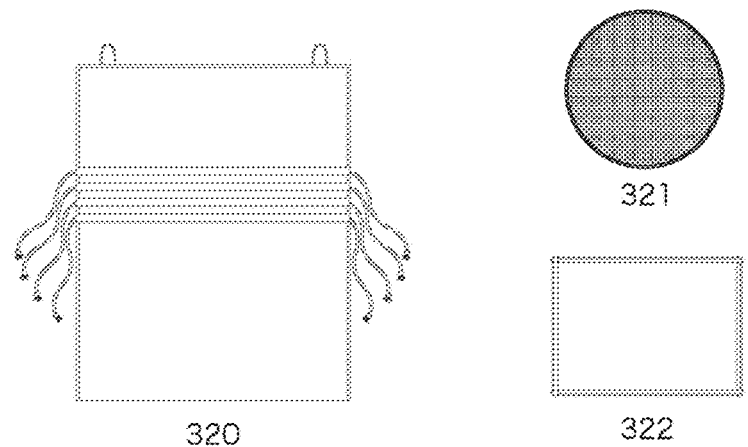
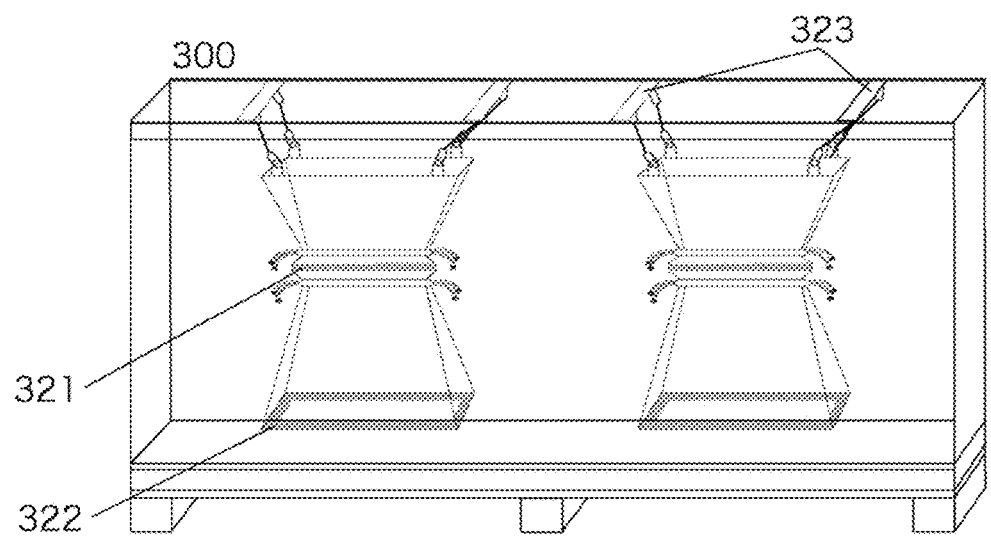
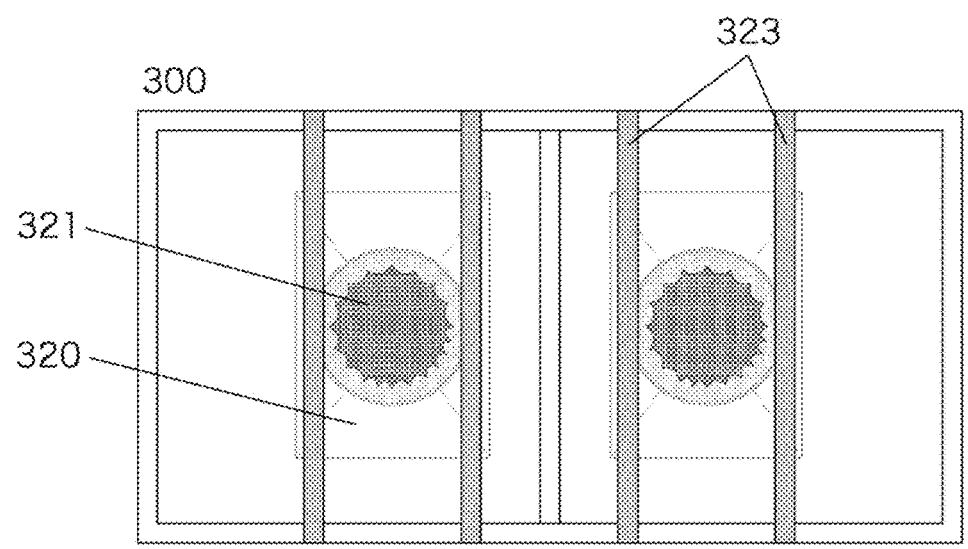

FIG. 10
A
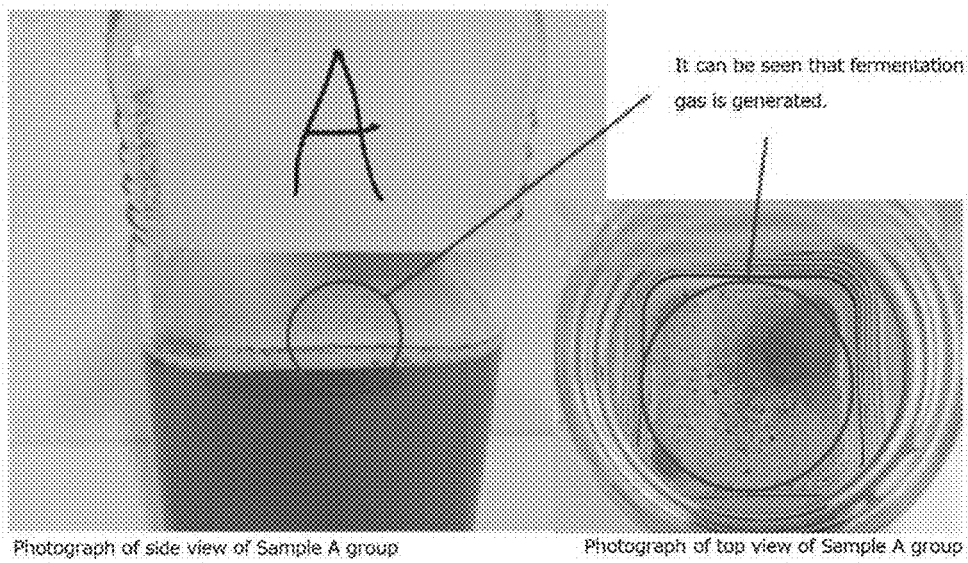
B
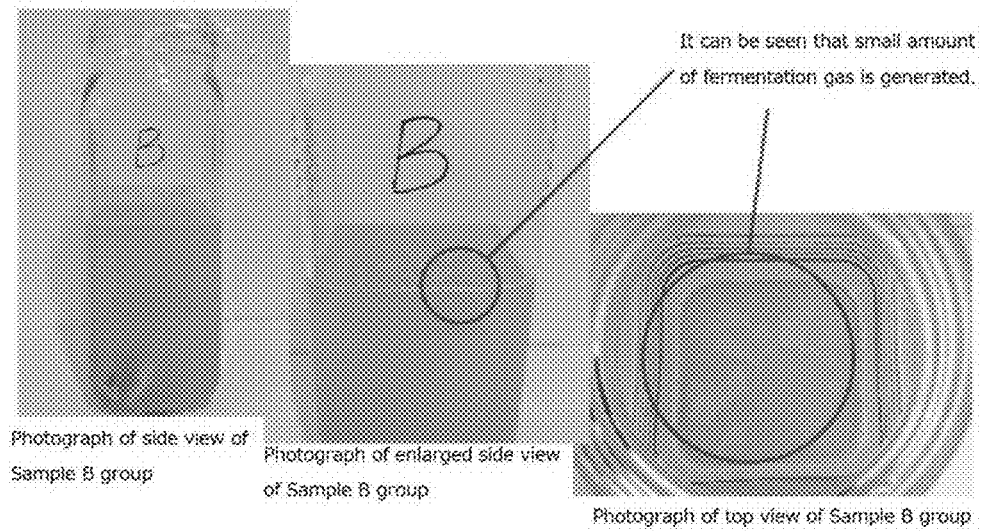

FIG. 13
A
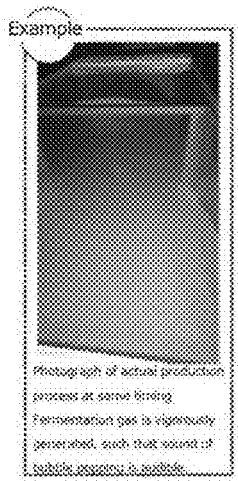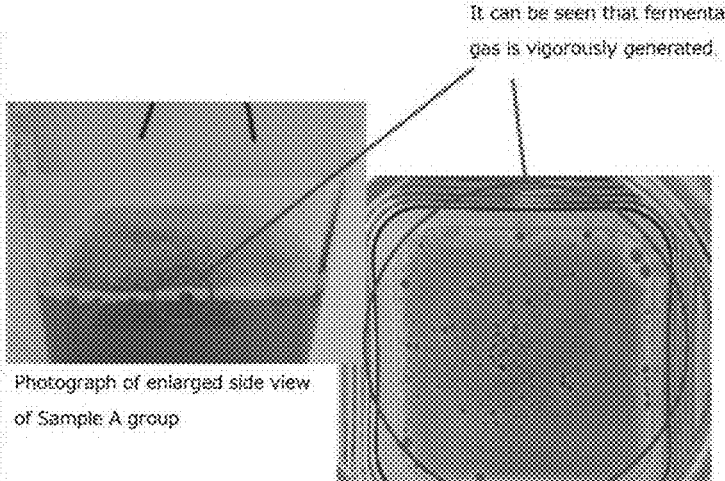
B
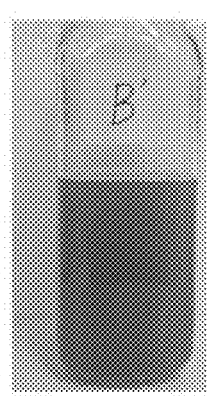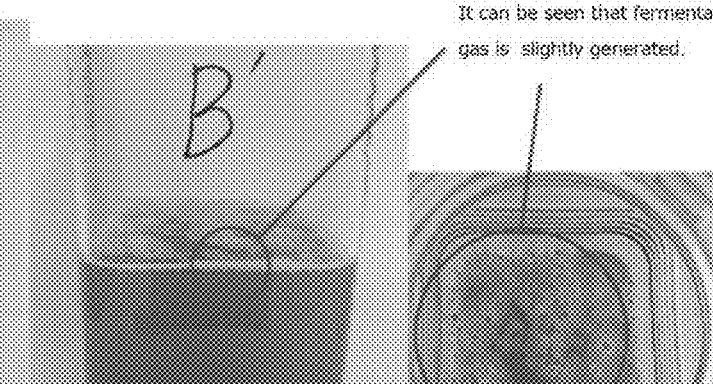

FIG. 19

RESULT OF SUGAR ANALYTICAL TEST

| ITEM OF ANALYTICAL TEST | | RESULT | LOWER LIMIT OF QUANTIFICATION | NOTE | METHOD |
|---|---|---|---|---|---|
| n4 (SAMPLE AT THE END OF THE FOURTH FERMENTATION) 3.93 g/100g [mL] | SUGAR | 3.93 g/100g | ***** | 1 | SOMOGYI MODIFIED METHOD |
| n5 (SAMPLE AT THE BEGINNING OF THE SIXTH FERMENTATION) 2.88 g/100g [mL] | SUGAR | 2.88 g/100g | ***** | 1 | SOMOGYI MODIFIED METHOD |
| n6 (SAMPLE AT THE END OF THE SIXTH FERMENTATION) 1.19 g/100g [mL] | SUGAR | 1.19 g/100g | ***** | 1 | SOMOGYI MODIFIED METHOD |

NOTE 1. CONVERTED TO GLUCOSE. HYDROLYSIS CONDITION: 2.3% HYDROCHLORIC ACID, 65°C, 15 MINUTES

FIG. 20
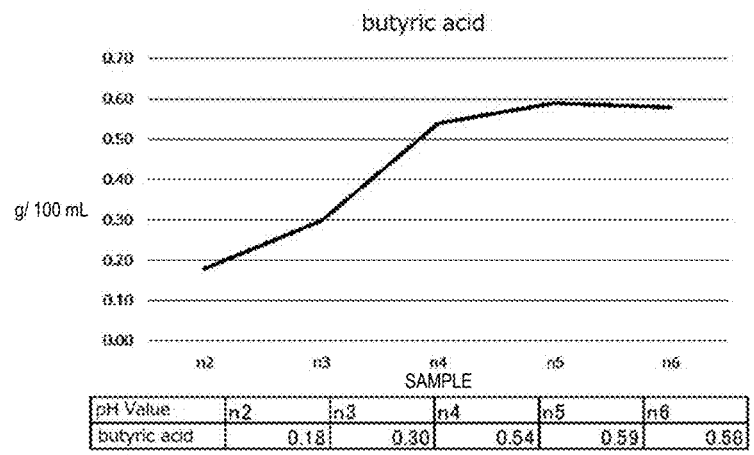
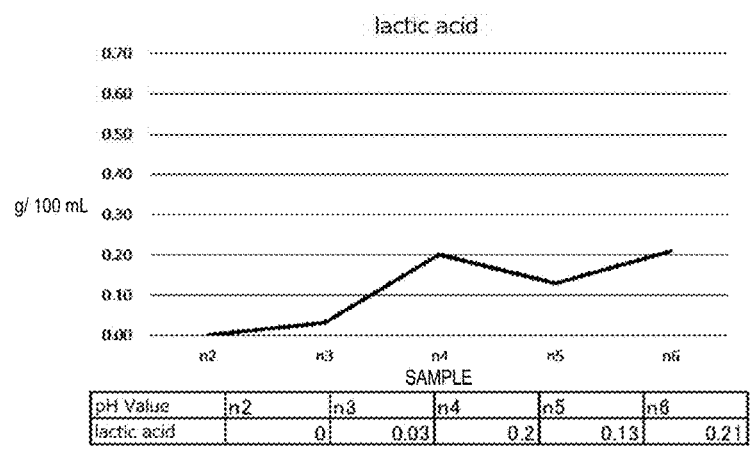
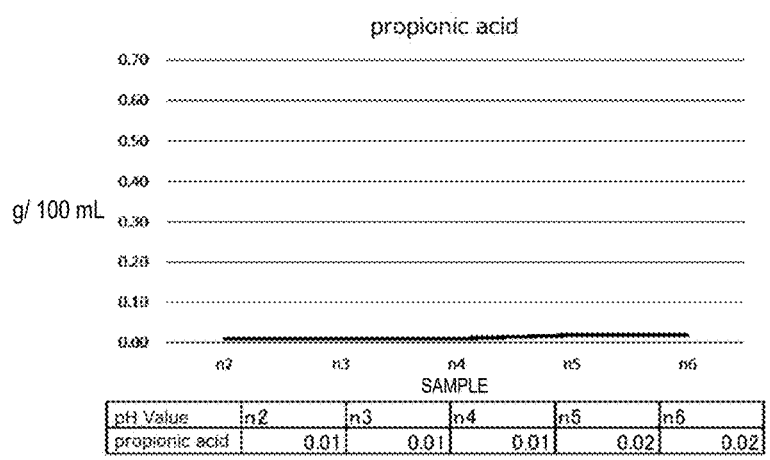

FIG. 21
Table 1. Calcium increment amount
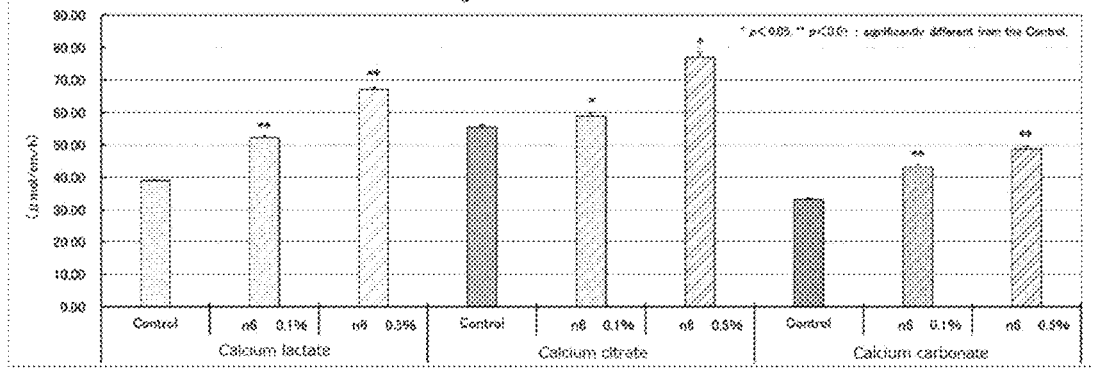
Table 2. Calcium absorption rate
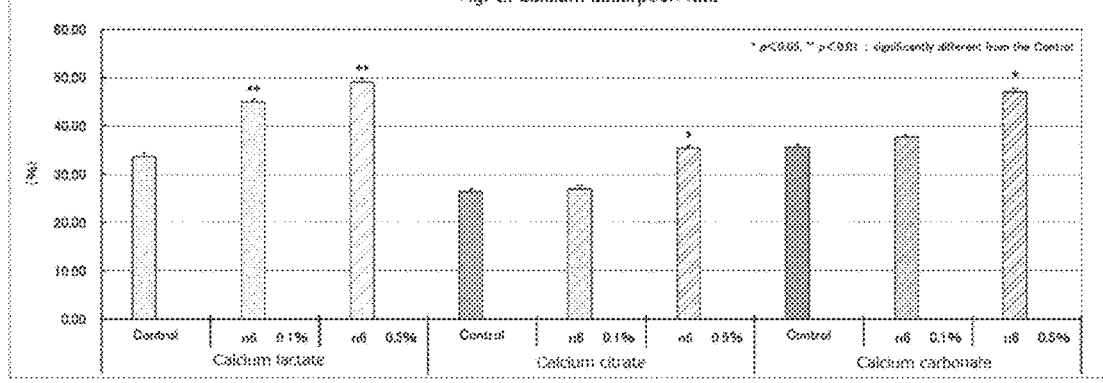

Inhibition of Krt6b gene expression in tumor tissue of n6-administered mice (Lewis Lung carcinoma-syngraft model)
(Real-time RT-PCR)

METHOD FOR PRODUCING FERMENTED LIQUID COMPRISING SHORT-CHAIN FATTY ACID

TECHNICAL FIELD

The present invention relates to a method for producing a fermented liquid comprising short-chain fatty acids by fermenting natural materials. The fermented liquid produced according to the present invention is a fermented liquid having an acidity of pH 3 to 4, comprising colloidal particles having a particle size not exceeding 50 nm and short-chain fatty acids, the short-chain fatty acids comprising butyric acid, propionic acid and lactic acid. The content of the colloidal particles in the fermented liquid is 6.5 to 7.5%. The fermented liquid comprises 0.5 to 0.6 g of the butyric acid per 100 mL of the fermented liquid.

BACKGROUND ART

Numerous fermented food products, such as, for example, vinegars, miso (fermented soybean pastes), soy sauces, and fermented alcoholic beverages are commercially available as daily foodstuffs. Also, many liquid fermented food products are commercially available as functional foods or raw material liquid for functional foods. Traditionally, liquid fermented extracts have been produced by grinding row materials including fruits, vegetables, legumes such as soybeans, and nuts such as chestnuts and walnuts, putting the ground row materials into natural water, and fermenting them by selected fermentation bacteria. Such method and processed foods manufactured by the method have been well known and variously modified from prehistoric age.

For the short-chain fatty acids such as butyric acid, propionic acid, and lactic acid according to the present invention, Non-Patent Literature 1, for example, describes that a short-chain fatty acid produced during anaerobic fermentation of dietary fiber by intestinal bacteria is a butyric acid, and from investigations on effect of the butyric acid, it is confirmed that the butyric acid facilitates only generation of regulatory T-cells. The Non-Patent Literature 1 reports that "when chronic pancreatitis model mice are fed with butyrated starch feed, generation of regulatory T-cells from transfusion cells are facilitated in colon, and improvement of symptoms of enteritis is appreciated."

Furthermore, Non-Patent Literature 2 reports that two kinds of regulatory T-cells (Treg), i.e., thyms-derived Treg (tTreg) and peripherally derived Treg (pTreg) are identified, wherein the pTreg relates RORyt, which is a master transcription factor of Th 17 lymphocytes, and in derivation of the pTreg, butyric acid produced by *Clostridium* Clusters IV and XIVa is involved, and thus, short-chain fatty acids, especially butyric acid is important for derivation of the pTreg in the colon.

Furthermore, Non-Patent Literature 3 reports that "It becomes apparent from recent study that short-chain fatty acids are utilized as an energy source for a host, as well as play an indispensable role in maintaining an energy homeostasis of the host, such as inhibition of body weight gain, ingestion, improvement of glucose metabolism, and insulin sensitivity enhancement" and points out that importance of ingesting dietary fibers including resistant polysaccharide, which is a source of short-chain fatty acids. The Non-Patent Literature 3 introduces various molecular mechanism of short-chain fatty acids, especially butyric acid, via fatty acid receptor GRP41, GRP43, GRP109a, and Olfr78 in detail.

Non-Patent Literature 4 reports that mixed culture of *Shigella* and butyric acid bacteria (*Clostridium butyricum* MIYAIRI 588 strain) was performed, and inhibition of growth of *Shigella* was observed even at small number of bacteria. The Non-Patent Literature 4 reports that recently, especially an effect of butyric acid or butyric acid bacteria for inhibiting inflammation in vivo attracts attention.

Non-Patent Literature 5 reports that butyric acid, a kind of short-chain fatty acids produced by intestinal bacterial flora normally present in colon, is an essential nutrient for colon, and consumed in epithelial cells as an energy, and also butyric acid metabolism disorder is a cause of ulcerative colitis. The Non-Patent Literature 5 also presents as physiological effects of short-chain fatty acid, such as enhancement of absorption of minerals such as calcium, inhibition of cholesterol synthesis, and inhibition of onset of colon cancer by butyric acid, and analytical result thereof.

For a conventional method for producing the fermented liquid, for example, Patent Literature 1 describes a fermented product and a method for manufacturing thereof in which raw materials of ground natural products such as legumes and nuts are put into a lactose solution, at least two fermenters and a propagating container are used, and fresh microorganisms and fermented extracts are uniformly mixed to produce the fermented product having immune activity. For a method for producing the acidic materials, Patent Literature 2 describes a multi-stage fermentation including nanofiltration, and Patent Literature 3 describes a method for manufacturing a fermented liquid in which *Bacillus subtilis* var. natto is added to leaves of Ashitaba (*Angelica keiskei*) and soybeans powder, and the fermented liquid is produced in a multi-stage fermentation.

Patent Literature 4 describes a method for producing a liquid of lactic acid bacteria-produced materials, in which sixteen species of lactic acid bacteria are used, the species are grouped into a plurality of groups, each group is passaged with maintaining its symbiotic condition to produce a culture solution of the lactic acid bacteria, and the culture solution is filtered. The Patent Literature 4 further describes that the filtered culture solution of the lactic acid bacteria have an effect for activate intestinal good bacteria.

For promoting calcium metabolism on living body, Patent Literature 5 describes a physiologically active agent having a calcium absorption-promoting activity and an antioxidant activity, comprising a peptide or peptide mixture obtained by decomposing casein with a lactic acid bacteria-produced proteinase. Patent Literature 6 describes a health supplement food for drinks having a calcium absorption-promoting activity, which is a fermented soybeans polymer containing folic acid, obtained by putting soybeans into purified water and fermenting them.

For fermented foods using soybeans as a raw material, Patent Literatures 7 to 9 disclose fermented foods produced by a method in which soybeans are used as a raw material and *Bifidobacterium* or lactic acid bacterium strains are used as a starter.

For an acidity of fermented liquids to be produced, Patent Literature 10 describes a method for manufacturing a fermented soymilk drink, in which an acidity of the fermented soymilk drink is controlled to be lower than pH 4.5, as well as a fermented soymilk drink having an acidity lower than pH 4.5 and a viscosity of 5.9 mPa·s or higher. Patent Literature 11 describes an enzyme-containing health food having an acidity of approximately pH 3.7 to 3.9, as well as a method for manufacturing the health food by adding several fermented liquids etc. to herb extracts and fermenting them.

CITATION LIST

Non-Patent Literatures

[Non-Patent Literature 1] "Enteric bacteria metabolic products controlling generation of regulatory T-cells", Morisada HAYAKAWA, Farumashia, vol. 50, No. 8, p. 815 (2014)

[Non-Patent Literature 2] "Allergic diseases and gut microbiota", Noriaki SHIMOJO, Experimental Medicine (Supplement) Vol. 37, No. 2, p. 97-103 (2019)

[Non-Patent Literature 3] "Host metabolic regulation and gut microbiota", Ikuo KIMURA, Experimental Medicine (Supplement) Vol. 37, No. 2, p. 119-126 (2019)

[Non-Patent Literature 4] "Inhibition of Enteropathogens by *Clostridium butyricum* MIYAIRI 588", Toyoaki KROIWA, Kazumine KOBARI, and Masaaki IWANAGA, The Journal of the Japanese Association for Infectious Diseases, vol. 64, No. 3, p. 257-263 (1990)

[Non-Patent Literature 5] "Physiological Effects of Short-Chain Fatty Acid Produced from Prebiotics in the Colon", Hiroshi HARA, Journal of intestinal microbiology, Vol. 16, p 35-42 (2002)

PATENT LITERATURES

[Patent Literature 1] PCT Japanese Publication: JP2013-524791A

[Patent Literature 2] Laid-Open Japanese Patent Application Publication: JP2016-000039A

[Patent Literature 3] Laid-Open Japanese Patent Application Publication: JP2013-132290A

[Patent Literature 4] Japanese Patent Number 4540376B

[Patent Literature 5] Laid-Open Japanese Patent Application Publication: JPH05-304889A

[Patent Literature 6] PCT Japanese Publication: JP2010-540623A

[Patent Literature 7] Laid-Open Japanese Patent Application Publication: JP2001-120180A

[Patent Literature 8] Laid-Open Japanese Patent Application Publication: JP2005-218390A

[Patent Literature 9] Laid-Open Japanese Patent Application Publication: JP2011-167190A

[Patent Literature 10] Laid-Open Japanese Patent Application Publication: JP2014-168441A

[Patent Literature 11] Laid-Open Japanese Patent Application Publication: JP2009-178084A

SUMMARY OF INVENTION

Technical Problem

The present invention provides a method for producing a fermented liquid comprising short-chain fatty acids by fermenting natural materials. More particularly, the present invention provides a method for producing a fermented liquid having an acidity of pH 3 to 4 comprising colloidal particles having a particle size not exceeding 50 nm and short-chain fatty acids.

The fermented liquid produced according to the present invention is a fermented liquid having an acidity of pH 3 to 4, comprising colloidal particles having a particle size not exceeding 50 nm and a shot-chain fatty acid, the short-chain fatty acids comprising butyric acid, propionic acid and lactic acid. The fermented liquid may contain the colloidal particles at a content of 6.5 to 7.5%. The fermented liquid may contain 0.5 to 0.6 g of the butyric acid per 100 mL of the fermented liquid.

The fermented liquid may be used as a functional food, and it is confirmed that the fermented liquid acts to double *Lactobacillus* and *Bifidobacterium* facilitating intestinal regulation, while acts to halve *Clostridium perfringens* (*Welch bacillus*) detrimental to intestinal regulation, and that the fermented liquid increases calcium absorption ratio in a living body to facilitate its calcium metabolism and exert a significant effect on a bone mineral density and bone strength in the living body. It may be also considered that such effects corresponds with the above-mentioned various molecular mechanisms of short-chain fatty acids, especially butyric acid, via fatty acid receptors GPR41, GPR43, GPR109a and Olfr78, introduced in detail in the Non-Patent Literature 3.

The present invention provides a method, achieved by the inventor's steady practical work for many years, for producing a fermented liquid having an acidity of pH 3 to 4 comprising colloidal particles having a particle size not exceeding 50 nm and short-chain fatty acids, the short chain fatty acid comprising butyric acid, propionic acid and lactic acid, by fermenting natural materials.

More particularly, the present invention also provides a method for producing a fermented liquid having an acidity of pH 3 to 4 comprising colloidal particles having a particle size not exceeding 50 nm and short-chain fatty acids, the short chain fatty acid comprising butyric acid, propionic acid and lactic acid, by a multi-stage fermentation process in which seed bacteria symbiotically act, the seed bacteria being preliminarily allowed to be in a symbiotic and stable state controlled under a low temperature condition, wherein the seed bacteria comprises spore-forming *Clostridium* bacteria producing organic acids including short-chain fatty acids (seven species of fermentation bacteria deposited to National Institute of Technology and Evaluation, Patent Microorganisms Depositary (NPMD), which is an international depositary authority under the terms of the Budapest Treaty, under International Accession Numbers NITE BP-02945, NITE BP-02946, NITE BP-02947, NITE BP-02948, NITE BP-02949, NITE BP-02950, and NITE BP-02951).

The method of the present invention is characterized in that:

providing fermentation apparatus including a plurality set of temperature-controlled fermentation containers at each stage of multi-stage fermentation process, using:
- a soft water w as a starter,
- a seed bacterial liquid b comprising seven species of fermentation bacteria (International Accession No. NITE BP-02945 to NITE BP-02951) including spore-forming *Clostridium* bacteria controlled under a low temperature condition, and
- three kinds of fermented media m1, m2, and m3 derived from natural materials, produced by individually fermenting respective first medium pm1 of dried soybeans, a second medium pm2 of mixed medium of dried plants consisting of Jujube (Taiso), *Lycium* fruit (Kukoshi), and Turmeric (Ukon), and a third medium pm3 of honey material, and producing a fermented liquid having an acidity of pH 3 to 4 comprising colloidal particles having a particle size not exceeding 50 nm and short-chain fatty acids, by multi-stage fermentation process.

The Non-Patent and Patent Literatures fails to disclose or suggest a fermented liquid having an acidity of pH 3 to 4 comprising colloidal particles having a particle size not exceeding 50 nm and short-chain fatty acids, the short-chain fatty acids comprising butyric acid, propionic acid and lactic acid. Furthermore, the Non-Patent and Patent Literatures fails to disclose or suggest a method for producing a fermented liquid having an acidity of pH 3 to 4 comprising colloidal particles having a particle size not exceeding 50 nm and short-chain fatty acids, the short-chain fatty acids comprising butyric acid, propionic acid and lactic acid, by multi-stage fermentation process. In addition, it is apparent that any combinations of technical elements described in the Non-Patent and Patent Literatures fail to suggest to those skilled in the art to achieve the method according to the present invention for producing a fermented liquid having an acidity of pH 3 to 4 comprising colloidal particles having a particle size not exceeding 50 nm and short-chain fatty acids, the short-chain fatty acids comprising butyric acid, propionic acid and lactic acid.

Solution to Problem

A first feature configuring a method according to an embodiment of the present invention for producing a fermented liquid having an acidity of pH 3 to 4 comprising colloidal particles having a particle size not exceeding 50 nm and short-chain fatty acids, is a first fermentation line f1 in a multi-stage fermentation process.

The first fermentation line f1 uses a first fermentation system s1 and a second fermentation system s2. The first fermentation system s1 comprises a plurality of (four or more) pottery fermentation bottles 10, a first medium tank 20 with a heating kettle 30, and two first fermentation tanks 100 shown in FIGS. 1 [1] to [5]. The second fermentation system s2 comprises one second fermentation tank 200 shown in FIGS. 1 [6] to [8], and a extraction unit 110 of the first fermentation tank 100, to be coupled to the second fermentation tank 200 shown in FIG. 4 [b].

The first fermentation line f1 are configured by a first process $p_1 1$ producing a first preliminary fermented liquid pn1 and fermented soybeans fs shown in FIG. 2 (2); a second process $p_1 2$ producing a first fermented liquid n1 having an acidity of pH 5.3± shown in FIG. 2 [b] to [d] and stage 1 in FIG. 16; and a third process $p_1 3$ producing a second fermented liquid n2 having an acidity of pH 5.0± shown in FIG. 1 and stage 1 in FIG. 16.

As used herein, a sign ± attached to pH values represents that yearly variation of pH values is within 0.3 between lots of each fermented liquid in a fermentation process shown in FIG. 16.

More particularly, entire process of the first fermentation line f1 is shown in FIGS. 1 [1] to [8]. The first fermentation line f1 comprises a first process $p_1 1$. In the first process $p_1 1$, as a starter, soft water having an acidity pH 7.3± and dried soybeans ds, which is a raw material of a first fermented medium m1, are put into each of the plurality of (four or more) pottery fermentation bottles 10 as shown in FIG. 2 (1), and a part of a seed bacterial liquid b and a sugar chain s are added for facilitating fermentation of the soybeans soaked and reconstituted in the soft water w, as shown in $pp_1 0$ in FIG. 2. The contents of the fermentation bottles 10 are fermented for 3 days (68 to 74 hours) with maintaining fermentation condition at 37° C. to 40° C. as shown in stage 1 in FIG. 16 to produce a first preliminary fermented liquid pn1 of pH 4.5± and fermented soybeans fs.

The first process $p_1 1$ of the first fermentation line f1 further comprises, as shown in FIGS. 1 [3] and [4] and $pp_1 1$ to $pp_1 3$ in FIG. 2:

a step of grinding the fermented soybeans fs by a grinding means (not shown) to produce soybean paste gfs, transferring the soybean paste gfs into a plurality (four or more) containers 11 shown in FIG. 2 (3), corresponding to each fermentation bottle 10, mixing the soybean paste gfs with the first preliminary fermented liquid pn1, and transferring them from each of the containers 11 to a heating kettle 30; and a first preliminary step of heating the soybean paste gfs and the first preliminary fermented liquid pn1 in the heating kettle 30 to 55° C. to 60° C., and transferring them into a first medium tank 20 preliminarily containing the soft water w for cooling, to produce a first fermented medium m1 of pH 4.5±, as shown in step $pp_1 4$ in FIG. 2 [a].

The first fermentation line f1 comprises a second process $p_1 2$ as shown in FIGS. 1 [5] and [6]. The second process $p_1 2$ as shown in FIG. 1 comprises:

a step of transferring the first fermented medium m1 into two first fermentation tanks 100 equally, and further putting a soft water w and a seed bacterial liquid b into each of the first fermentation tanks 100, as shown in FIG. 2 (4) and [b]; and a second preliminary step of stirring and mixing the first fermented medium m1, the soft water w, and the seed bacterial liquid b in each of the first fermentation tanks 100 to produce the second preliminary fermented liquid pn2 of pH 6.4±, as shown in step $pp_1 5$ in FIG. 2 [c].

The second preliminary fermented liquid pn2 produced in the second preliminary step is a turbid liquid pn2 in which the first fermented medium m1, the soft water w and the seed bacterial liquid b are mixed. After the second preliminary step of the first fermentation line f1, no soft water w and seed bacterial liquid b are newly added in the multi-stage fermentation process. Therefore, the turbid liquid pn2 becomes an original solution θ for producing a fermented liquid having an acidity of pH 3 to 4 and comprising colloidal particles having a particle size not exceeding 50 nm and short-chain fatty acids.

The second process $p_1 2$ further comprises a third preliminary step as shown in FIG. 1. As shown in step $pp_1 6$ in FIG. 2 [d], the third preliminary step produces a first fermented liquid n1 of pH 5.3± by fermenting the second preliminary fermented liquid of pH 6.4±, produced in each of the first fermentation tanks 100, for 50 to 100 days with maintaining fermentation condition at 37° C. to 40° C. as shown in stage 1 in FIG. 16.

In each first fermentation tank 100 shown in FIG. 1, a supernatant sponge layer sp containing fermentation gas is formed at a top layer, a first deposition layer dep1 containing fibrous materials from the first fermented medium m1 is deposited at a bottom layer, and the first fermented liquid n1 of pH 5.3± is formed between the sponge layer sp and the first deposition layer dep1, as shown in FIG. 4 [a] and described in details below.

The first fermentation line f1 may comprise a third process $P_1 3$ as shown in FIGS. 1 [7] and [8]. The third process $P_1 3$ comprises the steps of:

extracting only the first fermented liquid n1 of pH 5.3± produced in the second process $p_1 2$ from two first fermentation tanks 100 by an extraction unit 110 of the first fermentation tanks 100 as shown FIG. 4 [b], transferring the first fermented liquid n1 into one second fermentation tank 200, in which a fermentation environment without using any fermented medium is established, and stirring and mixing the first fermented liquid n1, and fermenting the first fermented liquid n1 by fermentation bacteria b1 in the seed bacterial liquid b contained in the first fermented liquid n1 for 3 to 5 days with maintaining fermentation condition at 37° C. to 40° C., as shown in stage 1 in FIG. 16 to produce a second fermented liquid n2 of pH 5.0±.

A second feature configuring a method according to an embodiment of the present invention for producing a fermented liquid having an acidity of pH 3 to 4 comprising colloidal particles having a particle size not exceeding 50 nm and short-chain fatty acids, is a second fermentation line f2 in the multi-stage fermentation process.

The second fermentation line f2 uses a third fermentation system s3. As shown in FIGS. 1 [9] to [12] and FIG. 7, the third fermentation system s3 comprises:

a second medium tank 40 shown in FIG. 1 or FIG. 7 [a];

one third fermentation tank 300, provided with a bag-shaped medium filter 320 to be suspended inside of the third fermentation tank 300 and a circulating pump unit 330; and an extraction unit 210 of the second fermentation tank 200, to be coupled to the third fermentation tank 300 shown in FIG. 1 (the principle of operation of the extraction unit 210 is same as that of the extraction unit 110 of FIG. 4 [b], and not shown).

The second fermentation line f2 is configured by a first process $p_2 1$ for producing a second fermented medium m2 of pH 4.8±; and a second process $p_2 2$ for producing a third fermented liquid n3 of pH 4.5±.

Entire process of the second fermentation line f2 is shown in FIGS. 1 [9] to [12]. The first process $p_2 1$ for producing a second fermented medium m2 of pH 4.8± is shown in FIGS. 1 [9] and [10], and more particularly, comprises a first preliminary process $pp_2 1$ and a second preliminary process $pp_2 2$ as follows.

The first preliminary process $pp_2 1$ comprises the steps of:
into the second medium tank 40 as shown in FIG. 1 or FIG. 7 [a], putting a part of either the second fermented liquid n2 of pH 5.0± or the first fermented liquid n1 of pH 5.3± as a starter, and a mixed medium pm2 of sterilized dried plants consisting of Jujube (Taiso), *Lycium* fruit (Kukoshi), and Turmeric (Ukon);

soaking, mixing, and stirring the sterilized mixed medium pm2 in the part of either the second fermented liquid n2 or the first fermented liquid n1, and fermenting them for two or three days with maintaining a fermentation condition at 37° C. to 40° C. as shown in stage 2 in FIG. 16, to produce a preliminary fermented mixed medium pfm2 and a third preliminary fermented liquid pn3 as shown in FIG. 1 or FIG. 7 [b].

In the first preliminary process $pp_2 1$, the mixed medium pm2 preferably comprises the Jujube, *Lycium* fruit, and Turmeric in a weight ratio of 7 to 4 to 1. For example, 200 to 210 g of the dried Jujube, 110 to 120 g of the dried *Lycium* fruit, and 25 to 30 g of the dried Turmeric are used in the mixed medium pm2 per total amount of 35 L of either the second fermented liquid n2 or the first fermented liquid n1.

In the second preliminary process $pp_2 2$, the preliminary fermented mixed medium pfm2 are removed from the second medium tank 40 shown in FIG. 1 or FIG. 7 [b], and ground by a grinding means (not shown) to the extent that seeds of the Jujube are not collapsed, to produce the third preliminary fermented liquid pn3 of pH 4.8± and a second fermented medium m2.

More particularly, the second process $p_2 2$ for producing a third fermented liquid n3 of pH 4.5± in the second fermentation line f2 comprises preliminary steps as follows.

The second process $p_2 2$ comprises the steps of:
enclosing the second fermented medium m2 produced in the first step $p_2 1$ in the bag-shaped medium filter 320, suspending the bag-shaped medium filter 320 inside of the third fermentation tank 300, and transferring the third preliminary fermented liquid pn3 of pH 4.8± into the third fermentation tank 300, as shown in FIG. 1;

transferring the second fermented liquid of pH 5.0± from the second fermentation tank 200 into the third fermentation tank 300 by the extraction unit 210 of the second fermentation tank 200 shown in FIG. 1, coupled to the third fermentation tank 300; and activating the circulating pump unit 330 shown in FIG. 9 to integrally circulate the third preliminary fermented liquid pn3 of pH 4.8± and the second fermented liquid n2 of pH 5.0± through the bag-shaped medium filter320, such that the second fermented medium m2 is not mixed into the fermented liquids, and fermenting them for 8 to 9 days with maintaining fermentation condition at 37° C. to 40° C. to finally produce a third fermented liquid n3 of pH 4.5± as shown in stage 2 in FIG. 16.

A third feature configuring a method according to an embodiment of the present invention for producing a fermented liquid having an acidity of pH 3 to 4 comprising colloidal particles having a particle size not exceeding 50 nm and short-chain fatty acids is a third fermentation line f3 in the multi-stage fermentation process.

The third fermentation line f3 uses a fourth fermentation system s4. As shown in FIGS. 1 [13] to [16] and FIG. 12 [a] to [g], the fourth fermentation system s4 comprises:

a third medium tank 50 shown in FIGS. 1 [13] and [14] and FIG. 12 [b];

one fourth fermentation tank 400 shown in FIG. 1 and FIG. 12 [d]; and an extraction unit 310 of the third fermentation tank 300, to be coupled to the fourth fermentation tank 400 shown in FIG. 12 [e].

The third fermentation line f3 is configured by a first process $p_3 1$ for producing a third fermented medium m3 of pH 4.4±; and a second process $p_3 2$ for producing a fourth fermented liquid n4 of pH 3.7±.

Entire process of the third fermentation line f3 is shown in FIGS. 1 [13] to [16]. More particularly, the first process $p_3 1$ for producing a third fermented medium m3 of pH 4.4±comprises preliminary steps as follows.

The first process $p_3 1$ comprises the steps of:
into the third medium tank 50 as shown in FIG. 12 [b] to [c], putting a honey material pm3 corresponding to 3 to 5% of the volume of the third fermented liquid n3 produced in the third fermentation tank 300, the honey material pm 3 preferably consisting of a polyfloral honey and an acacia honey in a ratio of 1:4, and further putting a part of the third fermented liquid n3 of pH 4.5±, corresponding to four times as much as the volume of the honey material, as a starter;

stirring the honey material pm3 and the part of the third fermented liquid n3 in the third medium tank 50 to produce a preliminary fermented medium pfm3, and fermenting the preliminary fermented medium pfm3 for 2 or 3 days with maintaining fermentation condition at 37° C. to 40° C. as shown in step $pp_3 1$ in FIG. 12 to finally produce a third fermented medium m3 of pH 4.4± by as shown in stage 2 in FIG. 16.

More particularly, the second process $p_3 2$ of the third fermentation line f3 for producing a fourth fermented liquid n4 of pH3.7± comprises preliminary steps as follows.

The second process $p_3 2$ comprises the steps of:

transferring the third fermented medium m3 to the fourth fermentation tank 400 as shown in FIG. 12[*d*];

transferring the third fermented liquid n3 of pH 4.5± from the third fermentation tank 300 to the fourth fermentation tank 400 as a starter by the extraction unit 310 of the third fermentation tank 300, coupled to the fourth fermentation tank 400, and stirring them, as shown in FIG. 12 [*e*] to [*f*], and fermenting them for 30 to 60 days with maintaining fermentation condition at 37° C. to 40° C. to finally produce a fourth fermented liquid n4 of pH 3.7± as shown in FIG. 12 [*g*] and stage 2 in FIG. 16.

A fourth feature configuring a method according to the present invention for producing a fermented liquid having an acidity of pH 3 to 4 comprising colloidal particles having a particle size not exceeding 50 nm and short-chain fatty acids is a fourth fermentation line f4 in a multi-stage fermentation process.

The fourth fermentation line f4 uses a fifth fermentation system s5. The fifth fermentation system comprises:

one fifth fermentation tank 500 shown in FIG. 1; and an extraction unit 410 of the fourth fermentation tank 400, to be coupled to the fifth fermentation tank 500 (the principle of operation of the extraction unit 410 is same as that of the extraction unit 310 of FIG. 12 [*e*], and not shown).

The fourth fermentation line f4 is configured by a process $p_4 1$ for producing a fifth fermented liquid n5 of pH 3.6± from the fourth fermented liquid n4 of pH 3.7± as shown in FIG. 12 [*g*]

More particularly, the process $p_4 1$ of the fourth fermentation line f4, for producing a fifth fermented liquid n5 of pH 3.6±, comprises preliminary steps as follows.

As shown in FIGS. 1 [16] to [17], the process $p_4 1$ comprises the steps of:

transferring the fourth fermented liquid n4 of pH 3.7± as a starter from the fourth fermentation tank 400 to the fifth fermentation tank 500 by the extraction unit 410 of the fourth fermentation tank 400, coupled to the fifth fermentation tank 500;

stirring the fourth fermented liquid n4 of pH 3.7±several times in the fifth fermentation tank 500 to establish a fermentation environment without using any fermented medium; and fermenting the fourth fermented liquid n4 by fermentation bacteria b1 for 30 to 60 days with maintaining fermentation condition at 37° C. to 40° C. to finally produce a fifth fermented liquid n5 of pH 3.6± as shown in stage 2 in FIG. 16.

A fifth feature configuring a method according to an embodiment of the present invention, for producing a fermented liquid having an acidity of pH 3 to 4 comprising colloidal particles having a particle size not exceeding 50 nm and short-chain fatty acids is a fifth fermentation line f5 in a multi-stage fermentation process.

The fifth fermentation line f5 uses a sixth fermentation system s6. As shown in FIGS. 1 [18] to [19] or FIG. 15 [*a*] to [*c*], the sixth fermentation system comprises:

one sixth fermentation tank 600 shown in FIG. 1 or FIG. 15 [*c*];

a cooling unit 610 shown in FIG. 1 or FIG. 15 [*b*]; and a reserve tank 620 shown in FIG. 15 [*a*] and an extraction unit 510 of the fifth fermentation tank 500, to be coupled to the reserve tank 620.

The fifth fermentation line f5 is configured by:

a first process $p_5 1$ for rapidly cooling the fifth fermented liquid n5 of pH 3.6± at 35 to 40° C. to a liquid temperature at 4 to 5° C. or lower as shown in FIG. 1 or FIG. 15 [*b*]; and a second process $p_5 2$ for returning the rapidly cooled fifth fermented liquid n5 of pH 3.6± to an ordinary temperature condition, and producing a sixth fermented liquid n6 having an acidity of pH 3.3± with maintaining the ordinary temperature condition as shown in FIG. 1 or FIG. 15 [*c*].

More particularly, the first process $p_5 1$ of the fifth fermentation line f5 for rapidly cooling the fifth fermented liquid n5 of pH 3.6± at 35 to 40° C. to a liquid temperature at 4 to 5° C. or lower comprises preliminary steps as follows.

The process $p_5 1$ comprises the steps of:

transferring the fifth fermented liquid n5 of pH 3.6± at 35 to 40° C. from the fifth fermentation tank 500 to the reserve tank 620 coupled to the extraction unit 510 of the fifth fermentation tank 500 as shown in FIG. 15 [*a*], immersing the reserve tank 620 into cooling water in the cooling unit 610 as shown in FIG. 15 [*b*], to rapidly cool the fermented liquid n5 at 35 to 40° C. to a liquid temperature finally at 4 to 5° C. or lower.

More particularly, the second process $p_5 2$ of the fifth fermentation line f5 for producing a sixth fermented liquid n6 of pH 3.3± with maintaining the ordinary temperature condition as shown in FIG. 15 [*c*] comprises preliminary steps as follows.

The second process $p_5 2$ comprises the steps of:

removing the reserve tank 620 from the cooling unit 610 and returning the rapidly cooled fifth fermented liquid n5 to an ordinary temperature condition, then transferring the fifth fermented liquid n5 to the sixth fermentation tank 600 as shown in FIG. 15 [*c*];

establishing a fermentation environment without using any fermented medium; and fermenting the fifth fermented liquid n5 of pH 3.6± by fermentation bacteria b1 in the fifth fermented liquid n5 for 180 to 240 days with maintaining ordinary temperature condition, to finally produce a sixth fermented liquid n6 of pH 3.3±.

As described above, a method according to the present invention is a method generally configured by the first fermentation line f1 to the fifth fermentation line f5, for producing a fermented liquid having an acidity of pH 3 to 4 comprising colloidal particles having a particle size not exceeding 50 nm and short-chain fatty acids, the short-chain fatty acids comprising three kinds of short-chain fatty acid, that is butyric acid, propionic acid, and lactic acid.

When a charge amount for the two first fermentation tanks 100 shown in FIG. 1, that is an amount of the second preliminary fermented liquid pn2, is assumed to be 1800 L, an amount of the soft water w to be used as a starter and an amount of the fermented liquid to be produced in each stage can be estimated as follows.

When four pottery fermentation bottles 10 are used, 20 L of soft water w is used for soaking 6.5 kg of dried soybeans ds for each fermentation bottle 10, as shown in FIGS. 2 (1) to (2). Therefore, 80 L of the soft water w is used for four fermentation bottles 10 in total. Then, the fermented soybeans fs in each fermentation bottle 10 are ground into paste while small amount, i.e., about 5 L, of soft water w is added, to obtain soybean paste gfs. The soybean paste gfs is transferred to each of another four containers 11 shown in FIG. 2 (3) and mixed with the first preliminary fermented liquid pn1. At this time, about 10 L of soft water w is further added to each container 11. The soybean paste gfs and the first preliminary fermented liquid pn1 with the 10 L of soft water w are transferred from each container 11 to the heating kettle 30, and then heated. The heated soybean paste gfs and the first preliminary fermented liquid pn1 (gfs+pn1+w) corresponding to 35 L per each fermentation bottle 10 are transferred into the first medium tank 20.

In the heating kettle 30, soft water w corresponding 10 L is added to the soybean paste gfs and the first preliminary fermented liquid pn1 corresponding to 35 L per each fermentation bottle 10, with stirring them. Then, the soybean paste gfs and the first preliminary fermented liquid pn1 is cooled to a fermentation temperature in the first medium tank 20, in which soft water w corresponding 100 L has been prepared for cooling. As a result, an amount of the soft water w required to produce the first fermented medium m1 becomes 180 L (80 L+20 L+40 L+40 L). The soft water w used for cooling in the first medium tank 20 is 100 L. Therefore, the first fermented medium m1 to be produced corresponds to 240 L (35 L×4+100 L).

In the two first fermentation tanks 100, soft water w is further added to the 240 L of the first fermented medium m1 and 270 to 450 L of the seed bacterial liquid b as a starter.

When a charge amount for the two first fermentation tanks 100, that is an amount of the second preliminary fermented liquid pn2, is assumed to be 1800 L, an amount of the soft water to be added to the two first fermentation tanks 100 shown in FIG. 2 [c] becomes 1110 to 1290 L. Therefore, an amount of the soft water w required to be used for producing the first fermented liquid n1 becomes 1290 L (1110 L+180 L) to 1470 L (1290 L+180 L). In the method for producing a fermented liquid having an acidity of pH 3 to 4 comprising colloidal particles having a particle size not exceeding 50 nm and short-chain fatty acids according to the present invention, other processes will not use any soft water w.

In each of the two first fermentation tanks 100 after 50 to 100 days fermentation in stage 1 in FIG. 16, as shown in FIG. 2 [d] or FIG. 4 [a], a sponge layer formed of fermentation gas, having an air-blocking effect, and a first deposition layer dep 1 containing fibrous materials from the first fermented medium m1 are formed, and a translucent first intermediate layer liquid is formed between these two layers. The translucent first intermediate layer liquid is the first fermented liquid n1 of pH 5.3±.

When the charge amount for the two first fermentation tanks 100, that is an amount of the second preliminary fermented liquid pn2 is assumed to be 1800 L, since 30% or more of the second preliminary fermented liquid is absorbed by the sponge layer sp and the first deposition layer dep 1, the first fermented liquid n1 of pH 5.3± produced in each first fermentation tank 100 corresponds to 600 to 650 L.

Therefore, the first fermented liquid n1 of pH 5.3±, extracted from the two first fermentation tanks 100 by the extraction unit 110 of the first fermentation tank 100 coupled to the second fermentation tank 200 and transferred to the second fermentation tank 200, corresponds to 1200 to 1300 L. The first fermented liquid n1 of pH 5.3± is an initial fermented liquid for producing a fermented liquid having an acidity of pH 3 to 4 comprising colloidal particles having a particle size not exceeding 50 nm and a shot-chain fatty acid according to the present invention.

In the second fermentation tank 200, a fermentation environment without using any medium is established, and the second fermented liquid n2 of pH 5.0± is produced by fermenting the first fermented liquid n1 of pH 5.3± by the fermentation bacteria b1 included in the first fermented liquid n1. In the second fermentation tank 200, a supernatant first surface film layer sf1 containing fermentation gas bubbles generated from the fermentation of the first fermented liquid n1 of pH 5.3± is formed at a top layer, a second deposition layer dep2 is deposited at a bottom layer, and a translucent second intermediate layer liquid is formed between these two layers.

The second intermediate layer liquid is the second fermented liquid n2 of pH 5.0±. Since about 5% of the second fermented liquid n2 is absorbed by the first surface film layer 1 and the second deposition layer dep2 during the fermentation, about 1140 to 1240 L of the second fermented liquid n2 is produced.

The first fermentation line f1 is completed at this stage. The first fermentation line f1 corresponds to stage 1 in the FIG. 16 and requires fermentation period of about 55 days or more and not exceeding 108 days.

The second fermentation line f2 shown in FIGS. 1 [9] to [12] uses about 1140 to 1240 L of the second fermented liquid n2 of pH 5.0± as a starter. A part of the second fermented liquid n2 is added to the second medium tank 40. Residual second fermented liquid n2 is transferred to the third fermentation tank 300. According to the inventor's steady practical experience, it is found that about 8 to 10% of the third fermentation liquid n3 is lost during the fermentation in the third fermentation tank 300, and thus the final amount of the third fermentation liquid n3 of pH 4.5± to be produced becomes about 1050 to 1100 L.

In the third fermentation line f3 to the fifth fermentation line f5 shown in FIG. 1 to [19], loss of the fourth fermented liquid n4 to sixth fermented liquid n6 due to vaporization etc. during fermentation is small amount, i.e., 2 to 3%, and thus the final amount of the sixth fermented liquid n6 of pH 3.3± to be produced, comprising colloidal particle having a particle size not exceeding 50 nm, becomes about 1000 to 1050 L.

An amount of each fermented liquid to be produced by the fermentation in each stage can be estimated as follows. In the two first fermentation tank 100, the soft water w corresponding to 1290 to 1470 L as a starter and the first fermented medium m1 are used to produce the first fermented liquid n1 of pH 5.3±corresponding to 1800 L of the charge amount. The first fermented liquid n1 is used as a next starter to produce about 1140 to 1240 L of the second fermented liquid n2 of pH 5.0±. Then, the second fermented liquid n2 and the second fermented medium m3 are used to produce about 1050 to 1100 L of the third fermentation liquid n3 of pH 4.5±. In the following fermentation, the third fermentation liquid n3 and the third fermented medium m3 are used to produce the fourth fermented liquid n4 of pH 3.7±. After this stage, a fermentation environment without using any fermented medium is established, and the fourth fermented liquid n4 is used to produce the fifth fermented liquid n5 of pH 3.6±, and then the fifth fermented liquid n5 is used to finally produce about 1000 to 1050 L of the sixth fermented liquid n6 of pH 3.3±.

BRIEF DESCRIPTION OF DRAWINGS

FIG. 5 shows photographs A and B of a comparative test first fermented liquids A and B, wherein the first fermented liquid A is produced by fermenting a first fermented medium sample A for 6 days, the sample A being prepared by grinding preliminarily fermented soybeans, and the first fermented liquid B is produced by fermenting a fermented medium sample B for 6 days similarly as the sample A, the sample B being prepared by grinding dried soybeans soaked in a water without being preliminarily fermented.

FIG. 6 is a list of seven species of fermentation bacteria comprising spore-forming *Clostridium* producing organic acids including short-chain acids. The strains on the list were domestically deposited to National Institute of Technology and Evaluation (NPMD), which is an International Depositary Authority (IDA) under the terms of the Budapest Treaty, under Accession Numbers. NITE P-02945, NITE P-02946, NITE P-02947, NITE P-02948, NITE P-02949, NITE P-02950, and NITE P-02951 on May 16, 2019, and have been transferred to the international deposit on Apr. 22, 2020 in the same institute under International Accession Numbers NITE BP-02945, NITE BP-02946, NITE BP-02947, NITE BP-02948, NITE BP-02949, NITE BP-02950, and NITE BP-02951.

FIG. 7 is a schematic view of a second medium tank, provided with a perforated inner lid having bores through which fermentation gas can pass.

FIG. 8 is a schematic view of a bag-shaped medium filter to be suspended inside of a third fermentation tank, used in a second fermentation line for producing a third fermented liquid by a second fermented medium, and a perspective view and top view of the third fermentation tank with the bag-shaped medium filters being placed.

FIG. 10 shows photographs A and B of a comparative test for third fermented liquids A and B, wherein the third fermented liquid A is produced by preliminary fermenting Jujube, *Lycium* Fruit, and Turmeric in a weight ratio of 7 to 4 to 1 using a second fermented liquid, grinding and crashing them to the extent that seeds of the Jujube remain, to prepare a second fermented medium sample A, and performing a fermentation for 5 days using the sample A, and the third fermented liquid B is produced by grinding and crashing Jujube, *Lycium* Fruit, and Turmeric in a weight ratio of 7 to 4 to 1 soaked in a second fermented liquid, without being preliminarily fermented, to the extent that seeds of the Jujube remain to prepare a second fermented medium sample B, and performing a fermentation for 5 days using the sample B, similarly as the sample A.

FIG. 13 shows photographs A and B of a comparative test for fourth fermented liquids A and B, wherein the fourth fermented liquid A is produced by fermenting a third fermented liquid and a third fermented medium for 4 days, the third fermented medium being produced by preliminarily fermenting a honey material, and the fourth fermented liquid B is produced by fermenting the third fermented liquid and a medium of honey material without preliminary fermentation, for 4 days.

FIG. 19 is tables showing results of analysis of sugar amount in 100 g [mL] of fermented liquids measured by Somogyi modified method at Japan Food Research Laboratories.

FIG. 20 is graphs showing result of analysis of short-chain acid amount in 100 g [mL] of sixth fermented liquid measured by high-performance liquid chromatography at Japan Food Research Laboratories.

FIG. 21 is bar graphs showing calcium increment amount and calcium absorption rate based on a result of "test for evaluating calcium absorption with everted gut sac method" using male SD rats as model animals and administering a test material (sixth fermented liquid).

DESCRIPTION OF EMBODIMENTS

An embodiment of the present invention is described as follows. The embodiment of the present invention provides a method for producing a fermented liquid having an acidity of pH 3 to 4 comprising colloidal particles having a particle size not exceeding 50 nm and short-chain fatty acids, by multi-stage fermentation process. The short-chain fatty acids may comprise butyric acid, propionic acid, and lactic acid. The fermented liquid produced by the method of the present invention may contain the colloidal particles at a content of 6.5 to 7.5%, and 0.5 to 0.6 g of the butyric acid per 100 mL of the fermented liquid. The fermented liquid produced by the method of the present invention may be used, by itself, a functional food or a raw material liquid for functional food.

Details of a First Fermentation Line f1

Figure 1:
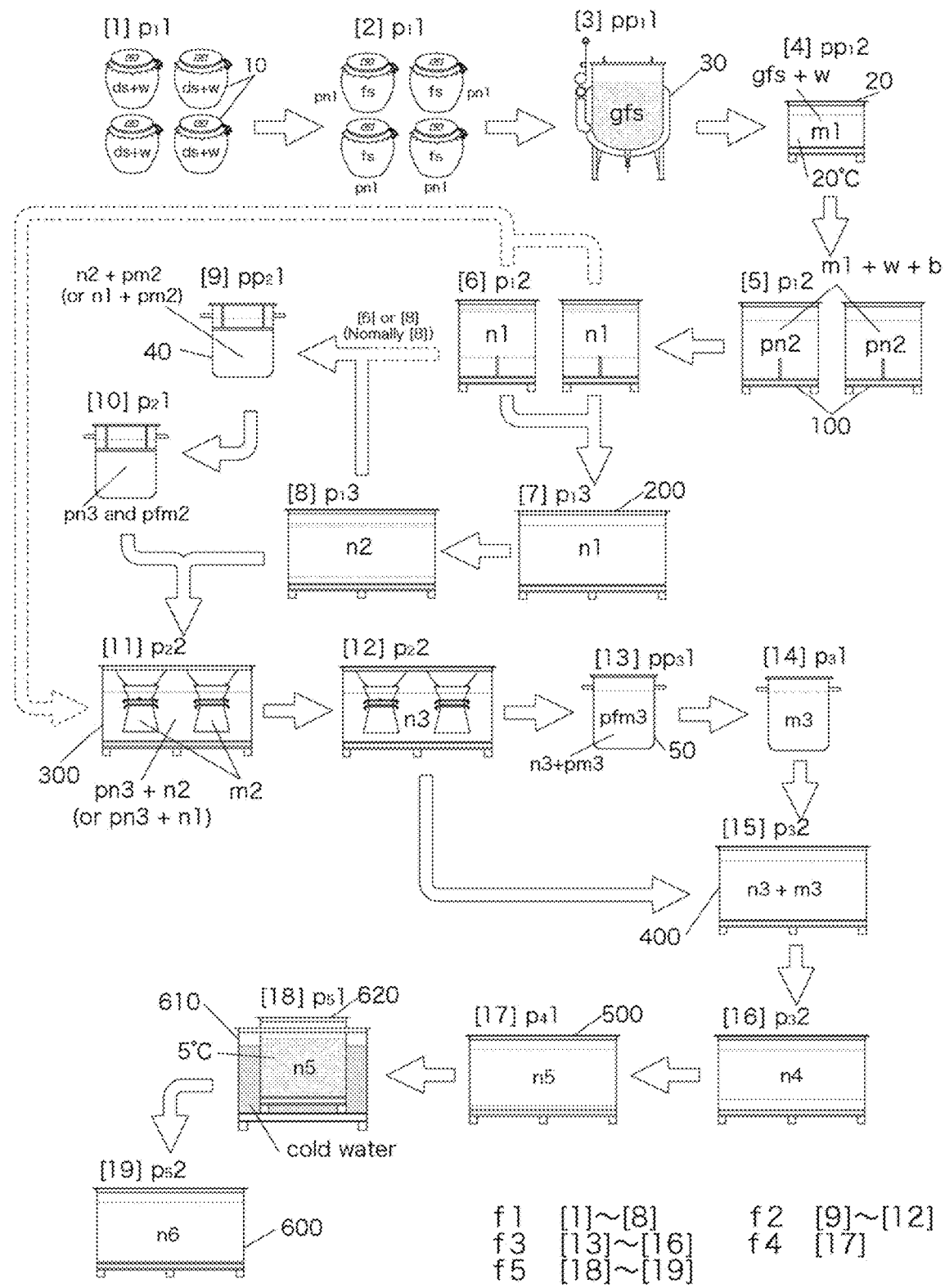
FIG. 1 is a schematic diagram illustrating a multi-stage fermentation process comprising first to fifth fermentation lines, for producing a fermented liquid having an acidity of pH 3 to 4 comprising colloidal particles having a particle size not exceeding 50 nm.

More particularly, the multi-stage fermentation starts at a first process $p_1 1$ configuring a first fermentation line f1, as shown in FIG. 1, wherein FIG. 1 is a schematic view illustrating a method of the present invention.

When a charge amount for producing a first fermented liquid n1 in the first fermentation line f1, that is an amount of a second preliminary fermented liquid pn2 is assumed to be 1800 L, a charge amount as a starter and a final amount to be produced for each process can be estimated as follows.

Figure 2:
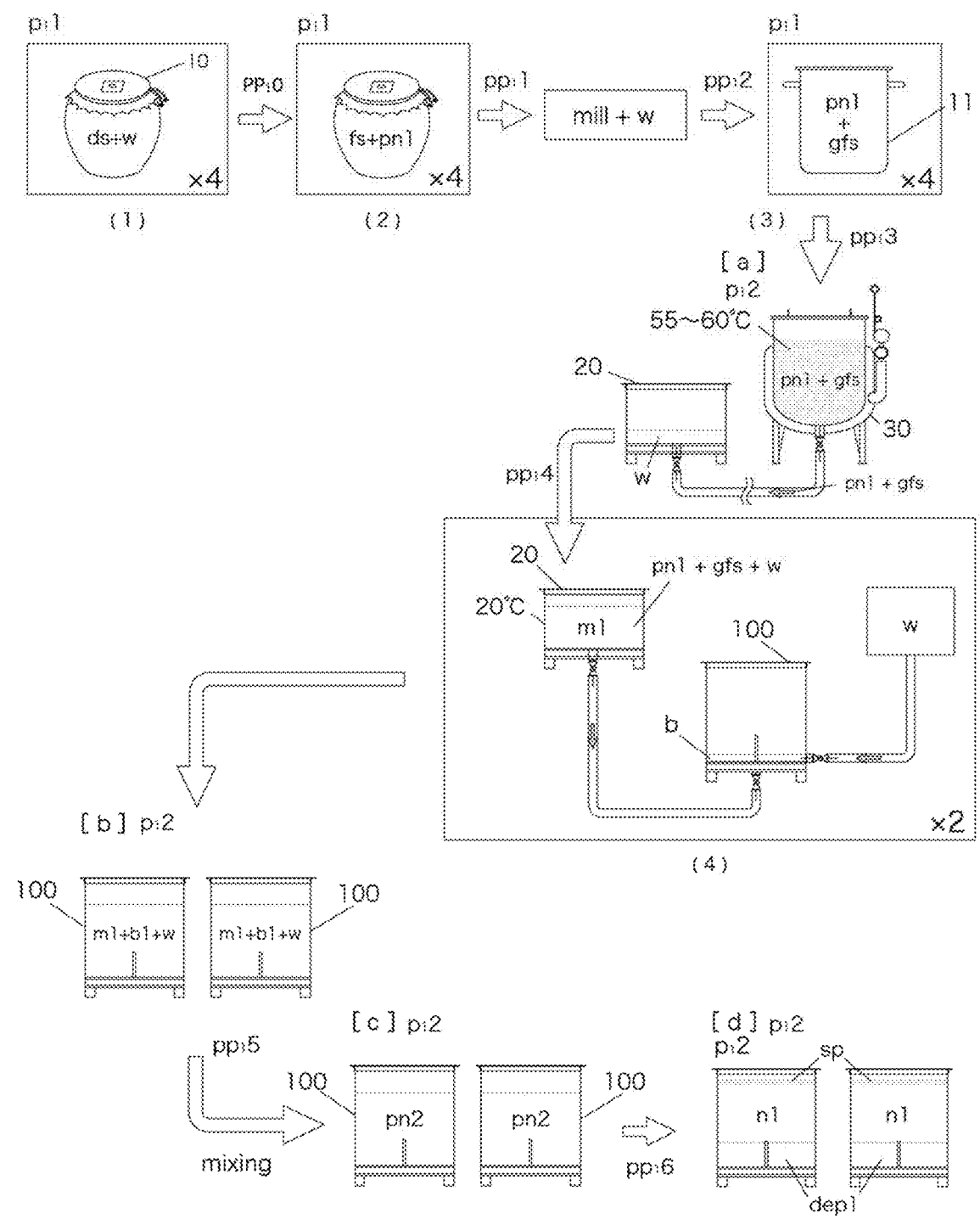
FIG. 2 is an enlarged schematic view illustrating a first process and a second process configuring the first fermentation line, the second process consisting of a first preliminary process, a second preliminary process, and a third preliminary process.

As shown in FIGS. 2 (1) and (2), the first process $p_1 1$ of the first fermentation line f1 comprises a first preliminary process $pp_1 1$ consisting of a first pre-treatment process and a second pre-treatment process.

Figure 3:
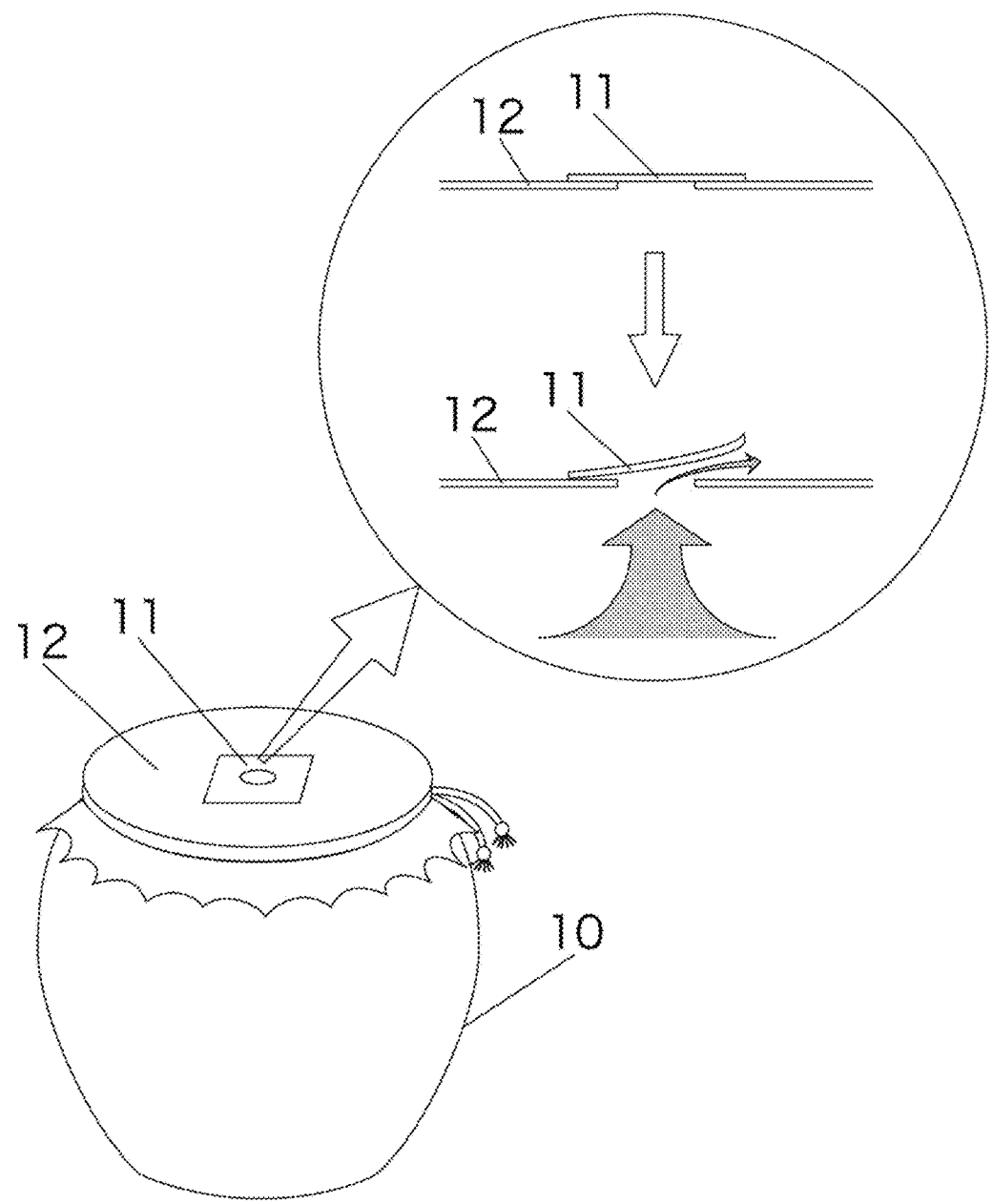
FIG. 3 is a perspective view showing a fermentation bottle having a volume not exceeding 60 L, provided with a lid having valve functionality at a center of the lid, and an enlarged schematic view showing a mechanism of the lid

In the first pre-treatment process, dried soybeans corresponding to 6.5 kg are soaked and reconstituted in 20 L of a soft water w of pH 7.3± in each of four pottery fermentation bottles 10 shown in FIG. 3. Each fermentation bottle 10 has a volume not exceeding 60 L and being provided with a lid 12 having a valve functionality 11 at a central part of the lid for allowing a fermentation gas to escape. An amount appropriate to the dried soybeans corresponding to 6.5 kg, more specifically 0.25 kg of a sugar chain s, and a part of, more specifically 0.14 L of a seed bacterial liquid b as shown in FIG. 6 are put into each fermentation bottle 10.

In the second pre-treatment process, the contents of the fermentation bottles 10 are fermented for 3 days (68 to 74 hours) to produce a first preliminary fermented liquid pn1 and fermented soybeans fs, corresponding to 35 L per each fermentation bottle 10.

As shown in FIG. 2 (3), the first process $p_1 1$ of the first fermentation line f1 further comprises a second preliminary process $pp_1 2$. In the second preliminary process $pp_1 2$, the fermented soybeans fs of the second pre-treatment process configuring the first preliminary process $pp_1 1$ are removed from each fermentation bottle 10, and ground into a paste by a grinding means (not shown) with small amount of the soft water w being added. The ground fermented soybeans fs are transferred into four containers 11 corresponding the fermentation bottles 10, and mixed with the first preliminary fermented liquid pn1 of the second pre-treatment process to produce the first preliminary fermented liquid pn1 and a soybean paste gfs, corresponding to 35 L per each container 11.

As shown in FIG. 2 (3), the first process $p_1 1$ of the first fermentation line f1 further comprises a third preliminary process $pp_1 3$. In the third preliminary process $pp_1 3$, the first preliminary fermented liquid pn1 and the soybean paste gfs produced in each container 11, corresponding to 35 L, is transferred from each container 11 into a heating kettle 30, gradually heated to 55 to 60° C., and stirred to produce the first preliminary fermented liquid pn1 and the soybean paste gfs corresponding to 180 L [(35 L+10 L)×4] in total in the heating kettle 30.

A second process $p_1 2$ of the first fermentation line f2 further comprises a fourth preliminary process $pp_1 4$ to sixth preliminary process $pp_1 6$.

In the fourth preliminary process $pp_1 4$ of the second process $p_1 2$, the first preliminary fermented liquid pn1 and the soybean paste gfs produced in the heating kettle 30 in the third preliminary process $pp_1 3$ of the first process $p_1 1$, corresponding to 180 L, is transferred, with avoiding exposure to external air, into a first medium tank 20 preliminarily containing soft water w corresponding to 100 L for cooling, and stirred to produce a first fermented medium m1 of pH 4.5± corresponding to 280 L.

As shown in FIG. 2 (4), in the fourth preliminary process $pp_1 4$ of the second process $p_1 2$, the 280 L of first fermented medium m1 of pH 4.5± in the first fermented tank 20, 270 to 450 L of a seed bacterial liquid b in which fermentation bacteria b1 shown in FIG. 6 being preliminarily made to be in a symbiotic and stable state, and 1100 to 1300 L of soft water w are divided into two first fermentation tanks 100 equally, with avoiding exposure to external air. As shown in FIG. 2 [b], the first fermented medium m1 and the seed bacterial liquid b are stirred with the soft water w in each first fermentation tank 100, to produce a second preliminary fermented liquid pn2 of pH 6.4± corresponding to 1800 L in total.

Figure 4:
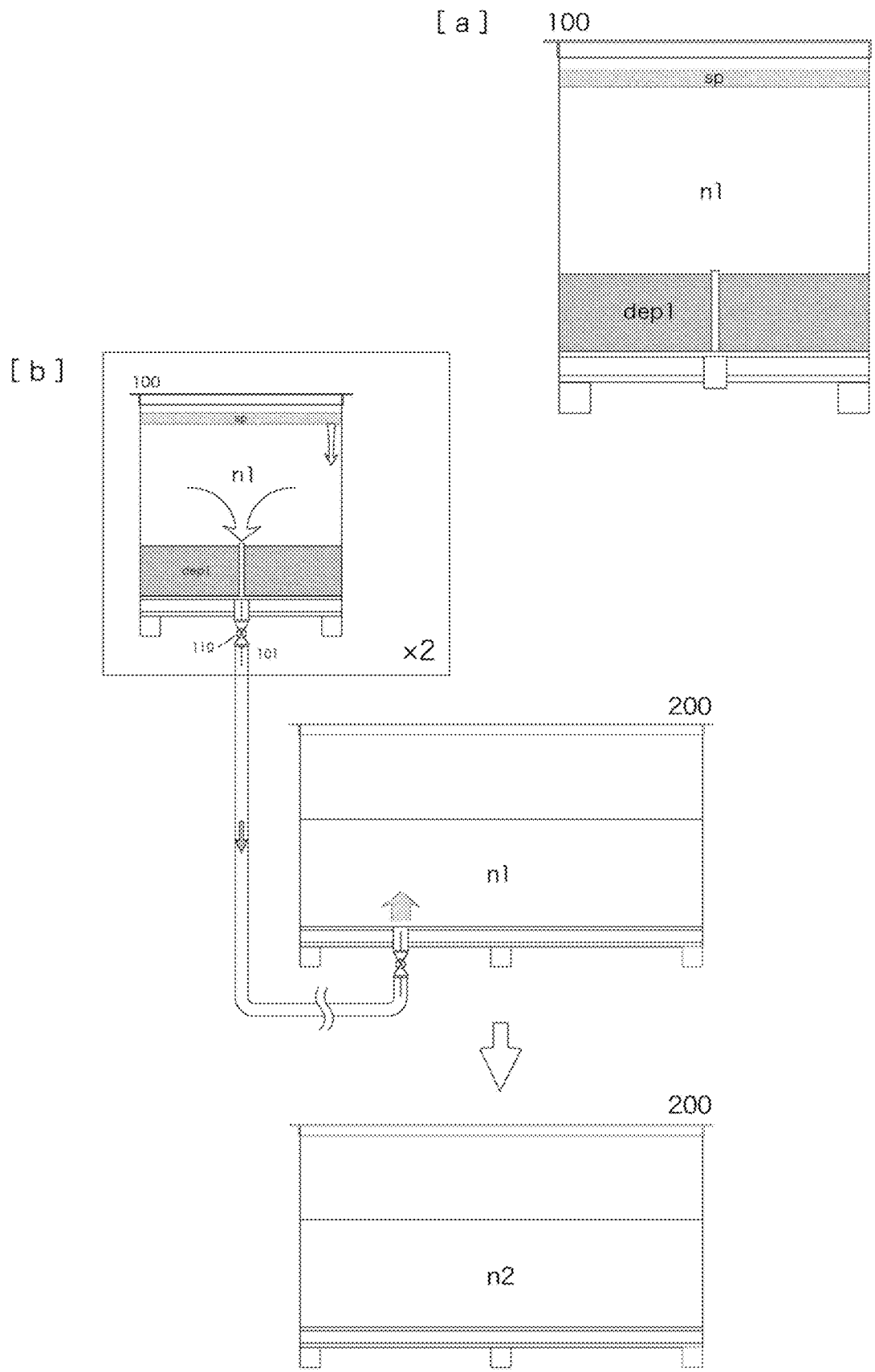
FIG. 4 is a schematic view showing a manner in which only a first fermented liquid, that is a first intermediate layer liquid produced in a first fermentation tank is extracted and transferred to a second fermentation tank, by opening and closing a shut-off valve of an extraction unit attached to the bottom of the first fermentation tank, utilizing Pascal's principle and hydrostatic equilibrium.

In the fifth preliminary process $pp_1 5$ and the sixth preliminary process $pp_1 6$ of the second process $p_1 2$ shown in FIG. 2 [c] and [d], the second preliminary fermented liquid pn2 of pH 6.4± are enclosed in each first fermentation tank 100 with avoiding exposure to external air, and fermented for 50 to 100 days with maintaining fermentation condition at 37° C. to 40° C. to form a supernatant sponge layer sp by fermentation gas bubbles as shown in FIG. 4 [a]. The sponge layer sp prevents oxygen from dissolving into the liquid to facilitate secretion and fermentation of acidic material by the fermentation bacteria b1 in the seed bacterial liquid b. A paste-like first deposition layer dep1 is formed at a bottom layer, in which fibrous materials from the first fermented medium m1 and the fermentation bacteria b1 are deposited. A translucent first intermediate layer liquid is formed between the sponge layer sp and the first deposition layer dep1. The translucent first intermediate layer liquid is the first fermentation liquid n1 of pH 5.3±.

In each fermentation tank 100, the sponge layer sp swelled by the long-term fermentation and the paste-like first deposition layer dep1 occupy a volume corresponding to 300 L in total, and thus the first fermentation liquid n1 of pH 5.3±, which is the translucent first intermediate layer liquid, may correspond to 600 L. The supernatant sponge layer sp and the paste-like first deposition layer dep1 may become base materials for the seed bacterial liquid b.

The first fermentation line f1 may further comprises a third process $p_1 3$. In the third process $p_1 3$, the first fermented liquid n1 of pH 5.3±, which is the first intermediate layer liquid corresponding to 600 L produced in each first fermentation tank 100, is transferred into one second fermentation tank 200 as shown in FIG. 4 [b].

The third process $p_1 3$ uses the first fermented liquid n1 of pH 5.3±corresponding 1200 L transferred into the one second fermentation tank 200 as a starter, and the first fermented liquid n1 is fermented for 3 to 5 days by fermentation bacteria b1 of the seed bacterial liquid b contained in the first fermented liquid n1 to produce a second fermented liquid n2 of PH 5.0±.

Technical Problem for Producing the Second Fermented Liquid n2

The third process $p_1 3$ has a feature in that the first fermented liquid n1 is fermented only by the fermentation bacteria b1 of the seed bacterial liquid b, in an environment without using medium or fermented medium. Here, a technical problem for the third process $p_1 3$ of the first fermentation line f1 is considered. The two lots of first fermented liquid n1 separately produced in the two fermentation tanks 100 may have different fermentation environments each other, due to symbiosis of the fermentation bacteria b1 of the seed bacterial liquid b. The symbiosis and antagonism of the fermentation bacteria b1 of the seed bacterial liquid b contained in the first fermented liquid n1 may be further stimulated by transferring the two lots of first fermented liquid n1 into one second fermentation tank 200 and mixing them to be unified. This may be estimated from the fact that the first fermented liquid of pH 5.3± is acidified to the second fermented liquid n2 of pH 5.0±.

Therefore, as indicated by two routes shown in FIG. 1 or [8], it may be possible that the multi-stage fermentation process of the present invention directly proceeds from the second process $p_1 2$ of the first fermentation line f1 to a second fermentation line f2, without going through the third process $p_1 3$ of the first fermentation line f1.

In the case when the process directly proceeds from the second process $p_1 2$ of the first fermentation line f1 to a second fermentation line f2, one fermentation tank (not shown) having a size similar as that of the second fermentation tank 200 may be used. The inventors found that, from their steady practical work for many years, when the process does not go through the third process $p_1 3$ of the first fermentation line f1, the symbiosis and antagonism of the fermentation bacteria b1 remains low level, that is, secretion and fermentation of acidic materials by the fermentation bacteria b1 cannot sufficiently proceed, and thus, it is not so easy to stably produce the first fermented liquid n1 of pH 5.3±corresponding 1200 L in the one first fermentation tank. Therefore, in order to preliminarily ferment the first fermented liquid n1 of PH 5.3±until it becomes the second fermented liquid n2 of pH 5.0±, it may be necessary to further modification and more fermentation days. Based on such knowledge, the inventors have addressed such a problem and conceived an idea that the third process $p_1 3$ is integrated in the first fermentation line f1 to solve the problem.

In fact, in the third process $p_1 3$ of the first fermentation line f1, the first fermented liquid n1 of pH 5.3± is fermented for 3 to 5 days only by the fermentation bacteria b1 with maintaining a fermentation condition at 37° C. to 40° C. to form a supernatant first surface layer sf1 of fermentation gas bubbles. The first surface layer sf1 prevents oxygen from dissolving into the liquid to further facilitate secretion and fermentation by the fermentation bacteria b1. A paste-like second deposition layer dep2 is formed at a bottom layer, in which residue of the first fermented medium m1 is deposited. Between the first surface layer sf1 and the second deposition layer dep2, a translucent second intermediate layer liquid corresponding 1140 to 1240 L is formed. The translucent second intermediate layer liquid is the second fermented liquid n2 of pH 5.0±. Whether the third process $p_1 3$ is integrated in the first fermentation line f1 or not is an issue of choice.

Technical Feature of the First Fermentation Line f1

A technical feature of the first fermentation line f1 is that, in contrast to conventional soybeans fermentation, dried soybeans ds are preliminarily fermented in fermentation bottles 100 to produce a first preliminary fermented liquid pn1 and a soybean paste gfs, and a first fermented medium m1 are produced from the first preliminary fermented liquid pn1, the soybean paste gfs, a soft water w, and a part of the seed bacterial liquid b. The preliminarily fermented first fermented medium m1 of pH 4.5± and a soft water w are used to produce a first fermented liquid n1 of pH 5.3±.

Usually, fermentation products using soybeans are produced in a condition in which soybeans ds are soaked in a liquid such as a material to be fermented or water. On the other hand, the inventors have achieved the present invention by focusing on producing a fermented liquid via a process for preliminary fermenting the first fermented medium m1 using dried soybeans, to produce the first fermented liquid n1 of pH 5.3±.

FIG. 5 shows photographs A and B of a comparative test for first fermented liquids A and B. The first fermented liquid A is produced by fermenting a first fermented medium sample A for 6 days, wherein the sample A is prepared by grinding preliminarily fermented soybeans. The first fermented liquid B is produced by fermenting a fermented medium sample B for 6 days similarly as the sample A, wherein the sample B is prepared by grinding dried soybeans soaked in a water without being preliminarily fermented.

The photograph A shows the first fermented liquid A produced by fermenting the sample A for 6 days, wherein the sample A is prepared by preliminarily fermenting 60 g of soybeans, grinding the preliminarily fermented soybeans to produce a soybean paste, heating the soybean paste and a soft water w to 55° C., then cooling them to 37° C., adding 0.8 L of seed bacterial liquid b, and stirring them, with assuming 4 L of first fermented liquid n1 is to be produced. As apparent from the photograph A, three layers are clearly formed in the first fermented liquid A, including a supernatant sponge layer sp, a deposition layer dep, and, between these two layers, an highly transparent intermediate liquid n1 corresponding to 4 L.

The photograph B shows the fermented liquid B for compering with the photograph A, the fermented liquid B being produced by fermenting the sample B for 6 days, wherein the sample B is prepared by soaking 60 g, i.e, same amount as that of sample A, of soybeans in water for 18 hours as it is, grinding the soybeans to produce a soybean paste without being preliminarily fermented, heating the soybean paste and a soft water w are heated to 55° C., then cooling them to 37° C., adding 0.8 L of seed bacterial liquid b, and stirring them. As apparent from the photograph B, although intermediate liquid having lower transparency and a deposition layer are formed, almost no supernatant sponge layer sp is formed, the sponge layer being necessary to fermentation environment for fermentation bacteria b1, as a result of producing the fermented liquid B under a condition using soybean paste without preliminary fermentation, different from that of the sample A.

The result of the comparative test shown in FIG. 5 reveals that there is critical difference in fermentation environment between the fermented liquid A with preliminary fermentation of dried soybeans for the first medium, and the fermented liquid B without preliminary fermentation. More specifically, the comparative test may demonstrates a technical matter that it is necessary to form the supernatant sponge layer sp for blocking air for the fermentation environment using the fermentation bacteria group b1 contained in the seed bacterial liquid b. In fact, fishy smell arose from the fermented liquid B having no supernatant sponge layer sp. It may be assumed that, due to the exposure of the fermentation bacteria b1 to external air, number of the bacteria is decreased, and rot and oxidation progress and become dominant over the fermentation effect, and result in the smell.

It is apparent from the result of the test shown in photographs A and B in FIG. 5 that it is an essential process for achieving the production of the first fermented liquid n1 of pH 5.3± according to the method of the present invention to preliminarily fermenting the first medium for producing the first fermented medium m1 so as to form the supernatant sponge layer.

Details of a Second Fermentation Line f2

A fermentation line f2 is configured by:

a first process $p_2 1$ for preliminarily producing a second fermented medium m2 of pH 4.8± in a second medium tank 40, as shown in FIGS. 1 [9] and [10]; and a second process $p_2 2$ for producing a third fermented liquid n3 of pH 4.5± in a third fermentation tank 300 and a third fermentation system s3, as shown in FIG. 1, using the second fermented medium m2 of pH 4.8± produced in the first process $p_2 1$ and the second fermented liquid n2 of pH 5.0± as a second starter. As used herein the starter means row materials.

The first process $p_2 1$ of the second fermentation line f2 includes, as a preliminary step, preparing a second medium tank 40, provided with a perforated inner lid 41 having bores through which a fermentation gas passes, and to be sealed with a sheet 42, as shown in enlarged view of FIG. 7 [a].

The first process $p_2 1$ further includes, as shown in FIG. 7 [a], putting into the second medium tank 40, a preliminarily prepared mixed medium pm2, and either a part of the second fermented liquid n2 or a part of the first fermented liquid n1, after experiencing one or two days of fermentation during their fermentation process, such that the total volume of the mixed medium and the fermented liquid corresponds to 35 L, and stirring them, fermenting them for two or three days with maintaining a fermentation condition at 37° C. to 40° C. to produce a preliminary fermented mixed medium pfm2 and a third preliminary fermented liquid pn3, as shown in FIG. 7 [b], according to processes not shown, grinding the preliminary fermented mixed medium pfm2 by a grinding means to the extent that seeds of Jujube are not collapsed, and returning the ground preliminary fermented mixed medium pfm2 to the second medium tank 40, and blending the ground preliminary fermented mixed medium pfm2 with the third preliminary fermented liquid pn3 to produce a second fermented medium m2 of pH 4.8±.

The preliminarily prepared mixed medium pm2 is a mixed medium in which sterilized dried plants consisting of Jujube, *Lycium* Fruit, and Turmeric are mixed in a weight ratio of 200 to 210 g of Jujube, 110 to 120 g of *Lycium* Fruit, and 25 to 30 g of Turmeric for the second fermented liquid n2 corresponding to 35 L in total. Jujube (Taiso), *Lycium* Fruit (Kukoshi), and Turmeric (Ukon) are medicinal natural products and listed in crude drugs in the Japanese Pharmacopoeia. Taiso is a fruit of jujube, Kukoshi is a fruit of *Lycium*, and Ukon is a rhizome of a plant of Zingiberaceae. Based on inventor's steady practice for many years, these plants were selected from many crude drugs.

Technical Feature of the Second Fermentation Line f2

Based on their try-and-error practice for many years, the inventors have achieved the first process $p_2 1$ of the second fermentation line f2, in which the mixed medium pm2 is prepared by mixing 200 to 210 g of Jujube, 110 to 120 g of *Lycium* Fruit, and 25 to 30 g of Turmeric (weight ratio of 7:4:1) per 35 L of the second fermented liquid n2 in total, the mixed medium pm2 is preliminarily fermented in the second medium tank 40 to produce the preliminary fermented mixed medium pfm2 and the third preliminary fermented liquid pn3, as shown in FIG. 7 [a] and [b], and the preliminary fermented mixed medium pfm2 are ground by a grinding means to the extent that seeds of Jujube are not collapsed, and returned to the second medium tank 40, the ground preliminary fermented mixed medium pfm2 are blended with the third preliminary fermented liquid pn3 to produce a second fermented medium m2 of pH 4.8±, according to a process not shown.

When the third process $p_1 3$ is integrated in the first fermentation line f1, a process partly overlapped with the process $p_1 3$ for fermenting the second fermented liquid n2 is preferably adopted as the first process $p_2 1$ of the second fermentation line f2.

First technical reason for adopting a concurrent parallel arrangement in which the first process $p_2 1$ and the process $p_1 3$ for fermenting the second fermented liquid n2 are partly overlapped, instead of linearly arranging the first process $p_2 1$ and the process $p_1 3$, is for changing a fermentation environment of the fermentation bacteria b1 during the fermentation process. By changing the fermentation environment, secretion and fermentation of acidic material by the fermentation bacteria b1 are further facilitated, and the second fermented medium m2 can be produced more rapidly.

Second technical reason is for adjusting a start time of the process $p_2 2$ for fermenting the third fermented liquid n3 to an end time of the process $p_1 3$ for fermenting the second fermented liquid n2. It makes possible to start the first process $p_2 1$ of the second fermentation line f2 for producing the second fermented medium m2, without waiting the end of the process $p_1 3$ for fermenting the second fermented liquid n2, which is the third process of the first fermentation line f1. As a result, the second process $p_2 2$ of the second fermentation line f2 for producing the third fermented liquid n3 is started no later than the end of the third process $p_13$ for fermenting the second fermented liquid n2 of the first fermentation line f1.

Figure 11:
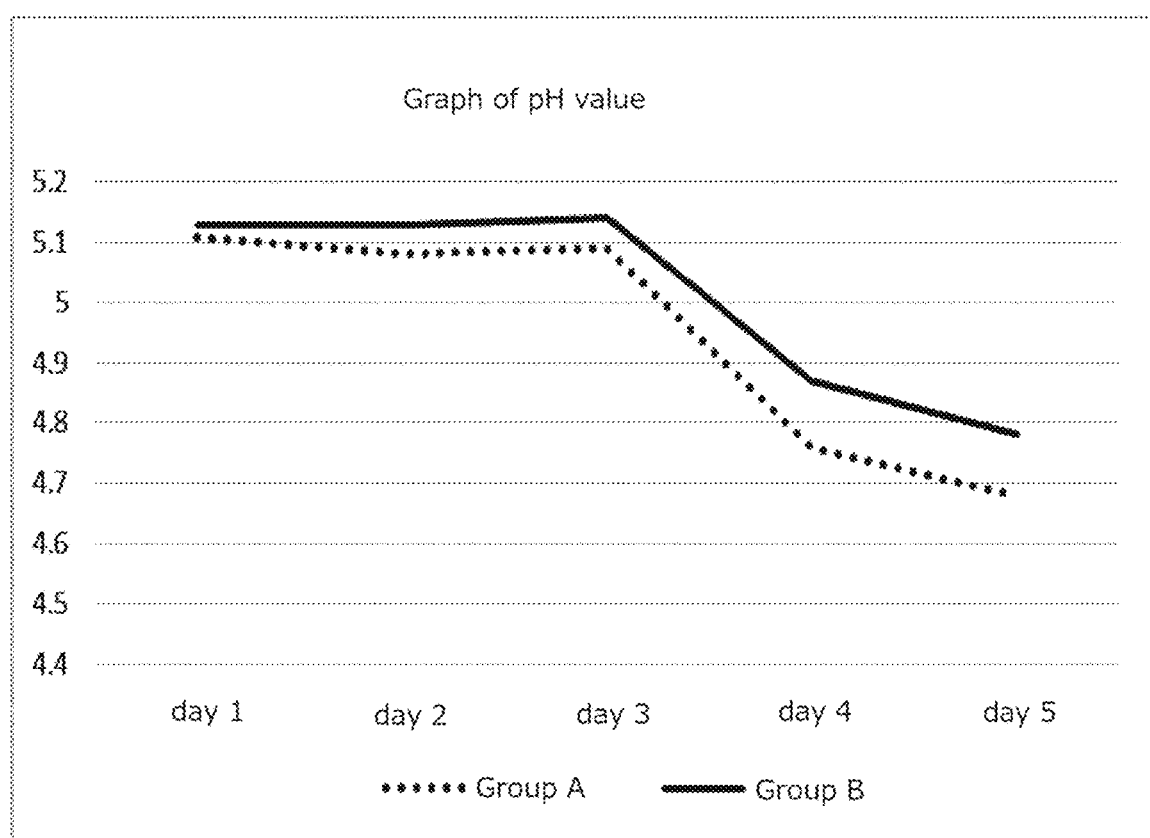
FIG. 11 is a graph and a comparative table showing change of acidity of pH value of the third fermented liquid A and the third fermented liquid B for 5 days from the beginning of the fermentation.

A technical meaning of the second fermentation line f2 using the second fermented medium m2 prepared by preliminarily fermenting the dried plants pm2 of the selected three crude drugs in the first process $p_21$ is demonstrated from a result of a comparative test for samples A and B of fermentation models of the third fermentation liquid n3 shown FIG. 10 and an analytical result of difference of degree of fermentation progress between the samples A and B shown in FIG. 11.

The second fermentation line f2 comprises a process $p_21$ for producing a second fermented medium m2. The process $p_21$ comprises a preliminary process $pp_21$. In the preliminary process $pp_21$, a mixed medium pm2 is preliminarily fermented with a part of the second fermented liquid n2 in a second fermentation tank 40, to produce a third preliminary fermented liquid pn3 and a preliminary fermented mixed medium pfm2, wherein the mixed medium pm2 is prepared by mixing 200 to 210 g of Jujube, 110 to 120 g of *Lycium* Fruit, and 25 to 30 g of Turmeric (weight ratio of 7:4:1) per 35 L of the second fermented liquid n2 in total. The process $p_21$ further comprises a preliminary process $pp_22$. In the preliminary process $pp_22$, the preliminary fermented mixed medium pfm2 are ground by a grinding means to the extent that seeds of Jujube are not collapsed, returned to the second medium tank 40, and blended with the third preliminary fermented liquid pn3 to produce the second fermented medium m2 of pH 4.8±.

The second fermentation line f2 further comprises a process $p_22$ for producing a third fermented liquid n3 of pH 4.5±. The process $p_22$ shown in FIGS. 1 [11] to [12] comprises a preliminary process $pp_21$. In the preliminary process $pp_21$, the second fermented medium m2 produced in the process $p_21$ is enclosed in bag-shape medium filters 320, and suspended inside of a third fermentation tank 300. The third preliminary fermented liquid pn3 is transferred from the second medium tank 40 to the third fermentation tank 300, and the second fermented liquid n2 of pH 5.0±also transferred from the second fermentation tank 200 to the third fermentation tank 300. The process $p_22$ further comprises a preliminary process $pp_22$. In the preliminary process $pp_22$, the third preliminary fermented liquid pn3 and the second fermented liquid n2 are circulated such that the second fermented medium m2 in the bag-shape medium filter 320 is not mixed into the fermented liquids, and fermented for 8 to 9 days with maintaining fermentation condition at 37° C. to 40° C. to produce the third fermented liquid n3 of pH 4.5±corresponding to 1050 L.

FIG. 10 shows photographs A and B showing a result of comparative test for samples A and B of fermentation models of the third fermented liquid n3.

The sample A is a fermented liquid A prepared by preliminarily fermenting 1 L of second fermented liquid n2 and a mixed medium pm2 consisting 5.71 g of Jujube, 3.14 g of *Lycium* Fruit, and 0.85 g of Turmeric (weight ratio of 7:4:1) corresponding to 1 L of the second fermented liquid n2, enclosing the preliminarily fermented second fermented medium m2 in a filter for crude drags, as a substitute for the bag-shaped medium filter, suspending the filter inside of a test container A, putting the second fermented liquid n2 and a third preliminary fermented liquid pn3 corresponding to 1 L as a starter into the test container A, stirring them, and fermenting them for 5 days with maintaining fermentation condition at 38° C. to 40° C. to form the fermented liquid A consisting of two layers including a supernatant fermentation gas layer and a layer of turbid third fermented liquid n3 (photograph A in FIG. 10).

The sample B is a fermented liquid B prepared by, without preliminary fermentation, enclosing 1 L of second fermented liquid n2 and a mixed medium pm2 consisting 5.71 g of Jujube, 3.14 g of *Lycium* Fruit, and 0.85 g of Turmeric (weight ratio of 7:4:1) corresponding to 1 L of the second fermented liquid n2 in a filter for crude drags, as a substitute for the bag-shaped medium filter, suspending the filter inside of a test container B, putting the second fermented liquid n2 and a third preliminary fermented liquid pn3 corresponding to 1 L as a starter into the test container B, stirring them, and fermenting them for 5 days with maintaining fermentation condition at 38° C. to 40° C. to form the fermented liquid B consisting of a third fermented liquid n3 in which almost no supernatant fermentation gas layer is formed (photograph B in FIG. 10). The fermented liquid B is critically different from the fermented liquid A in that almost no supernatant fermentation gas layer is formed.

The result of the comparative test demonstrates that the difference between the fermented liquids A and B may result from a difference in degree of fermentation due to secretion and metabolism of acidic materials by the fermentation bacteria b1. More specifically, the fermentation of the fermented liquid A due to secretion and metabolism by the fermentation bacteria b1 further progresses than that of the fermentation of liquid B.

FIG. 11 represents the difference in degree of fermentation between the fermented liquids A and B as a change of acidity for five days. The fermented liquid A always shows a pH value lower than, namely, an acidity higher than, that of the fermented liquid B. For three days, an acidity of the fermented liquid A remains at pH 5.11 to pH 5.09 and an acidity of the fermented liquid B remains at pH 5.13 to pH 5.14. That is, acidity of the fermentation A>the acidity of the fermentation B, and no significant change is found in both acidities. However, on the fourth and the fifth days, it is apparent that both acidities are increased, and the acidity of the fermented liquid A is acidified to pH 4.76 to 4.68, and the acidity of the fermented liquid B is acidified to pH 4.87 to 4.78. That is, the acidity of the fermentation A>the acidity of the fermentation B, and certain degree of fermentation due to secretion and metabolism by the anaerobic fermentation bacteria b1 is found in both acidities.

The graph of FIG. 11 also shows a result in that by using the preliminarily fermented second fermented medium m2 for producing the third fermented medium n3, the fermentation environment of the fermentation bacteria b1 may be changed, and thus secretion and metabolism of acidic materials by the fermentation bacteria b1 may be enhanced to facilitate the fermentation. It is a technical meaning of using the preliminarily fermented second fermented medium m2 for producing the third fermented medium n3.

In the first preliminary process $pp_21$ of the second process $p_22$ of the second fermentation line f2, as shown in FIG. 1, the second fermented medium m2 of pH 4.8± produced in the first process $p_21$ is equally divided and enclosed in a plurality of steam-sterilized bag-shaped medium filters 320 suspended inside of the third fermentation tank 300, the third preliminary fermented liquid pn3 produced in the first process $p_21$ is transferred from the second medium tank 40 into the third fermentation tank 300, the second fermented liquid n2 of pH 5.9± is transferred from the second fermentation tank 200 into the third fermentation tank 300 via the extraction unit 210 of the second fermentation tank 200, coupled to the third fermentation tank 300.

Figure 9:
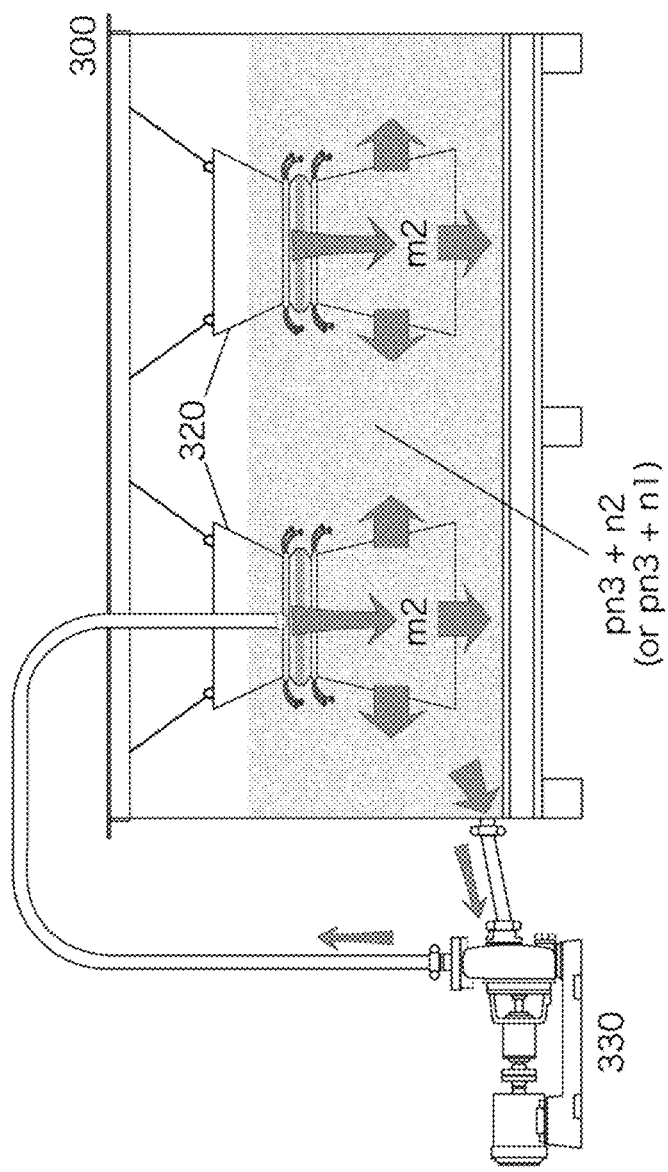
FIG. 9 is a schematic view of a third fermentation tank equipped with a circulation pump unit used in a second fermentation line for producing a third fermented liquid by a second fermented medium.

In the second preliminary process $pp_2 2$ of the second process $p_2 2$ of the second fermentation line f2, a circulating pump unit 330 shown in FIG. 9 is activated to integrally circulate through the second fermented medium m2 of pH 4.8± enclosed in the bag-shaped medium filter 320 suspended inside of the third fermentation tank 300, such that the second fermented medium m2 is not mixed into other materials, the third preliminary fermented liquid pn3 of pH 4.8± and the second fermented liquid n2 of pH 5.0± as a second starter in the third fermentation tank 300, and ferment them for 8 to 9 days with maintaining fermentation condition at 37° C. to 40° C. to produce a third fermented liquid n3 of pH 4.5± consisting of a turbid liquid with supernatant second surface layer sf2.

In the second process $p_2 2$ of the second fermentation line f2, the second fermented medium m2 is enclosed in fine mesh bag-shaped medium filter 320, and thus, any residue of the second fermented medium m2 is not deposited at the bottom of the third fermentation tank 300. It is confirmed that, during the second fermented liquid n2 changes to the third fermented liquid n3, the acidity of the third fermented liquid n3 proceeds to pH 5 or lower.

Details of a Third Fermentation Line f3

A third fermentation line f3 shown in FIGS. 1 [13] to [16] consists of a first process $p_3 1$ for producing a third fermented medium m3 of pH 4.4± and a second process $p_3 2$ for producing a fourth fermented liquid n4 of pH 3.7±.

Figure 12:
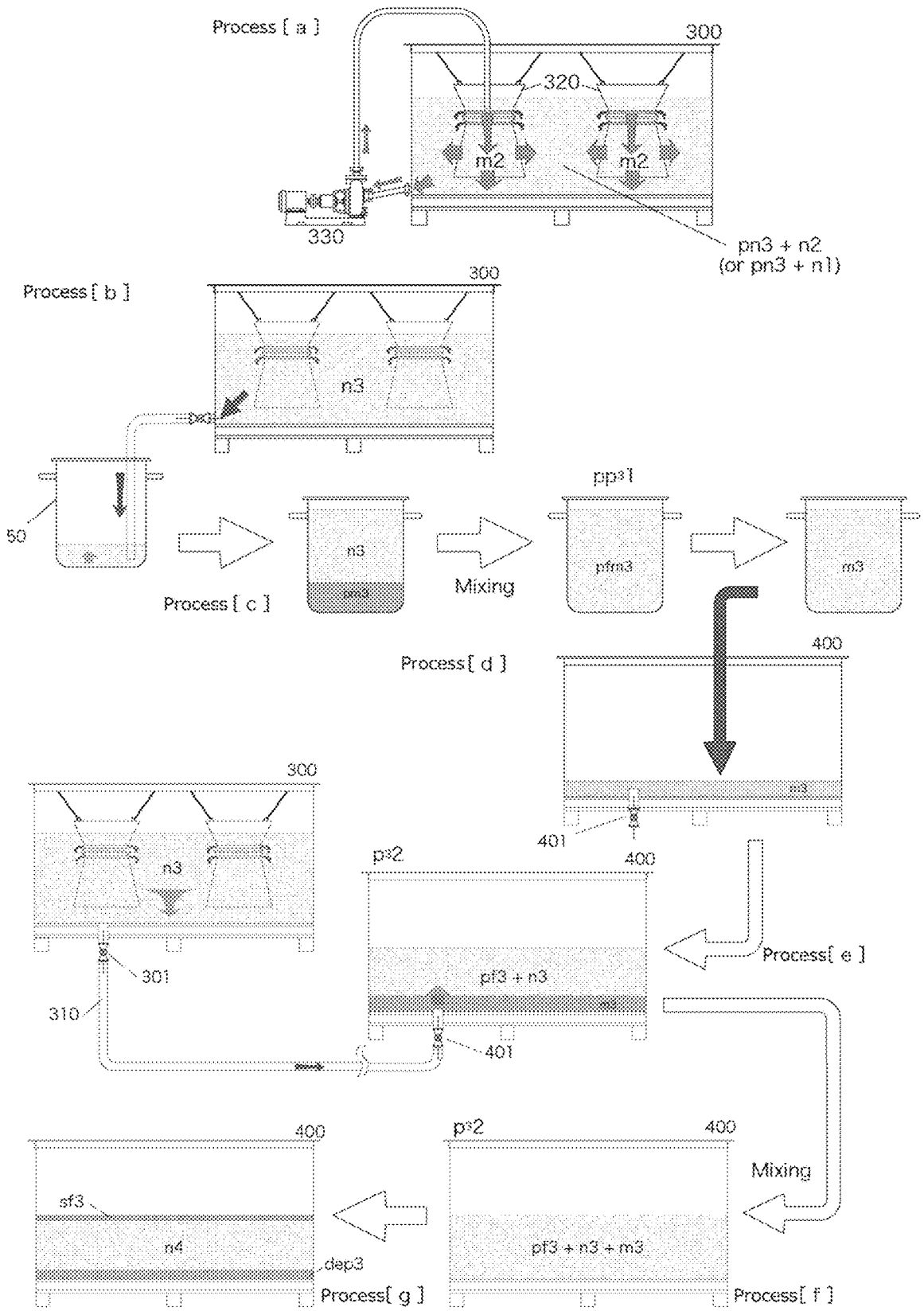
FIG. 12 is a partial enlarged view consisting of schematic views of processes [a] to [g], wherein the process [a] represents the second fermentation line in which a second fermented liquid is transferred to a third fermentation tank, a second fermented medium produced in a second medium tank is put into bag-shaped medium filters suspended inside the third fermentation tank, a circulation pump unit is actuated to circulating them, and the content of the third fermentation tank is fermented with circulation to produce a third fermented liquid, the processes [b] and [c] is a process in which a portion of the third fermented liquid and an adequate amount of honey material are put into a third medium tank and fermented with stirring to produce a third fermented medium, and the processes [d] to [g] represents the third fermentation line in which the third fermented liquid transferred from the third fermentation tank and the third fermented medium are put into the fourth fermentation tank, and fermented with stirring to produce a fourth fermented liquid.

An overview of the third fermentation line f3 is shown in FIG. 12. FIG. 12 shows process [a] in which the second fermented liquid n2 produced in the second fermentation line f2 has been transferred into the third fermentation tank 300, and the second fermented medium m2 produced in the second fermentation tank 40 is put into bag-shaped medium filters 320 placed inside of the third fermentation tank 300, and a circulating pump unit 330 is activated to circulating and fermenting them for 8 to 9 days to produce the third fermentation liquid n3.

The third fermentation line f3 includes a process [c] in which a part of the third fermented liquid n3 of the third fermentation tank 300 and an adequate amount of a honey material pm3 is put into a third medium tank 50, stirred, and fermented for 2 or 3 days with maintaining fermentation condition at 37° C. to 40° C. to produce a third fermented medium m3.

The third fermentation line f3 further includes processes [d] to [g] in which the third fermentation liquid n3 transferred from the third fermentation tank 300 and the third fermented medium m3 are put into a fourth fermentation tank 400, stirred, and fermented for 30 to 60 days with maintaining fermentation condition at 37° C. to 40° C. to produce a fourth fermented liquid n4.

More specifically, the first process $p_3 1$ comprises a first preliminary process $pp_3 1$ in which a honey material pm3 corresponds to 3 to 5% of 1050 to 1100 L of the third fermented liquid n3 produced as shown in FIG. 12 [a] to [b], wherein honey material pm3 consists of polyfloral honey and an acacia honey in a ratio of 1:4, and a part of the third fermented liquid n3 corresponding to four times as much as the amount of the honey material are transferred into a third medium tank 50, with avoiding exposure to external air, and stirred, to produce a preliminary fermented medium pfm 3 as shown FIG. 12 [c].

The first process $p_3 1$ further comprises a second preliminary process $pp_3 2$ in which the preliminary fermented medium pfm3 produced in the first preliminary process $pp_3 1$ is fermented for 2 or 3 days with maintaining fermentation condition at 37° C. to 40° C. to produce a third fermented medium m3 of pH 4.4± from the honey material pm3.

In the second process $p_3 2$ of the third fermentation line f3, as shown in FIG. 12 [d] to [g], the third fermented medium m3 of pH 4.4± is put into a fourth fermentation tank 400, the third fermented liquid n3 of pH 4.5± is transferred into the fourth fermentation tank 400 by a extraction unit 310 of the third fermentation tank 300, coupled to the fourth fermentation tank 400, the third fermented medium m3 of pH 4.4± and the third fermented liquid n3 of pH 4.5± are mixed and stirred as a fourth starter, and fermented for 30 to 60 days with maintaining fermentation condition at 37° C. to 40° C. to form a supernatant third surface layer sf3 and a third deposition layer dep 3 containing a deposition at a bottom layer, and produce a translucent third intermediate layer liquid corresponding to 1000 to 1050 L between the third surface layer sf3 and the third deposition layer dep 3. The translucent third intermediate layer is a fourth fermented liquid n4 of pH 3.7±.

Technical Feature of the Third Fermentation Line f3

The inventors conceived the third fermentation line f3 based on their steady try-and-error practice for many years, and have repeated try-and error to enhance growth and ability of secretion and metabolism of the fermentation bacteria b1 by providing certain amount of sugar to the fermentation bacteria b1, and achieve continuous fermentation due to further secretion and metabolism of acidic materials.

With repeating the try-and-error, the inventors found that a suitable sugar amount for maintaining the ability of the secretion and metabolism of the fermented bacteria b1 may correspond to a honey material pm3 corresponding to 3 to 5% of the third fermented liquid n3, based on a degree of water activity (if it is too low, activity of bacteria in water is inhibited and the bacteria cannot grow). The honey material pm3 was mixed and stirred with the third fermented liquid n3 four times as much as the amount of the honey material pm3 to produce a preliminary fermented medium pfm3. The preliminary fermented medium pfm3 was fermented for 2 or 3 days with maintaining fermentation condition at 37° C. to 40° C. to produce a third fermented medium m3.

Figure 14:
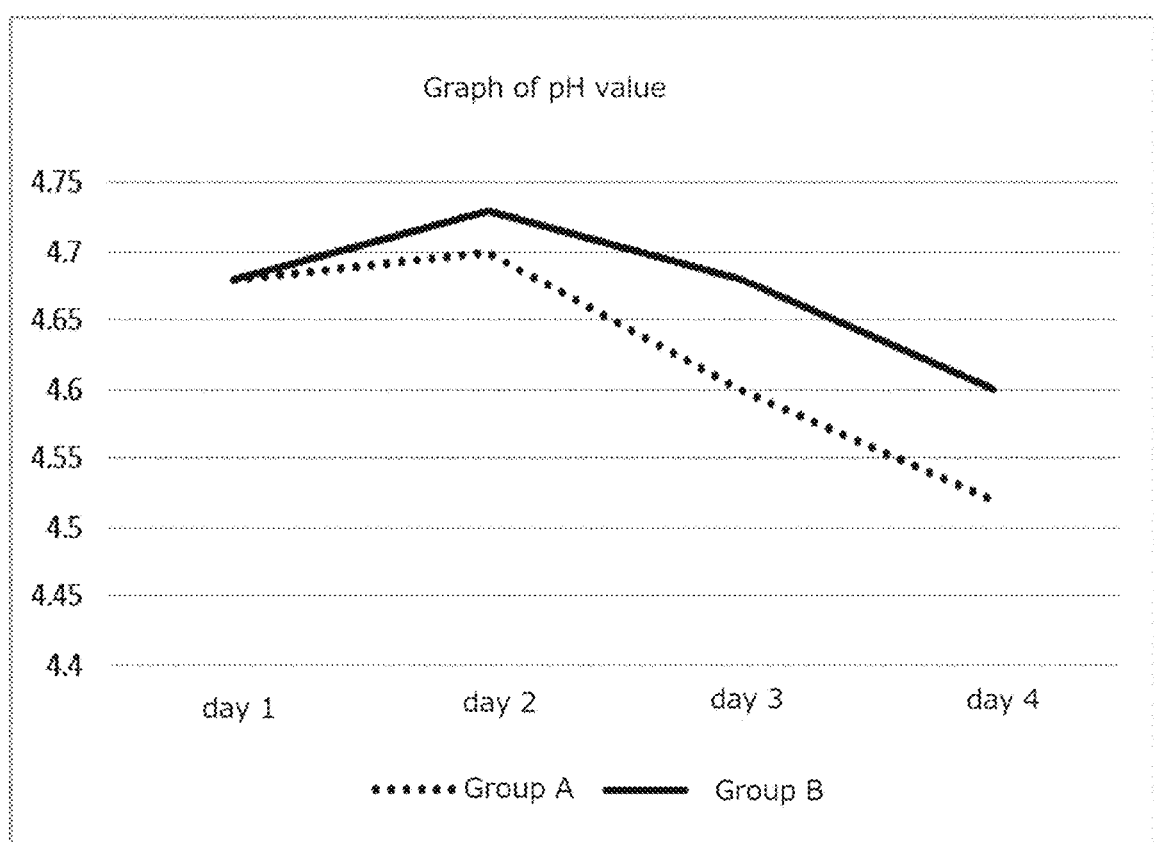
FIG. 14 is a graph and a comparative table showing change of acidity of pH value of the fourth fermented liquid A and the third fermented liquid B for 4 days from the beginning of the fermentation.

Further, the third fermented medium m3 was mixed and stirred with a third fermented liquid n3 twenty times as much as the amount of the third fermented medium m3, and fermented for 30 to 60 days with maintaining fermentation condition at 37° C. to 40° C. to facilitate the fermentation due to the secretion and metabolism of acidic material by fermentation bacteria b1. In this manner, the inventors succeeded to produce a fourth fermented liquid n4 of pH 3.7±. This is the third fermentation line f3. The technical feature of the third fermentation line f3 is shown in FIGS. 13 and 14.

FIG. 13 shows photographs A and B showing a result of comparative test for samples A and B of fermentation models of the fourth fermentation liquid n4.

The sample A is a fermented liquid A, which is a fourth fermented liquid n4 prepared by mixing a third fermented medium m3 produced by preliminarily fermenting a honey material pm3 with a third fermented liquid n3 twenty times as much as the volume of the third fermented medium m3 such that total amount becomes 1 L, stirring them, and fermenting them for 4 days with maintaining fermentation condition at 38° C. to 40° C. The sample B is a fermented liquid B, which is a fourth fermented liquid n4 prepared by mixing a honey material pm3 (third medium pm3) as it is with a third fermented liquid n3 twenty times as much as the volume of the third medium pm3 such that total amount becomes 1 L, stirring them, and fermenting them for 4 days.

The sample A is the fermented liquid A prepared by putting the third fermented medium m3 produced by preliminarily fermenting the honey material pm3 into one test container, stirring them, and fermenting them for 4 days to form three layers including a supernatant third surface layer sf3 of fermentation gas layer, a third deposition layer dep 3 containing deposition deposited at bottom layer, and a translucent intermediate layer liquid between the third surface layer sf3 and the third deposition layer dep 3. The translucent third intermediate layer liquid corresponds to the fourth fermented liquid n4.

The sample B is the fermented liquid B prepared by putting the honey material pm3 as it is into other test container, stirring them, and fermenting them for 4 days. From photograph B, it is confirmed that a supernatant third surface layer sf3 is formed, but much thinner than that of the sample A. It reveals that the fermentation of the sample B due to secretion and metabolism of acidic materials by the fermentation bacteria b1 is less active than that of the sample A. This is confirmed from FIG. 14.

FIG. 14 represent a change of acidity of the fermented liquids A and B for 4 days fermentation. On the first day, an acidity of the fermented liquid A and an acidity of the fermented liquid B are both pH 4.6. On the second day, both pH values increase (acidities decrease) to pH 4.7 for the fermented liquid A and pH 4.73 for the fermented liquid B. On the third and fourth days, as degree of fermentation progresses, both pH values decrease (acidities increase) to pH 4.6 to 4.52 for the fermented liquid A, whereas pH 4.68 to 4.6 for the fermented liquid B. On the second to fourth days, always, the acidity of the fermentation A>the acidity of the fermentation B.

FIG. 14 is a graph showing the change of the acidity of the fermented liquids A and B for four days from the start of the fermentation. The difference between the fermented liquids A and B represent that the degree of fermentation of the fermented liquid A is higher than that of the fermented liquid B as the pH value of acidity of the fermented liquid A is always lower than that of the fermented liquid B for four days. The fact demonstrates that the fermentation bacteria b1 in the fermented liquid A secretes acidic materials more active than fermented liquid B. That is, the inventors successfully activate the fermentation bacteria b1 so as to enhance the secretion and metabolism of acidic material, by using the third fermented medium m3 produced by preliminarily fermenting the honey material pm3 for producing the fourth fermented liquid n4, instead of using the honey material pm3 as it is, to change the fermenting environment for the fermented bacteria b1.

Details of a Fourth Fermentation Line f4

In the fourth fermentation line f4 shown in FIG. 1, the fourth fermented liquid n4 of pH 3.7± is used as a fifth starter, and fermented by only the fermented bacteria b1 contained in the fourth fermented liquid n4 for 30 to 60 days with maintaining fermentation condition at 37° C. to 40° C. to produce a fifth fermented liquid n5 of pH 3.6±. This is a process $p_4 1$ of the fourth fermentation line f4. During the fermentation process, loss of the fermented liquid is very few, and thus the fifth fermented liquid n5 corresponding to 1000 to 1050 L is produced.

The process $p_4 1$ of the fourth fermentation line f4 is a process for producing the fifth fermented liquid n5 via following processes.

In the first fermentation line f1, the first fermented liquid n1 is produced in two first fermentation tanks 100 by using the first fermented medium m1 and transferred into one second fermentation tank 200 in the first process $p_1 1$ and the second process $p_1 2$, and the second fermented liquid n2 is produce in a fermentation environment without using any fermented medium in the third process $p_1 3$. In the second fermentation line f2, the third fermented liquid n3 is produced by using the second fermented liquid n2 produced in the third process $p_1 3$ of the first fermentation line f1 and the second fermented medium m2 produced in the second medium tank 40. In the third fermented line f3, the fourth fermented liquid n4 is produced by using the third fermented liquid n3 produced in the second fermentation line f2 and the third fermented medium m3 produced in the third medium tank 50. In the fourth fermentation line f4, the fifth fermented liquid n5 is produced in a fermentation environment without using any fermented medium. A fifth starter for the process $p_4 1$ of the fourth fermentation line f4 is only the fourth fermented liquid n4, and any new medium or fermented medium is not used.

Technical Feature of the Fourth Fermentation Line f4

Figure 16:
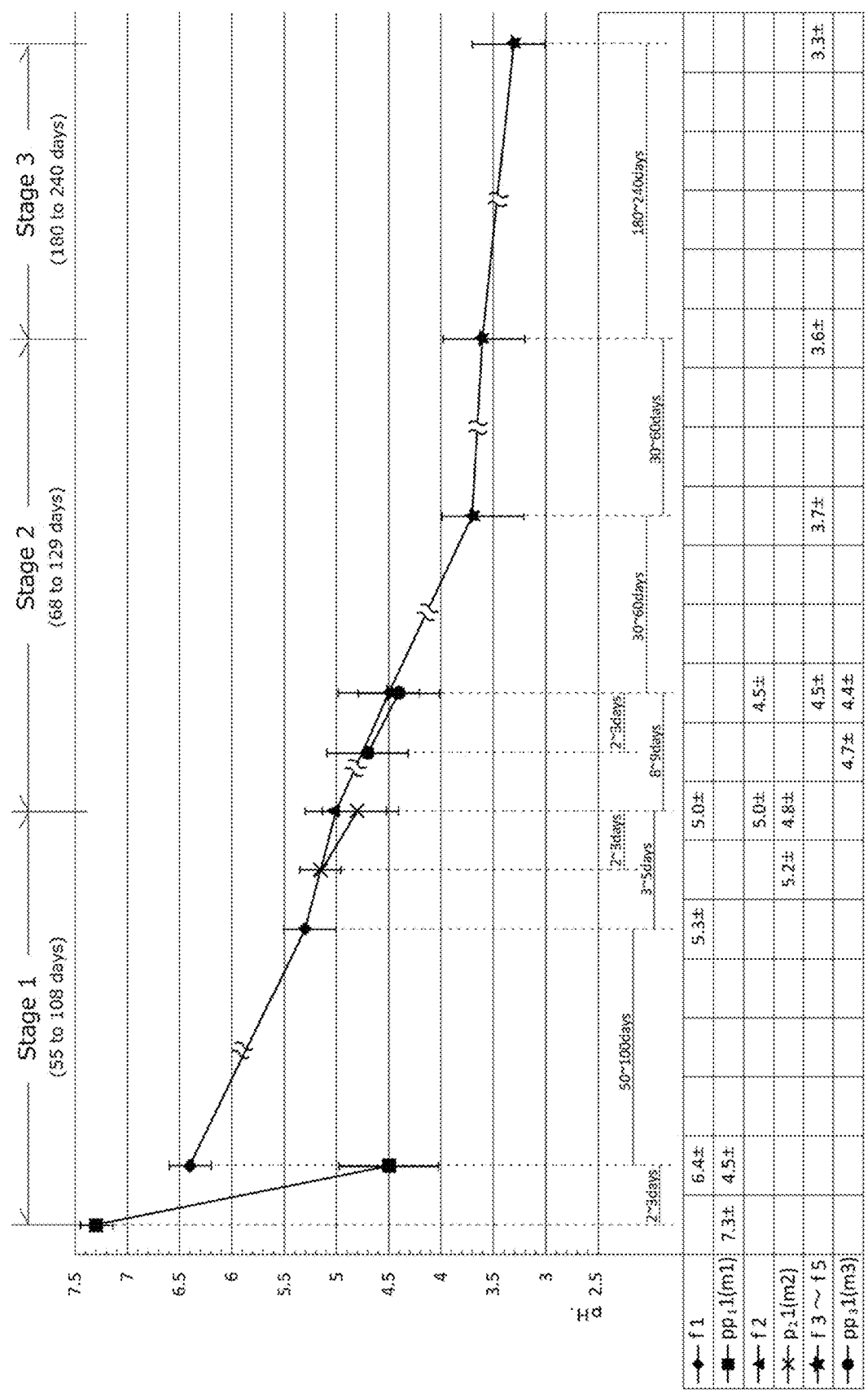
FIG. 16 is a graph and a table showing change of degree of fermentation in acidity of pH value, in which fermentation period required for the first to fifth fermentation lines and change of acidity of pH value of the first to sixth fermented liquid and the first to third fermented medium is divided into stages 1 to 3.

It seems that there is no significant change between an acidity of the fourth fermented liquid n4 of pH 3.7± and an acidity of the fifth fermented liquid n5 of pH 3.6±. However, as apparent from FIG. 16 representing a change of degree of fermentation of each process by acidity of pH value based on actual measurement, an acidity of the fifth fermented liquid n5 gradually increases during fermentation period of the fourth fermented liquid n4 for 30 to 60 days. It demonstrates that the fermentation progresses due to secretion and metabolism by the fermentation bacteria b1 contained in the fourth fermented liquid n4.

A technical intention for the fourth fermentation line f4 is referred. The inventors once considered in the course of their steady try-and-error practice for many years, that their intended method for producing a fermented liquid has been completed by the third fermentation line f3. At that time, the inventor did not suppose a technical necessity of the fourth fermentation line f4 following the third fermentation line f3. However, activity of secretion and metabolism of acidic materials by the fermentation bacteria b1 did not settle even at the end of the third fermentation line f3. Therefore, the inventors had repeatedly tried to stably produce the fourth fermented liquid n4 at the third fermentation line f3 by making various modifications such as heat sterilization of the fermentation bacteria b1. As a result, the inventors obtained a technical knowledge that the fermentation bacteria b1 including spore-forming fermentation bacteria can form spores and survive even under severe conditions such as high temperature, dryness, and poor nutritional status, and thus, it is difficult to treat such bacteria by heat sterilization etc.

Based on such technical knowledge, the inventors focused on a technical problem whether it is necessary to terminate the active secretion and metabolism of acidic materials by the fermentation bacteria b1 at the end of the third fermentation line f3, or continue it even taking longer time. Then the inventors got to find a technical value of secretion and metabolism of acidic materials by the fermentation bacteria b1 at or after the fourth fermentation line f4, to successfully achieve the present invention.

Details of a Fifth Fermentation Line f5

The fifth fermentation line f5 shown in FIGS. 1 [18] and [19] comprises:

a first process $p_51$ for once rapidly cooling the fifth fermented liquid n5 produced in the fifth fermentation tank 500 in the fourth fermentation line f4, and returning the rapidly cooled fifth fermented liquid n5 to an ordinary temperature condition, and a second process $p_52$ for fermenting the fifth fermented liquid n5 by the fermented bacteria b1 contained in the fifth fermentation liquid n5, under the ordinary temperature condition, to produce a sixth fermented liquid n6 of pH 3.3±corresponding to 1000 to 1050 L.

The sixth fermented liquid n6 is produced by fermenting the fifth fermented liquid n5 only by the fermented bacteria b1 contained in the fifth fermented liquid n5. It is similar manner as that of the fifth fermented liquid n5 produced by fermenting the fourth fermented liquid n4 only by the fermentation bacteria b1 contained in the fourth fermented liquid n4 in the fourth fermentation line f4. However, a fermentation environment for producing the sixth fermented liquid n6 is critically different from that for the fifth fermented liquid n5 in the following two respects. There exist technical features of the fifth fermentation line f5.

Technical Feature of the Fifth Fermentation Line f5

Figure 15:
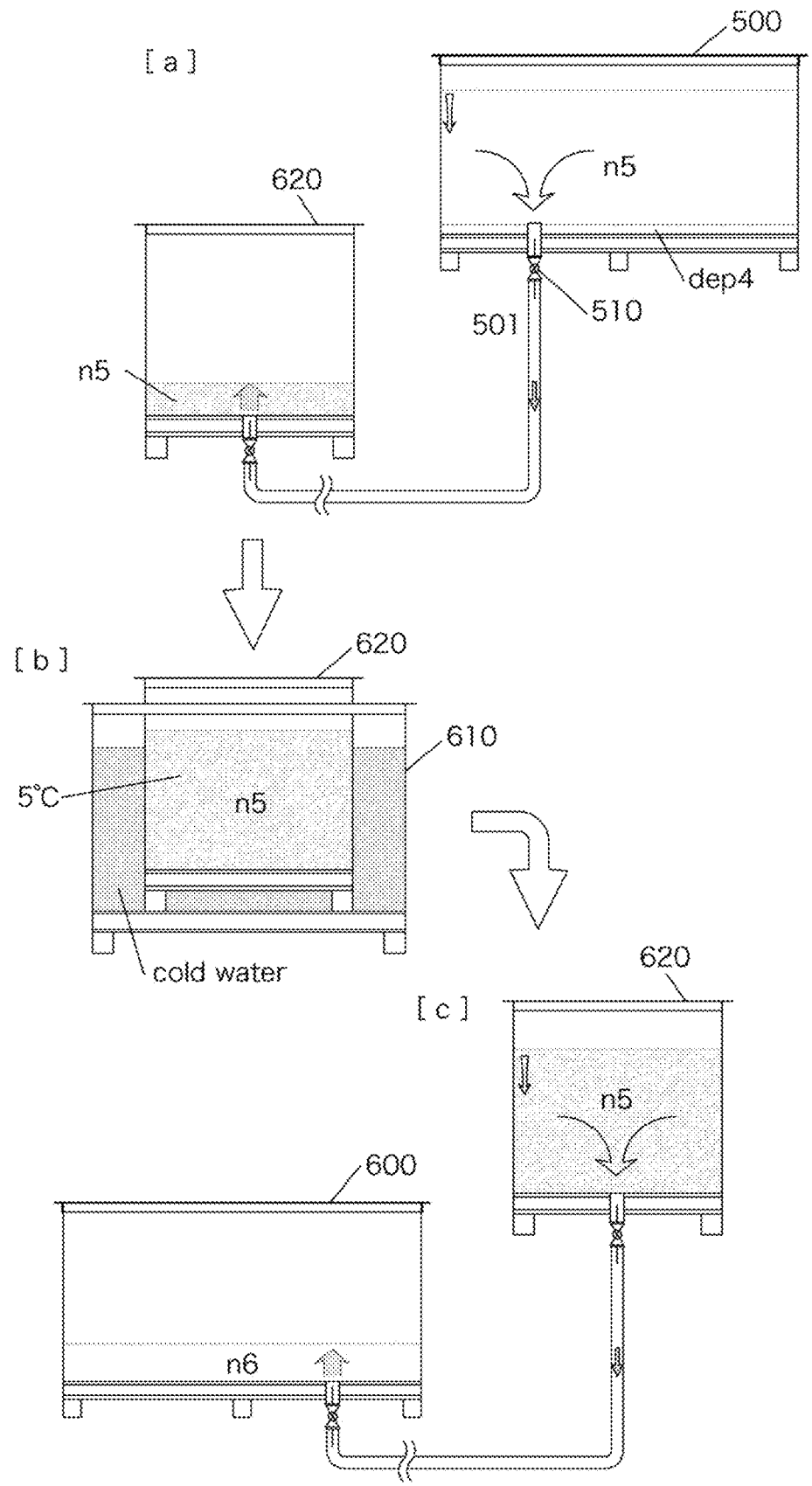
FIG. 15 is an enlarged schematic view showing a fifth fermentation line in which a fifth fermented liquid is transferred from a fifth fermentation tank to a reserve tank, and rapidly cooled by a cooling unit, a liquid temperature is controlled at a seasonal ordinary temperature, the cooled fifth fermented liquid is transferred to a sixth fermentation tank, a fermentation environment without using any fermented medium is established in the six fermentation tank, and the fifth fermented liquid is fermented only by fermentation bacteria in the fifth fermented liquid to produce a sixth fermented liquid.

The first technical feature of the fifth fermentation line f5 is shown in FIG. 15 [a]. It is a process for transferring the fifth fermented liquid n5 maintained under a fermentation condition at 37° C. to 40° C. in the fifth fermentation tank 500 into a reserve tank 620 provided for a cooling unit 610 of a sixth fermentation system s6.

A technical intention of the fifth fermented line f5 is shown in FIG. 15 [b] and exists in rapidly cooling the fifth fermented liquid n5 to a temperature at 4° C. to 5° C. or lower, at which activity of the fermentation bacteria b1 contained in the fifth fermented liquid n5 for secreting acidic material terminates. It means that the fermentation environment is shifted from an environment in which the fermentation bacteria b1 can easily activate the secretion and metabolism to an environment in which the fermentation bacteria b1 hardly activate the secretion and metabolism. In such condition, the fermentation bacteria b1 go into a dormant state and terminate its secretion and metabolism.

The fifth fermented liquid n5, containing the fermentation bacteria b1 terminating its secretion and metabolism by rapid cooling show in FIG. 15 [c] is transferred from the reserve tank 620 into a sixth fermentation tank 600, returned to an ordinary temperature condition according to the seasons, and fermented for 180 to 240 days under a fermentation environment at the ordinary temperature condition to gradually facilitate the activity of the fermentation bacteria b1 and activate the secretion and metabolism of acidic materials.

The second technical feature of the fifth fermentation line f5 is to create a fermentation environment at an ordinary temperature, specifically 5° C. to 28° C. according to the seasons, at which the fermentation bacteria b1 hardly act, rather than a fermentation condition at 37° C. to 40° C. at which the fermentation bacteria b1 can easily act, and perform long-term fermentation for 180 to 240 days (6 to 8 month) as shown in stage 3 of the FIG. 16, to facilitate the secretion and metabolism of acidic materials by the fermentation bacteria b1 while allowing metabolism activity settle down. Finally, the fermentation bacteria b1 terminate its secretion and metabolism and go into a dormant state, and the sixth fermented liquid n6 of pH 3.3 is produced in the sixth fermentation tank 600.

Function and Effect of the Invention

In principle, a first fermented liquid n1 of pH 5.3 produced according to the present invention is an initial fermented liquid for producing the final product, that is a sixth fermented liquid n6 of pH 3.3±. The first fermented liquid n1 is produced by fermenting an original solution θ for producing a fermented liquid having an acidity of pH 3 to 4 and comprising colloidal particles having a particle size not exceeding 50 nm and short-chain fatty acids, as a starter, for 50 to 100 days with maintaining fermentation condition at 37° C. to 40° C. as shown in stage 1 in FIG. 16. The original solution θ is a turbid liquid (a second preliminary fermented liquid pn2) prepared by mixing a soft water w, a fermented medium m1 of soybean paste, and a seed bacterial liquid b consisting of seven species of fermentation bacteria b1 comprising spore-forming fermentation bacteria (International Accession No. NITE BP-02945 to NITE BP-02951).

The reason why the turbid liquid (the second preliminary fermented liquid pn2) used as a starter for the first fermented liquid n1 is referred as an original solution θ is that the soft water w and the seed bacterial liquid b including the spore-forming fermented b1 are only used in producing the first fermented liquid n1. No soft water and seed bacterial liquid b are newly added in producing the second fermented liquid n2 to the six fermented liquid n6. Each of the processes for producing the second fermented liquid n2 to the six fermented liquid n6 establishes suitable fermentation environment to activate secretion and metabolism of acidic materials by the seven species of fermentation bacteria b1 including spore-forming fermentation bacteria contained in the first fermented liquid n1, and facilitate fermentation at each process to increase acidity of each fermented liquid.

The seed bacterial liquid consisting of seven species of fermentation bacteria b1 including spore-forming fermentation bacteria b1 is an essential component of the method for producing a fermented liquid having an acidity of pH 3 to 4 and comprising colloidal particles having a particle size not exceeding 50 nm and short-chain fatty acids according to the present invention. The seed bacterial liquid b consists of seven species of fermentation bacteria b1 including spore-forming fermentation bacteria b1 shown in FIG. 6 deposited to National Institute of Technology and Evaluation (NPMD), which is an International Depositary Authority (IDA) under the terms of the Budapest Treaty, under Accession Numbers. NITE P-02945, NITE P-02946, NITE P-02947, NITE P-02948, NITE P-02949, NITE P-02950, and NITE P-02951 on May 16, 2019, and have been transferred to the international deposit on Apr. 22, 2020 in the same institute under International Accession Numbers NITE BP-02945, NITE BP-02946, NITE BP-02947, NITE BP-02948, NITE BP-02949, NITE BP-02950, and NITE BP-02951. If the seed bacterial cannot be stably supplied, it is impossible to establish the present invention.

The inventors had repeated try-and-error in the course of their practice for many ears, and finally found and selected the seven species of fermented bacteria b1 shown in FIG. 6, including spore-forming fermentation bacteria producing organic acids including short-chain fatty acids, the short-chain fatty acids comprising butyric acid, propionic acid, and lactic acid, and successfully produced the seed bacterial liquid b stably producing the fermentation bacteria b1.

The seed bacterial liquid b is produced from the three layers formed in the two first fermentation tanks 100, including the sponge layer sp, the translucent intermediate layer, and the first deposition layer dep. More particularly, the supernatant sponge layer sp and the first deposition layer dep deposited at the bottom are removed from the first fermentation tanks 100 and mixed to form paste, which is the seed bacterial liquid b. Any of the three layers formed in the two first fermentation tanks 100 includes the seven species of the fermentation bacteria b1 including spore-forming bacteria configuring the seed bacterial liquid b.

The sponge layer sp and the first deposition layer dep excluding the translucent intermediate layer formed in the first fermentation tanks 100 becomes the seed bacterial liquid b, such that, when a charge amount for each of the first fermentation tanks 100 is assumed to be 900 L, ⅓ of the charge amount, that is 300 L of materials become a raw material for the seed bacterial liquid b, and when corresponding amount of paste-like seed bacterial liquid b prepared from the row material is used as a seed bacterial liquid b for the next charge, three layers having similar quality to the former charge is formed in the first fermentation tank 100 to produce the first fermented liquid n1 of pH 5.3±.

The paste-like seed bacterial liquid b may be cryopreserved. It may be confirmed from the fact that when necessary amount of the cryopreserved seed bacterial liquid b is returned to a fermentation condition at 37° C. to 40° C. and used as a paste-like seed bacterial liquid b for the next charge, three layers having similar quality to the former charge is formed in the first fermentation tank 100, and the first fermented liquid n1 of the translucent intermediate liquid layer thus formed always has an acidity of pH 5.3±

Although the paste-like seed bacterial liquid b may be preserved for long period in a large refrigerator, it may also be used for next fermentation line f1 as it is at the fermentation temperature, immediately after its 50 to 100 days fermentation. According to the method for producing a fermented liquid comprising short-chain fatty of the present invention, it takes at least 303 days (10 months) to 477 days (16 months) to produce the sixth fermented liquid n6 of the final product. However, continuous production may be performed at an interval of within about 100 days, for the period the production of the first fermented liquid n1 being completed. Basically, the sixth fermented liquid n6 of pH 3.3±, which is the final product according to the present invention, may be continuously produced at an interval of within 100 days.

Fermented Liquid Produce by the Invention

The fermented liquid produced according to the present invention is a fermented liquid produced by using a soft water w as a starter, a seed bacterial liquid b comprising seven species of fermentation bacteria b1 including spore-forming fermentation bacteria, and three kinds of fermented medium derived from natural materials including dried soybeans, dried plants consisting of three kinds of crude drugs of Jujube, *Lycium* Fruit, and Turmeric, and a honey material, and fermenting them.

For the final product of sixth fermented liquid n6 of pH 3.3± produced according to the present invention, following analysis is performed, and activities of acidic materials produced due to secretion and metabolism by the fermentation bacteria b1 during the fermentation of the first fermented liquid n1 to the sixth fermented liquid n6 is considered, and components configuring the fermented liquid produced according to the present invention are estimated.

(1) Analysis of acidity of pH value of the first fermented liquid n1 to the sixth fermented liquid n6;

(2) Particle size analysis of the sixth fermented liquid n6

(3) Analysis of sugar concentration of the fourth fermented liquid n4 to the sixth fermented liquid n6; and (4) Analysis of short-chain fatty acids for the second fermented liquid n2 to the sixth fermented liquid n6.

(1) Change of Acidity of pH Value of the First Fermented Liquid n1 to the Six Fermented Liquid n6:

The Inventors have daily produced the fermented medium and the fermented liquid according to the present invention, with monitoring the acidity of pH value of the fermented medium and the fermented liquid produced in each process described above. FIG. 16 is a graph showing average of the acidities between lots, which are always measured and monitored. The sign ± attached to each pH value represents variation on pH value (usually variation within 0.3) due to variations in temperature and humidity of the room where the measurements are performed, and also slight variation of timing of measurements. Such variations may always occur during the fermentation.

As shown in FIG. 16, change of acidity of the first fermentation line f1 is defined as stage 1. The stage 1 starts from pH 7.3± of the soft water w and includes acidities of the first fermented medium m1, the first fermented liquid n1 and the second fermented liquid n2. Fermentation period of the stage 1 may be at least about 55 days and at most about 108 days.

It should be noted that the first fermented medium m1 of pH 4.5± produced in the first fermentation tank 20, the seed bacterial liquid b, and large amount of the soft water w are put into the two first fermentation tanks 100 and stirred to produce a second preliminary fermented liquid pn2, which becomes an origin of, that is to say a starting point of the fermented liquid produced according to the present invention. After this point, any additional seed bacterial liquid b and soft water w will not be added again. Therefore, the second preliminary fermented liquid pn2 of pH 6.4± corresponds to an original solution θ for producing a sixth fermented liquid n6 of pH 3.3±, which is the final product produced according to the present invention. The second preliminary fermented liquid pn2 of pH 6.4± is fermented for 50 to 100 days at an appropriate fermentation temperature to produce a first fermented liquid n1 of pH 5.3±.

It should be also noted that the first fermented liquid n1 is fermented only by fermented bacteria b1 for 3 to 5 days at an appropriate fermentation temperature to produce a second fermented liquid of pH 5.0± in the second fermentation tank 200 at the last section of the stage 1. The last section overlaps with the process for producing a second fermented medium m2 of pH 4.8± by 2 or 3 days fermentation configuring the second fermentation line f2.

As shown in FIG. 16, change of acidity from the second fermentation line f2 to the fourth fermentation line f4 is defined as stage 2. The stage 2 starts from pH 5.0± of the second fermented liquid n2 of the second fermentation line f2 to pH 3.6± of the fifth fermented liquid n5 of the fourth fermentation line f4. The stage 2 also includes an acidity of the third fermented liquid n3 of pH 4.5± produced from the second fermented medium m2 and the second fermented liquid n2 as a starter in the second fermentation line f2, an acidity of the fourth fermented liquid n4 of pH 3.7±produced from the third fermented medium m3 and the third fermented liquid n3 as a starter in the third fermentation line f3, and an acidity of the fifth fermented liquid n5 of pH 3.6± produced from only the fourth fermented liquid n4 in the fourth fermentation line f4. Fermentation period of the stage 2 at an appropriate fermentation temperature may be at least about 68 days and at most about 129 days.

The following two change of the acidity should be noted. The first change is that, in the second fermentation line f2 using the second fermented medium m2 and the third fermentation line f3 using the third fermented medium m3, secretion and metabolism of acidic materials by the fermentation bacteria b1 is activated, and the acidity proceeds from pH 5.0± of the third fermented liquid n3 to pH 3.7± of the fourth fermented liquid n4. The second change is that, in the fourth fermentation line f4, only the fourth fermented liquid n4 is used as a starter and fermented for 30 to 60 days with maintaining fermentation condition at 37° C. to 40° C. to produce the fifth fermented liquid n5, an acidity is not so changed from pH 3.7± of the fourth fermented liquid n4 to pH 3.6± of the fifth fermented liquid n5.

Even at the end of the third fermentation line f3, an activity of the fermentation bacteria b1 for secretion and metabolism of acidic materials does not settle down. The inventors have utilized this fact, and found a technical value of the fermentation process of the fourth fermentation line f4, in which secretion and metabolism of acidic materials by the fermentation bacteria b1 may be facilitated even in mild fermentation, instead of terminating the active secretion and metabolism of acidic materials by the fermentation bacteria b1 at the end of the third fermentation line f3. Since the fermentation bacteria b1 including spore-forming fermentation bacteria can form spores and survive even under severe conditions such as high temperature, dryness, and poor nutritional status, it is difficult to treat such bacteria by heat sterilization etc., and the inventors have noticed the merit of facilitating the fermentation of the fourth fermented liquid n4 even it takes longer time.

As shown in FIG. 16, change of acidity of the fifth fermentation line f5 using the fifth fermented liquid n5 of pH 3.6± as a starter is defined as stage 3. The stage 3 is a process in which the fifth fermented liquid n5 maintained at appropriate fermentation condition at 37° C. to 40° C. is once rapidly cooled to 4° C. to 5° C. or lower, that is an environment in which the fermentation bacteria b1 hardly activate the secretion and metabolism, and then the environment is shifted to an ordinary temperature environment in which the fermentation bacteria b1 can moderately activate the secretion and metabolism, to ferment the fifth fermentation liquid n5 for 180 to 240 days at the ordinary temperature according to seasons. Of course, fermentation period of the stage 3 becomes long term, and may be at least about 180 days (six months) and at most about 240 (8 months).

It seems that the fifth fermentation line f5 is technically similar to a process for maturing the fifth fermented liquid n5 of pH 3.6±. However, in fact, the fifth fermentation line f5 is a process for facilitating secretion and metabolism of acidic materials by the fermentation bacteria b1, while allowing the metabolism activity settle down, and finally terminating secretion and metabolism of the fermentation bacteria b1 to produce a sixth fermented liquid n6 pH 3.3± in which the spore-forming fermentation bacteria b1 is in dormant state.

The change of acidity of pH value in each fermentation period is as follows. At a start of the practical fermentation in the two first fermentation tanks 100, the acidity is pH 6.4±, which is an acidity of the original solution θ, that is the second preliminary fermented liquid pn2. At the end of the first stage, the acidity proceeds to pH 5.0±. From the end of the first stage, the fermentation proceeds due to the secretion activity of the fermentation bacteria b1 included in the second fermented liquid n2. To the end of the second stage, the acidity proceeds to pH 3.6± with maintaining appropriate fermentation temperature at 37° C. to 40° C. During the process, even if the fermented liquid is contaminated with any non-spore-forming fermentation bacteria included in the seed bacterial liquid b or any aerobic bacteria, growth of such bacteria will be suppressed under the highly acidic environment, and killed bacteria will be deposited as a deposition layer at the bottom of each tank.

In the third stage of the long-term fermentation in the fermentation environment of ordinary temperature condition according to seasons, the fermentation proceeds with facilitating secretion activity of spore-forming fermentation bacteria included in the fermentation bacteria b1, and finally leads the secretin activity of the fermentation bacteria b1 including the spore-forming fermentation bacteria to almost the end of its activity. The fermentation no more proceeds and enters its stable state at acidity of pH 3.3±.

(2) Particle Size Analysis of the Sixth Fermented Liquid n6

The inventors have noted, based on their steady practical work, that the fermented liquid produced according to the present provides extremely high absorption ratio in vivo in mammalians. The inventors requested an analysis for configuration of the fermented liquid to certain professional laboratory and confirmed that the fermented liquid contains about 6.5% to 7.5% of colloidal particles. In particular, the inventors requested a particle size distribution analysis based on a cumulant analysis for following two kinds of fermented liquids produced according to the present invention to Industrial Technology Center of Gifu Prefectural Government and obtained results of the analysis.

Figure 17:
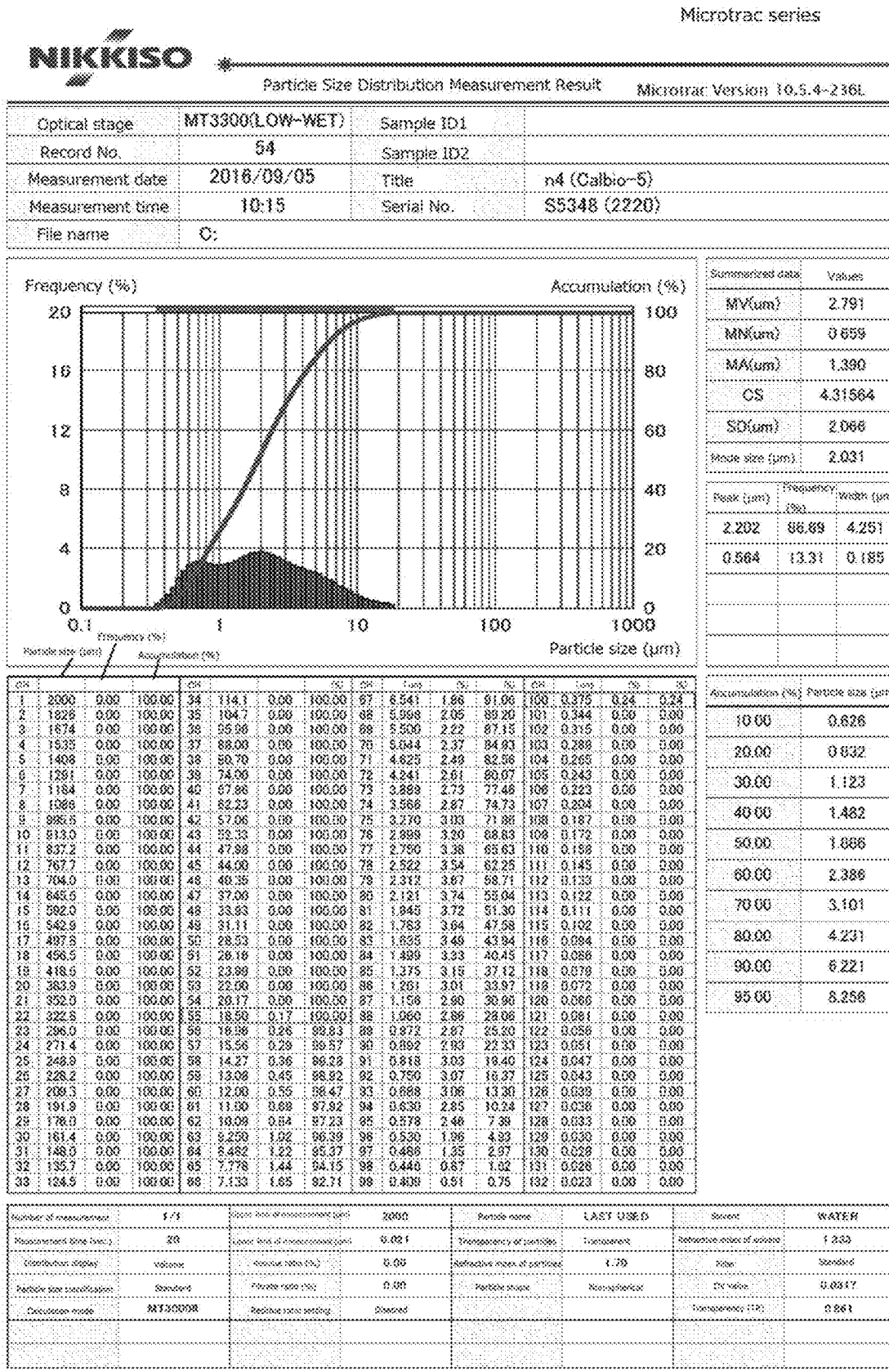
FIG. 17 is a graph and tables showing a result of cumulant analysis for measuring size of colloidal particles included in a fourth fermented liquid, using a heated/sterilized supernatant of the fourth fermented liquid as a sample.
Figure 18:
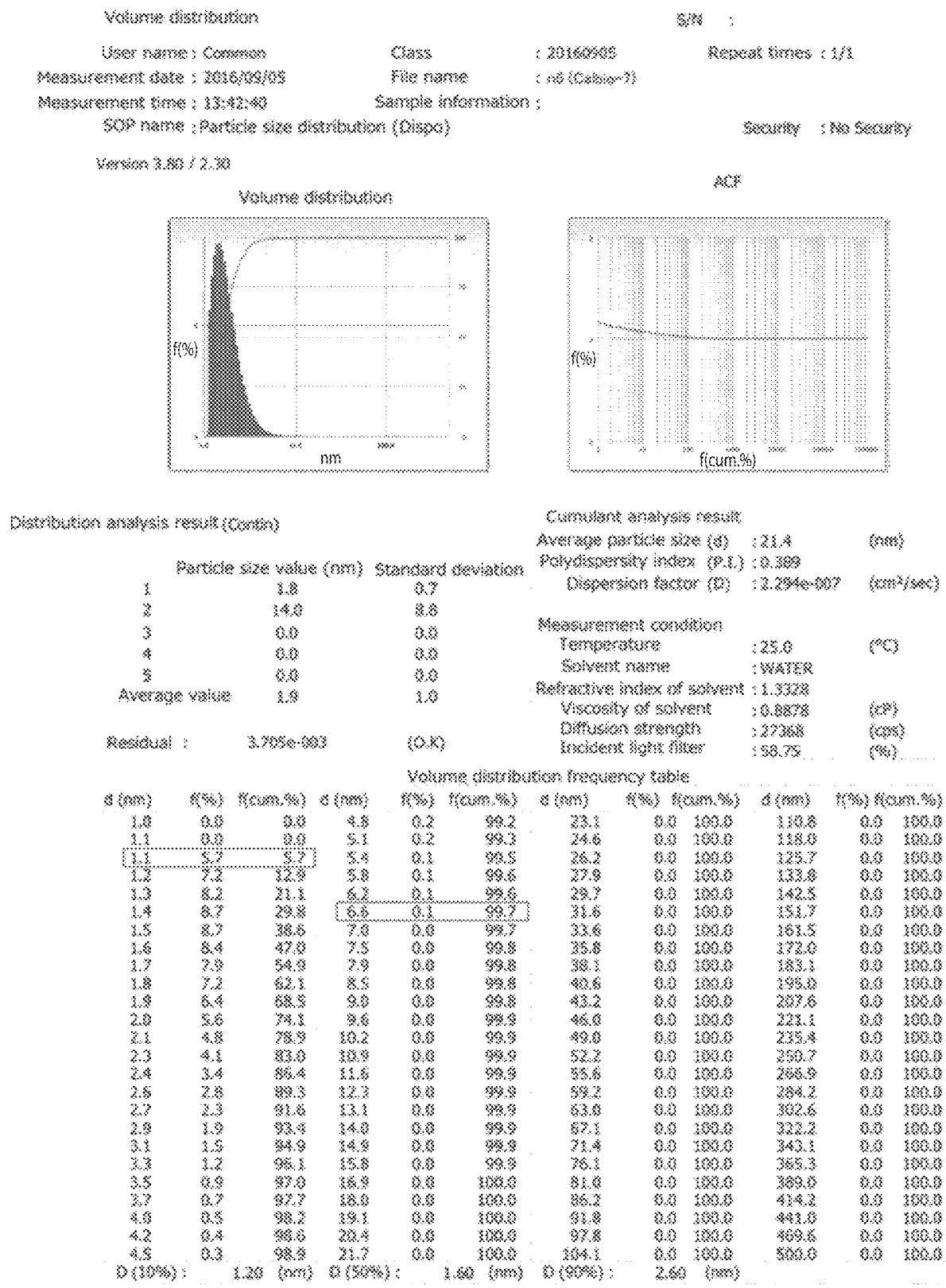
FIG. 18 is graphs and tables showing a result of cumulant analysis for measuring size of colloidal particles included in a sixth fermented liquid using a heated/sterilized supernatant of the sixth fermented liquid as a sample.

The two kinds of the fermented liquids produced according to the present invention are a fourth fermented liquid n4 of pH 3.7± and a sixth fermented liquid n6 of pH 3.3±. The particle size distribution analysis based on the cumulant analysis are prepared as follows. FIG. 17 shows a result of the cumulant analysis on the fourth fermented liquid n4. FIG. 18 shows a result of the cumulant analysis on the sixth fermented liquid n6. The cumulant analysis is a method for measuring colloidal particles contained at 6.5% to 7.5% in the fermented liquid.

The two kinds of samples provided to the Center are a first sample (Calbio-5) and a second sample (Calbio-7). The first sample (Calbio-5) was prepared by a process in which the fourth fermented liquid n4 of pH 3.7± produced from the fermentation using the fermentation media m1 to m3 was heat-sterilized, then cooled, and settled for one day, and 200 mL of sample from the supernatant of the settled fermented liquid was sterilized, and then divided into two 100 mL bottles. The second sample (Calbio-7) was prepared by a process in which the sixth fermented liquid n6 of pH 3.3± produced from the long-term fermentation of the fifth fermented liquid n5 of pH 3.6± for 180 days (6 months) to 240 days (8 months) in ordinary temperature fermentation environment, the fifth fermented liquid n5 being produced from the fermentation only by the fermentation bacteria b1 without using any fermented medium, was heat-sterilized, then cooled, and settled for one day, and 200 mL of sample from the supernatant of the settled fermented liquid was sterilized, and then divided into two 100 mL bottles.

In particular, the first sample (Calbio-5) is prepared as follows. The last fermented medium m3 (pH 4.4±) and a third fermented liquid n3 (pH 4.5±) as a starter is fermented for 30 to 60 days with maintaining fermentation condition at 37° C. to 40° C. to form a supernatant third surface layer, a third deposition layer dep3 containing deposition at a bottom layer, and a translucent third intermediate layer liquid between the third surface layer sf3 and the third deposition layer dep 3. The translucent third intermediate layer liquid is the fourth fermented liquid n4 of pH 3.7±, which becomes the first sample. The first sample corresponds to a fermented liquid produced in last fermentation process using fermented medium.

In particular, the second sample (Calbio-7) is prepared as follows. The fifth fermented liquid n5 of pH 3.6± is used as a starter, without using any medium or fermented medium, and the fifth fermented liquid n5 maintained at appropriate fermentation condition at 37° C. to 40° C. is once rapidly cooled to 4 to 5° C. or lower, that is an environment in which the fermentation bacteria b1 hardly activate the secretion and metabolism, and then the environment is shifted to an ordinary temperature environment in which the fermentation bacteria b1 can moderately activate the secretion and metabolism. The fermentation proceeds with facilitating secretion activity of spore-forming fermentation bacteria included in the fermentation bacteria b1, and finally leads the secretin activity of the fermentation bacteria b1 including the spore-forming fermentation bacteria to almost the end of the activity. The fermentation no more proceeds and provide the final product of the sixth fermented liquid n6 having an acidity of pH 3.3±. The sixth fermented liquid n6 becomes the second sample.

FIG. 17 shows particle size distribution of the fourth fermented liquid n4. FIG. 17 is a graph and table showing result of cumulant analysis for measuring size of colloidal particles contained at 6.5% to 7.5% in the fourth fermented liquid n4 after heat treatment/sterilization of the first sample. From the analytical result, it is found that the fourth fermented liquid n4 contains colloidal particles of micron unit in size. Specifically, the graph having vertical axis representing frequency y (%) and lateral axis representing particle size x (μm) in logarithm shows that the particle size of the colloidal particle in micron unit. In addition, specific numerical values can be grasped from the table showing numerical values in detail. The frequency is greater than 0% between CH No. 55 and CH No. 101. It is concluded that particle size x of the colloidal particles contained in the first sample is as follows:

x=0.375 μm (y=0.24%) to 18.5 μm (y=0.17%).

FIG. 18 shows particle size distribution of the sixth fermented liquid n6. FIG. 18 is a graph and table showing result of cumulant analysis for measuring size of colloidal particles contained at 6.5% to 7.5% in the sixth fermented liquid n6 after heat treatment/sterilization of the second sample. From the analytical result, it is found that the sixth fermented liquid n6 contains colloidal particles of nanometer unit in size. Specifically, the upper left graph having vertical axis representing frequency y (%) and lateral axis representing particle size x (nm) in logarithm shows that the particle size of the colloidal particle in nanometer unit. The graph shows that an average particle size is 21.4 nm. In addition, specific numerical values can be grasped from the table showing numerical values in detail. It is based on numerical values in the range in which the frequency is greater than 0%. It is concluded that particle size x of the colloidal particles contained in the second sample is as follows:

x=1.1 nm (y=5.7%) to 6.6 nm (y=0.1%).

Difference between FIGS. 17 and 18 is difference between micron unit and nanometer, that is $\frac{1}{1000}$ μm, unit. FIG. 17 represents particle distribution in micron unit, whereas FIG. 18 represents volume distribution frequency in nanometer unit.

The inventors once considered that their intended method for producing a fermented liquid has been completed by the third fermentation line f3 and tried to treat the fermentation bacteria b1 in order to terminate metabolism activity for secreting acidic materials. The inventors also noted that spore-forming fermentation bacteria included in the fermentation bacteria b1 can form spores and survive even under severe conditions, and thus it is difficult to treat such bacteria to terminate activity thereof. After that, the inventors, via the course of their try-and-error practice, utilize the metabolism activity of the fermentation bacteria b1 including active spore-forming fermentation bacteria and ferment the fourth fermented liquid n4 containing micron size particles as a starter for 30 to 60 days to produce the fifth fermented liquid n5 of pH 3.6±.

The inventors fermented the fifth fermented liquid n5 as a last starter for long term of 180 days (6 months) to 240 days (8 months) at a fermentation environment at an ordinary temperature to gradually settle down secretion activity of the fermentation bacteria b1, and consequently, gradually increase an acidity due to natural fermentation by the fermentation bacteria b1 including spore-forming fermentation bacteria, to finally succeed in stabilizing the acidity at pH 3.3±. Furthermore, unexpected result can be achieved in that the sixth fermented liquid n6 containing colloidal particles of nanometer unit in size can be obtained. It goes without saying that when such fermented liquids are used as fermentation foods, significant difference in an absorption ratio in vivo occurs between the fermented liquid containing colloidal particles of micron unit in size and the fermented liquid containing colloidal particles of nanometer unit in size.

Second analysis of performance of the fourth fermented liquid n4 and the sixth fermented liquid n6 is to measure amount of sugar contained in each fermentation liquid. The inventors produced the third fermented medium m3 from the honey material pm3, mixed the third fermented medium m3 with the third fermented liquid n3 corresponding twenty times as much as the fermented medium m3, stirred them to establish an fermentation environment having a sugar concentration of 3 to 5%, which is the best fermentation environment for secretion activity of the fermentation bacteria b1, fermented them for 30 to 60 days with maintaining fermentation condition at 37° C. to 40° C. to further facilitate secretion and metabolism of acidic materials by the fermentation bacteria b1, and succeeded in producing the fourth fermented liquid n4 of pH 3.7±.

(3) Analysis of Sugar Concentration of the Fourth Fermented Liquid n4 to the Sixth Fermented Liquid n6

FIG. 19 show results of measurement of sugar amount c1 per 100 mL of fourth fermented liquid n4, sugar amount c2 per 100 mL of fifth fermented liquid n5, and sugar amount c3 per 100 mL of sixth fermented liquid n6. Specifically, the results are as follows:

c1=3.39 g/100 mL
c2=2.88 g/100 mL
c3=1.19 g/100 mL

The inventors conceived the third fermentation line f3 based on their steady try-and-error practice for many years, and have repeated try-and error, to enhance growth and ability of secretion and metabolism of the fermentation bacteria b1 by providing certain amount of fermented medium obtained by fermenting honey materials to the fermentation bacteria b1, and achieve continuous fermentation due to further secretion and metabolism of acidic materials.

The inventors found that a certain sugar amount for maintaining the ability of the secretion and metabolism of the fermented bacteria b1 may correspond to a honey material pm3 corresponding to 3 to 5% of the third fermented liquid n3, based on a degree of water activity. The honey material pm3 are mixed and stirred with the third fermented liquid n3 four times as much as the amount of the honey material pm3 to produce a preliminary fermented medium pfm3. The preliminary fermented medium pfm3 are fermented for 2 or 3 days with maintaining fermentation condition at 37° C. to 40° C. to produce a third fermented medium m3. Further, the third fermented medium m3 are mixed and stirred with a third fermented liquid n3 twenty times as much as the amount of the third fermented medium m3, and fermented for 30 to 60 days with maintaining fermentation condition at 37° C. to 40° C. to facilitate the fermentation due to the secretion and metabolism of acidic material by fermentation bacteria b1 In this manner, the inventors successfully produced the fourth fermented liquid n4 of pH 3.7±. This is the third fermentation line f3.

FIGS. 13 and 14 shows the technical feature of providing a certain amount of the fermented medium, which is a fermented sugar, to the third fermented liquid n3 to enhance growth and ability of secretion and metabolism of the fermentation bacteria b1. FIG. 13 shows photographs A and B showing a result of comparative test for samples A and B of fermentation models of the fourth fermentation liquid n4. The sample A is a fermented liquid A (corresponds to a fourth fermented liquid n4) prepared by mixing a third fermented medium m3 produced by preliminarily fermenting a honey material pm3 corresponding to 5% of a third fermented liquid n3, with the third fermented liquid n3 twenty times as much as the volume of the third fermented medium m3 such that total amount becomes 1 L, and fermenting them. The sample B is a fermented liquid B prepared may mixing a honey material pm3 as it is with a third fermented liquid n3 twenty times as much as the volume of the third medium pm3 such that total amount becomes 1 L, and fermenting them.

For the sample A, three layers are formed in a test container, wherein the tree layers include a translucent third intermediate layer liquid between a third surface layer sf3 and a third deposition layer dep 3, and translucent third intermediate layer liquid corresponds to the fourth fermented liquid n4. For the sample B, it is confirmed from photograph B that a surface layer sf3 is formed in a test container, but much thinner than that of the sample A. It reveals that the fermentation of the sample B due to secretion and metabolism of acidic materials by the fermentation bacteria b1 is less active than that of the sample A. This is confirmed from FIG. 14.

FIG. 14 demonstrates that the fermentation bacteria b1 in the fermented liquid A secretes acidic materials more active. The inventors have devised modifications to activate the fermentation bacteria b1 so as to enhance the secretion and metabolism of acidic material, by using the third fermented medium m3 produced by preliminarily fermenting the honey material pm3 for producing the fourth fermented liquid n4, instead of using the honey material pm3 as it is, to change the fermenting environment for the fermented bacteria b1.

The inventors requested sugar concentration analysis on the fourth to sixth fermented liquid samples by Somogyi modified method to Japan Food Research Laboratories. The fourth fermented liquid n4 of pH 3.7± was produced as described above. The fifth fermented liquid n5 of pH 3.6± was produced by fermenting the fourth fermented liquid n4 of pH 3.7± as a starter, only by the fermentation bacteria b1 without using any fermented medium. The sixth fermented liquid n6 of pH 3.3± was produced by fermenting the fifth fermented liquid n5 of pH 3.6± as a starter for long term of 180 days (6 months) to 240 days (8 months), only by the fermented bacteria b1 without using any fermented medium. All fermented liquids were heat-sterilized, then cooled, and settled for one day. Each of 200 mL of supernatant of the settled fermented liquids was sterilized, then divided into two 100 mL bottles, and provided to the Japan Food Research Laboratories.

The result of the analysis is as described above. The fermented liquid n4 of pH 3.7± was prepared by using the honey material pm3 corresponding to 5% of the third fermented liquid n3, and thus 5 g of sugar is added per 100 mL of the third fermented liquid n3. The sugar amount was decreased to finally become 3.93 g per 100 mL in the fourth fermented liquid n4 after the fermentation. It may be a result of depletion of sugar due to the activity of the fermentation bacteria b1. The sugar amount of 2.88 g in the fifth fermented liquid n5 and 1.19 g in the sixth fermented liquid n6 may also be the result of the depletion of the sugar due to the activity of the fermentation bacteria b1.

From the result, it may be understood that the sugar concentration of the fourth fermented liquid n4 is nearly 4%, and the metabolism activity of the fermentation bacteria b1 of secreting acidic materials hardly settles down in the third fermentation line f3, and also it is difficult to perform various treatment such as heat-sterilization to the fermentation bacteria b1.

Also, the sugar concentration of the fifth fermented liquid n5 of 2.88 g/100 mL and the sixth fermented liquid n6 of 1.19 g/100 mL indicate that the sugar concentration may be decreased so as to facilitate the active secretion and metabolism by the fermentation bacteria b1 while readily leading the activity to settle down by long-term fermentation without performing severe treatment such as heat-sterilization.

The process of the forth fermentation line f4 for producing the fifth fermented liquid by 30 to 60 days fermentation and the process of the fifth fermentation lane f 5 for producing the sixth fermented liquid n6 by the long-term 180 days (6 months) to 240 days (8 months) fermentation are both the process for facilitating secretion activity of spore-forming fermentation bacteria contained in the fermentation bacteria b1 to allowing them forming spore, and finally provide an environment which is nearly dormant state for the fermentation bacteria b1.

(4) Analysis of Short-Chain Fatty Acids for the Second Fermented Liquid n2 to the Sixth Fermented Liquid n6

Constituents of the present invention are acidic materials produced by the secretion activity of the seven species of fermentation bacteria b1 in the seed bacterial liquid b consisting of the fermentation bacteria (International Accession No. NITE BP-02945 to NITE BP-02951) including spore-forming *Clostridium* bacteria maintained under low temperature state. As seen from acidic materials shown in FIG. 20, the acidic materials are short-chain fatty acids including butyric acid, which forming intestinal ecology in vivo. It may be obvious from comparative analysis of short-chain fatty acids contained in the second fermented liquid n2 to the sixth fermented liquid n6.

The second fermented liquid n2 is the final product of the first fermentation line f1. In the first fermentation line f1, the first fermented liquid n1 produced in the second process $p_1 2$ is transferred from two first fermentation tanks 100 into one second fermentation tank 200 as shown in schematic diagram of FIG. 4, and a fermentation environment without using any fermented medium is established, and the first fermented liquid n1 is fermented for 3 to 5 days with maintaining fermentation condition at 37° C. to 40° C. only by the fermentation bacteria b1 contained in the first fermented liquid n1 of pH 5.3± to produce the second fermented liquid n2 of pH 5.0±. The third fermented liquid n3 to the sixth fermented liquid n6 are respective final products of the second fermentation line f2 to the fifth fermentation line f5.

Change of each final product of fermentation lines was observed, for acidic materials produced by the secretion activity of the seven species of fermentation bacteria b1 in the seed bacterial liquid b consisting of the fermentation bacteria (International Accession No. NITE BP-02945 to NITE BP-02951) including spore-forming *Clostridium* bacteria maintained under low temperature state.

Samples are as follows:
(1) the second fermented liquid n2 of pH 5.0± produced in the first fermentation line f1 for 55 to 108 days;
(2) the third fermented liquid 3 of pH 4.5± produced by fermenting the second fermented liquid n2 as a starter for 8 to 9 days;
(3) the fourth fermented liquid n4 of pH 3.7± produced by fermenting the third fermented liquid n3 as a starter for 30 to 60 days;
(4) the fifth fermented liquid n5 of pH 3.6± produced by fermenting the fourth fermented liquid n4 as a starter for 30 to 60 days; and
(5) the sixth fermented liquid n6 of pH 3.3± produced by fermenting the fifth fermented liquid n5 as a starter for 180 to 240 days.

Each of the second fermented liquid (1) to the fifth fermented liquid n5 (4) is the final product of the fermentation with maintaining fermentation condition at 37° C. to 40° C. The sixth fermented liquid n6 (5) is the final product of the fermentation at an ordinary temperature fermentation environment different from that of (1) to (4).

All fermented liquids (1) to (5) were heat-sterilized, then cooled, and settled for one day. Each of 200 mL of supernatant of the settled fermented liquids was sterilized, then divided into two 100 mL bottles, and provided to the Japan Food Research Laboratories for analyzing short-chain fatty acids by high performance liquid chromatography (HPLC) The result of measurement of contents of short-chain fatty acids, including lactic acid, propionic acid, and butyric acid, contained in the second fermented liquid n2 to the sixth fermented liquid n6 was obtained.

The results are shown in FIG. 20, and specifically as follows. (unit: /100 mL)

| Kind of short-chain fatty acid | Lactic acid | Propionic acid | butyric acid |
|---|---|---|---|
| 2nd fermented liquid n2 | ND (0 g) | 0.01 g | 0.18 g |
| 3rd fermented liquid n3 | 0.08 g | 0.01 g | 0.30 g |
| 4th fermented liquid n4 | 0.20 g | 0.02 g | 0.54 g |
| 5th fermented liquid n5 | 0.13 g | 0.02 g | 0.59 g |
| 6th fermented liquid n6 | 0.21 g | 0.02 g | 0.58 g |

For the second fermented liquid n2, no lactic acid is detected, and 0.01 g/100 mL of propionic acid and 0.08 g/100 mL of butyric acid are detected. The fermented liquid produced according to the present invention is produced by fermenting natural materials. Among the short-chain acid, the contents of the butyric acid is 0.30 g/100 mL in the third fermented liquid n3, 0.54 g/100 mL in the fourth fermented liquid n4, and almost reaching 0.60 g/100 mL in the fifth fermented liquid n5 and the sixth fermented liquid n6 produced only by the fermentation bacteria b1 contained in the fourth fermented liquid n4 and the fifth fermented liquid n5 without using any medium or fermented medium. Evaluation of such high butyric acid contents will be made by basic research in future, but the content of 6 g of butyric acid per 1000 mL may be sufficiently expected to have considerable effect on at least generation of regulatory T-cells, related to anti-inflammation effect, improvement of bone strength, anti-obesity effect, anticancer effect, etc.

Finally, the sixth fermented liquid n6 is filtered through 0.2 μm-mesh filter to extract accumulated fermentation metabolite including short-chain fatty acid. The extract is used as a natural fermentation material for various application including a raw material for food or foodstuff itself. An example of the applicability of the fermented liquid is shown below.

Action and Effect of the Fermented Liquid Produced According to the Present Invention The fermented liquid produced according to the present invention is a fermented liquid made from natural material, having an acidity of pH 3 to 4, comprising colloidal particles having a particle size not exceeding 50 nm and 5 g or more butyric acid per 1000 mL of the fermented liquid. Routine ingestion of the fermented liquid may activate calcium metabolism in living body, and significantly enhance bone strength and bone metabolism. It was confirmed by several tests such as "Test for calcium absorption evaluation by everted gut sac method" conducted by Tennen Sozai Tansaku Kenkyusyo, Inc., and a detailed test using osteoporosis-model mice for testing functional foods conducted by Department of Physiology, Gifu University School of Medicine.

Tennen Sozai Tansaku Kenkyusyo, Inc. (Representative Director: AOYAMA, Yoshiko) presented report of "Test for calcium absorption evaluation by everted gut sac method" on November 2015. The test was conducted on test animals, which were male rats of SD strain, and fed with pellet CRF-1 (Oriental Yeast Co., Ltd.) and distilled water from water bottles in free-feeding during preliminary keeping period. Test sample was the sixth fermented liquid n6 (Calbio-7).

Three test groups of test animals were set as follows:
Control group including 5 animals (9 gut sacs; 3 gut sacs for each of reactions for 30, 60, and 90 min.);
Group added with 0.1% of the sixth fermented liquid n6 (Calbio-7) including 5 animals (9 gut sacs; 3 gut sacs for each of reactions for 30, 60, and 90 min); and
Group added with 0.5% of the sixth fermented liquid n6 (Calbio-7) including 5 animals (9 gut sacs; 3 gut sacs for each of reactions for 30, 60, and 90 min.)

The test items and method were as follows:
(1) Preliminary keeping period was set to be 6 days. Animals had been preliminarily kept and conditioned with free-feeding of pellet CRF-1 before an actual keeping period starts.
(2) Then, absorption test with the everted gut sac method was conducted. The test includes:
a) preparing inside solution and outside solution, consisting of preparation of reagents and preparation of the inside and outside solutions; b) preparing everted gut sacs; c) subjecting the everted gut sacs to reaction for 30, 60, and 90 minutes; d) performing calcium measurement; and e) performing statistical analysis, wherein a test result was determined to be significant when the level of significance was 5% or lower. The experimental result of the calcium absorption test with the everted gut sac method is shown in FIG. 21.

FIG. 21 shows the experimental result of the calcium absorption test by the everted gut sac method, wherein male SD rats were used as model animals and the test material Calbio-7 was administered. Upper graph shows "calcium increment amount" and lower graph show "calcium absorption rate". According to comparison and consideration of the result for the calcium absorption by the everted gut sac method, the upper graph shows that the Calbio-7-added groups present significantly higher values in the calcium increment amount than that of the control group on each calcium source. The lower graph shows that the Calbio-7-added groups present higher values in the calcium absorption rate than that of the control group on calcium lactate source. It also shows that the 0.5% of Calbio-7-added group presents significantly higher values in the calcium absorption rate than that of the control group on both calcium citrate and calcium carbonate sources.

In summarizing the test result, Calbio-7-added group of each concentrations presents significantly higher value in the calcium increment amount than that of the control group at all reaction period, and transfer from the outside solution to the inside solution is highest at a reaction period of 30 min. On the other hand, Calbio-7-added group of each concentration also present significantly higher values in calcium absorption ratio than that of the control group at all reaction period, and the absorption ratio is highest at a reaction period of 60 min.

The test using osteoporosis-model mice was performed at the Department of Physiology, Gifu University School of Medicine, and the detailed report of the test was made by Chikara ABE at the Department of Physiology and sealed by Shinya MINATOGUCHI, a director of the Gifu University School of Medicine on February 2017. This test was performed for an effect of administration of test material Calbio-7 on a bone mineral density and a bone metabolism marker using osteoporosis-model mice, considering the preceding test report of the "Test for calcium absorption evaluation by everted gut sac method" on November 2015. A part of the contents of this test are extracted and presented below.

Problems to be tested is related to an effect of administration of test materials on a bone mineral density and a bone metabolism marker using osteoporosis-model mice. An overview of the test is that the test materials were administered continuously for eight weeks to osteoporosis-model mice in estrogen-deficiency state caused by ovariectomy (OVX) to the ovaries both sides, and effects of the administration on prevention of osteoporosis were evaluated.

The experimental method is as follows:

As experimental animals, twelve-weeks-old rats C57BL/6 (female, n=24) were used. Four test groups were used, and each group included six rat, including normal Sham rats and ovariectomized OVX rats as follows:

Sham+water (SWW), n=6;
Sham+Calbio-7 (0.5 mL/day) (SCC), n=6;
OVX+water (OWW), n=6; and
OVX+Calbio-7 (0.5 mL/day) (OCC), n=6.
Administration plan of the test material was as follows

TABLE 1

| Week | 11 | 12 | 13 | 14 | 15 | 16 | 17 | 18 | 19 | 20 |
|---|---|---|---|---|---|---|---|---|---|---|
| SWW | water | water | water | water | water | water | water | water | water | sampling |
| SCC | water | C7 | C7 | C7 | C7 | C7 | C7 | C7 | C7 | |
| OWW | water | water | water | water | water | water | water | water | water | |
| OCC | water | C7 | C7 | C7 | C7 | C7 | C7 | C7 | C7 | |

C7: test material Calbio-7 (sixth fermented liquid n6)
C7 was adjusted based on data of amount of drinking water, such that 0.5 mL was taken per day.

Test items relate to bone structure, and include acquiring data of the ratio of Gla-Osteocalcin, i.e., bone formation marker, to Glu-Osteocalcin, i.e., a bone resorption marker in blood, as well as acquiring data from tests for degree of effect on bone weight, bone strength and bone mineral density.

Figure 22:
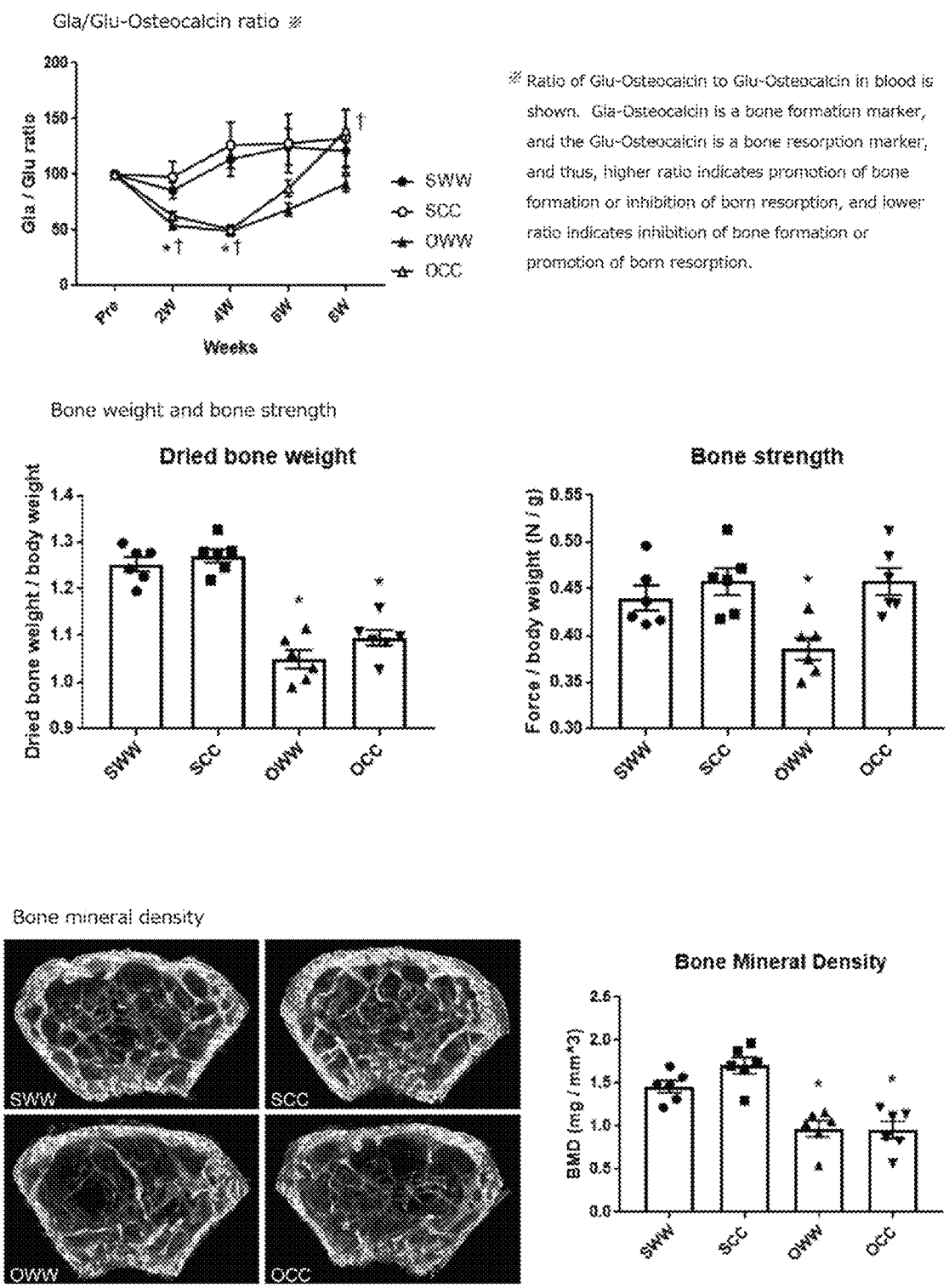
FIG. 22 is graphs and photograph of bone density based on results of test for degree of effect on "Gla/Glu-Osteocalcin ratio" and "bone weight and bone strength, and bone density" using osteoporosis-model mice in estrogen-deficiency state caused by ovariectomy to both ovaries, and administering a test material (sixth fermented liquid).

FIG. 22 shows test results of the Gla/Glu-Osteocalcin ratio and test results of the degree of the effect on the bone weight, the bone strength, and the bone mineral density, using osteoporosis-model mice in estrogen deficiency state.

FIG. 22 shows effect of the administration of test materials, using the osteoporosis-model mice in estrogen-deficiency state caused by ovariectomy (OVX) to the ovaries both sides, on the ratio of Gla/Glu-Osteocalcin for the test groups, and bar graphs and photograph show effects on "bone weight and bone strength", and effects on "bone mineral density". Here, the Gla-Osteocalcin is a bone formation marker, and the Glu-Osteocalcin is a bone resorption marker, and thus, higher ratio indicates promotion of bone formation or inhibition of born resorption, and lower ratio indicates inhibition of bone formation or promotion of born resorption.

The left graph of FIG. 22 showing effect on "bone weight and bone strength" shows dried bone weight of femur (corrected with body weight). The right graph shows bone strength of femur (corrected with body weight) obtained by three-point bending test. Ovariectomy (OVX) caused reduction of the dried bone weight. Although no recovery of the reduced bone weight by the ingestion of Calbio-7 may be observed, the bone strength test shows that the ingestion of Calbio-7 could significantly prevent a reduction of the bone strength caused by OVX.

The left view of FIG. 22 relating to the "bone mineral density" shows typical examples of bone mass of spongy bone in femur. The right graph shows bone mineral density of the spongy bone (trabecular weight of spongy bone/cavity volume of spongy bone.) Significant reduction of the spongy bone trabeculae density by Ovariectomy (OVX) may be observed. No recovery of this value by the ingesting Calbio-7 may be observed. On the other hand, SCC group presents not significant but high value.

The foregoing is an extracted part of this report, and at the conclusion section of the report, the experimenter indicates evaluation results (1) to (3) as follow.

(1) In this experiment, the ingestion of Calbio-7 improved the bone strength in OCC group. However, no difference was found between OCC and OWW groups in qualitative evaluation of the dried bone weight and the spongy bone trabeculae, and thus some factors other than bone structure (trabecular density) may be considered to exert an effect on recovery of the bone strength. Regarding states of bone formation and bone resorption, there was a tendency that OCC group had higher value than that of OWW group at eighth week. Some factor may be considered to activate calcium metabolism.

(2) Variation of female hormone balance due to Ovariectomy (OVX) may extremely strong, and thus calcium amount contained in normal feed may supposed to be insufficient to supplement consumed amount of calcium. The result of the test for calcium absorption effect using the everted gut suck method shows that the increment amount and the absorption rate of calcium are higher than that of control group on every calcium sources.

(3) Considering (1) and (2) and the fact that the ingestion of Calbio-7 can significantly prevent the bone strength reduction caused by Ovariectomy (OVX), it may be desirable to perform additional studies for improving variations of numerical values such as increased bone resorption caused by OVX, by using, in particular, calcium lactate-added feeds, since the calcium lactate provided pronounce increment in the absorption and increment rate (with reference to "Test for calcium absorption evaluation by everted gut sac method" on November 2015), For functions of the fermented liquid made from natural material, having an acidity of pH 3 to 4, comprising colloidal particles having a particle size not exceeding 50 nm and 5 g or more butyric acid per 1000 mL of the fermented liquid according to the present invention to exert effects on living bodies, (1) test for effect of Calbio-7 ingestion on intestinal bacterial flora, and (2) test for anti-cancer effect were conducted on May 2014 by Itech Lab Inc. (a parson in charge of experiment is Masaki MATSUURA, and report writer is Shin NAKAMURA), at Kaizu city, Gifu prefecture, and reported. The test sample for these tests were also Calbio-7.

In the test (1), C57BL/6 mice (male ♂, 7-weeks old) were divided into a control group and Calbio-7-administered group (n=10), and water for injection was orally administered to the control group and Calbio-7 was orally administered to the Calbio-7-administered group at 0.5 mL/body for 28 days continuously.

In the test (1), after the administration period had completed, contents of colon were collected and analyzed or frozen and stored. Bacterial DNA was then extracted from the contents of colon using a kit dedicated for extracting bacterial nucleic acid. Concentrations of the resultant DNA were measured, and their purities were checked. When DNAs were extracted, equal amounts of samples from three or four individuals in the same group were pooled, and DNA was extracted from the pools. The bacterial DNA was quantified using primers specific for each of *Lactobacillus*, *Bifidobacterium* and *Clostridium*, and a universal primer to calculate relative copy number of each bacterial DNA, as well as each ratio to that of the control group.

Figure 23:
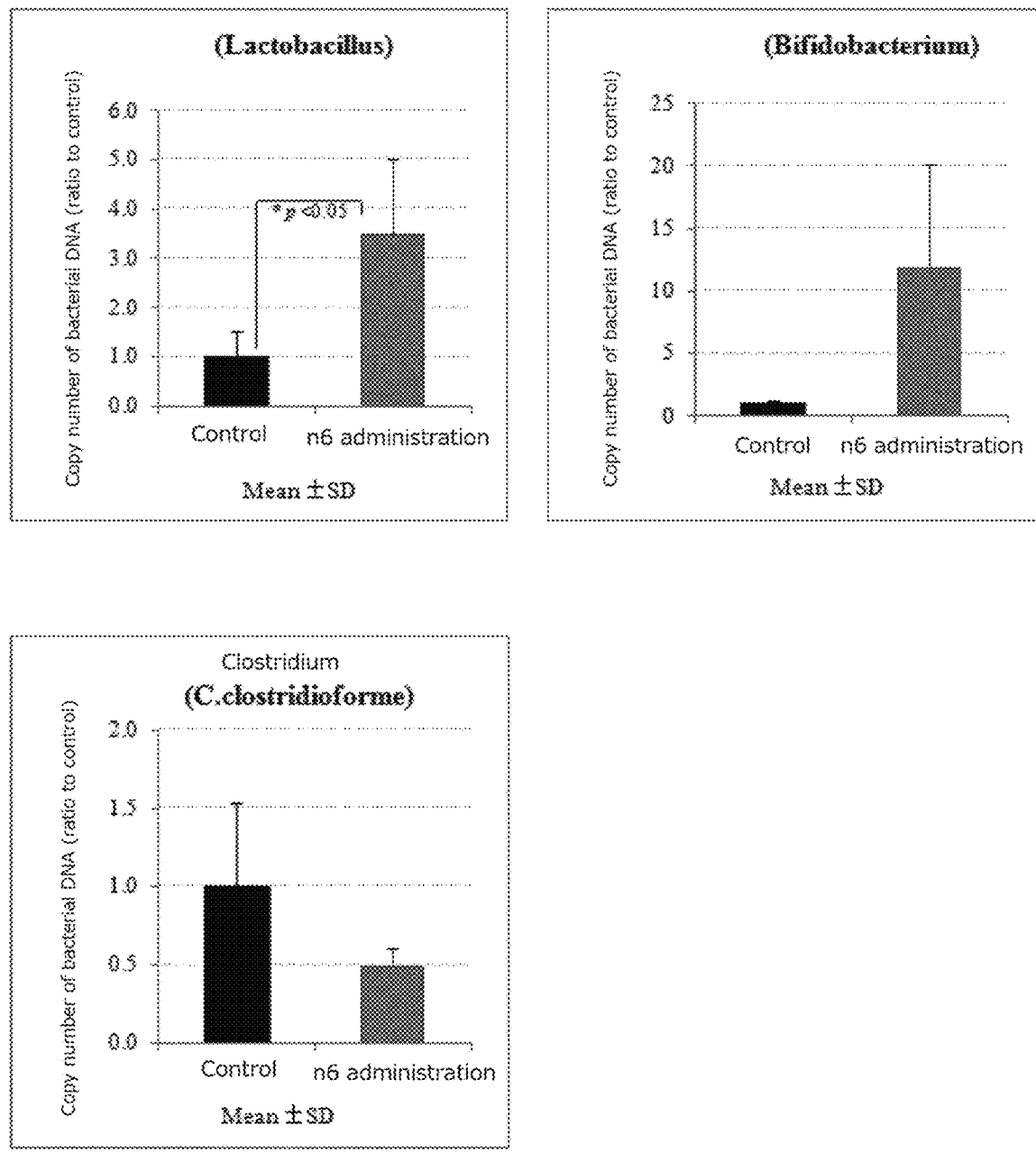
FIG. 23 shows a result of test for effects on intestinal bacterial flora, wherein the test is performed at Itech Lab Inc. (a parson in charge of experiment is Masaki MATSUURA) by orally administering a test material (sixth fermented liquid) to administered group of C57BL/6 mice (male, seven-weeks-old) for 28 days continuously, collecting contents of colon of the animals from the administered-group and control group, and extracting bacterial DNA from the contents of colon.

Results of the test (1) as to effects of the ingestion of Calbio-7 on intestinal bacterial flora are shown in FIG. 23. FIG. 23 shows the test results as to the effects on intestinal bacterial flora when the fermented liquid (Calbio-7) produced according to the present invention was administered Upper graphs of FIG. 23 represent that intestinal friendly, or "good" bacteria including at least *Lactobacillus* and *Bifidobacterium* are doubled in the intestinal bacterial flora. Lower graph of FIG. 23 represents that intestinal unfriendly, or "bad" bacteria including at least *Clostridium perfringens* (*Welch bacillus*) are halved in the intestinal.

Figure 24:
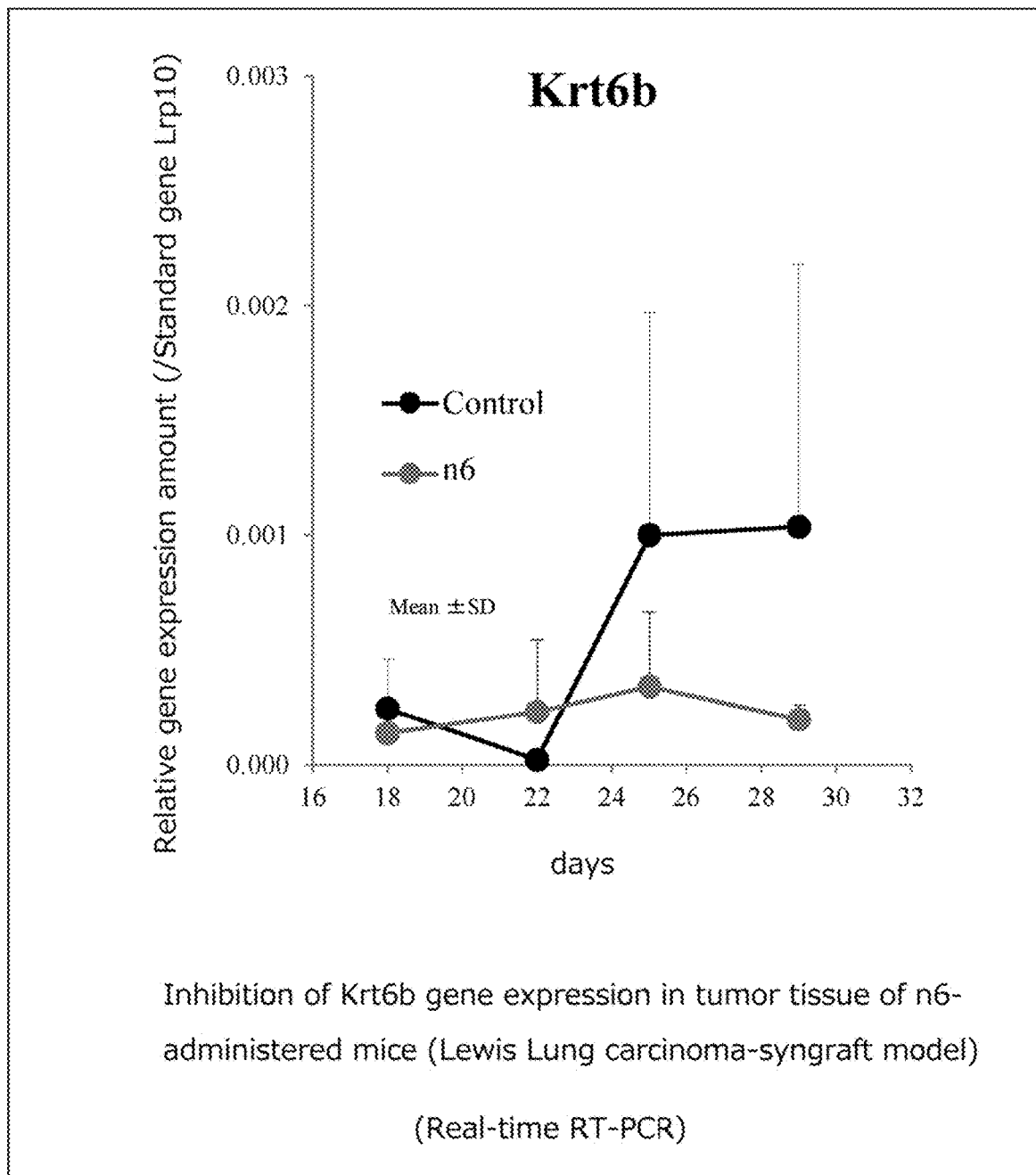
FIG. 24 is a graph representing amount of gene expression of Krt6b gene in tumor tissue of mice in sample material (the sixth fermented liquid) administered group and water for injection administered group.

FIG. 24 shows a result of the test (2). The test (2) is a gene expression analysis in cancer tissue with real-time PCR method. Specifically, among genes for which variation of expression is observed in DNA microarray (ITL-13-MO-049), Krt6b (Keratin 6B) gene-specific primer is designed, and its gene expression is quantitatively analyzed with the real-time PCR method.

In the test (2), Lewis Lung carcinoma cell line, that is an epithelial cancer cell line, was used as a cancer tissue of the Calbio-7-administered mice, and comparative analysis is performed for gene expression of Krt6b as a tumor growth factor, compared with control group to which water for injection was administered. As a result, expression of keratinocyte (keratinized cell) gene group, such as keratin, is observed. That is, the Krt6b is a maker for identifying squamous-cell carcinoma in lung cancer, and inhibition of the expression of the Krt6b gene is observed as shown in FIG. 24.

Summary of the Test Results

For functions of the fermented liquid made from natural material, having an acidity of pH 3 to 4, comprising about 6.5 to 7.5% of colloidal particles having a particle size not exceeding 50 nm and 5 g or more butyric acid per 1000 mL of the fermented liquid according to the present invention to exert effects on living bodies, the fermented liquid may be used as functional foods itself or ram material liquid for functional foods. First summary is that, as apparent from the data of "increased amount and absorption rate", which is a result of the calcium absorption test with the everted gut sac method shown in FIG. 21, and the data of "Gla/Glu-Osteocalcin ratio" and "bone weight and bone strength, and bone density", which are results of the test using osteoporosis-model mice in estrogen deficiency state shown in FIG. 22, the fermented liquid acts on a living body to activate its calcium metabolism and exert significant effects on its bone mineral density and bone strength.

Second summary is that, as apparent from data in FIG. 23 showing increased "*Lactobacillus*" and "*Bifidobacterium*" and decreased "*Clostridium perfringens* (*Welch bacillus*)", the fermented liquid acts on intestinal bacterial flora to double *Lactobacillus* and *Bifidobacterium*, referred as intestinal friendly, or "good" bacteria, and to halve *Clostridium perfringens* (*Welch bacillus*), referred as intestinal unfriendly, or "bad" bacteria. In addition, as shown in FIG. 24, inhibition of Krt6b gene expression in tumor tissue of Calbio-7-administered mice (Lewis Lung carcinoma-syngraft model) is confirmed.

Supplemental Information

Seven species of fermentation bacteria deposited to National Institute of Technology and Evaluation, Patent Microorganisms Depositary (NPMD) (domestically deposited on May 16, 2019, and transferred to the international deposit on Apr. 22, 2020) From the results of partial base sequencing (about 1500 bp) of 16S rDNA (16S rRNA gene) for isolated and cultured fermentation bacteria, used in producing fermented product by Higher Mount Co., Ltd., for identifying the bacteria, it was confirmed that the following bacteria are innocuous to human and animals, and able to be reconstituted from their dried or freeze-dried form.

NITE BP-02945
  Type of microorganism: bacteria
  Cell form: *bacillus*
  Characteristics: spore-forming negative (non-spore-forming)
  Taxonomical position: *Aneurinibacillus* sp.
  Culture condition: standard agar medium
  Culture temperature: 30° C.
  Culture period: 48 hours
  Culture method: aerobic NITE BP-02946
  Type of microorganism: bacteria
  Cell form: *bacillus*
  Characteristics: spore-forming negative (non-spore-forming)
  Taxonomical position: *Brevibacillus* sp.
  Culture condition: standard agar medium
  Culture temperature: 30° C.
  Culture period: 48 hours
  Culture method: aerobic NITE BP-02947
  Type of microorganism: bacteria
  Cell form: *bacillus*

Characteristics: spore-forming negative (non-spore-forming)
Taxonomical position: *Pseudoclavibacter* sp.
Culture condition: standard agar medium
Culture temperature: 30° C.
Culture period: 72 hours
Culture method: aerobic
NITE BP-02948
  Type of microorganism: bacteria
  Cell form: *bacillus*
  Characteristics: spore-forming positive (spore-forming)
  Taxonomical position: *Paenibacillus* sp.
  Culture condition: standard agar medium
  Culture temperature: 30° C.
  Culture period: 72 hours
  Culture method: aerobic
NITE BP-02949
  Type of microorganism: bacteria
  Cell form: *bacillus*
  Characteristics: spore-forming positive (spore-forming)
  Taxonomical position: *Clostridium* sp.
  Culture condition: GAM Broth "Nissui" agar
  Culture temperature: 30° C.
  Culture period: 48 hours
  Culture method: anaerobic
NITE BP-02950
  Type of microorganism: bacteria
  Cell form: *bacillus*
  Characteristics: spore-forming positive (spore-forming)
  Taxonomical position: *Clostridium* sp.
  Culture condition: GAM Broth "Nissui" agar
  Culture temperature: 30° C.
  Culture period: 48 hours
  Culture method: anaerobic
NITE BP-02951
  Type of microorganism: bacteria
  Cell form: *bacillus*
  Characteristics: spore-forming positive (spore-forming)
  Taxonomical position: *Clostridium* sp.
  Culture condition: GAM Broth "Nissui" agar
  Culture temperature: 30° C.
  Culture period: 48 hours
  Culture method: anaerobic

REFERENCE SIGNS LIST 1 fermented liquid having an acidity of pH 3 to 4 comprising colloidal particles having a particle size not exceeding 50 nm and short-chain fatty acids
n1 to n6 first fermented liquid to sixth fermented liquid
pn1 to pn3 first preliminary fermented liquid to third preliminary fermented liquid
w soft water
m fermented medium
m1 to m3 first fermented medium to third fermented medium
ds dried soybeans
fs fermented soybeans
gfs soybean paste
pm2 mixed medium
pfm2 preliminary fermented mixed medium
pm3 honey material
pfm3 preliminary fermented medium
b seed bacterial liquid
b1 fermentation bacteria (International Accession Numbers NITE BP-02945 to NITE BP-0291) contained in the seed bacterial liquid
sp sponge layer
sf1 to sf4 first surface layer to fourth surface layer
dep1 to dep4 first deposition layer to fourth deposition layer
f fermentation stage
f1 to f5 first fermentation line to fifth fermentation line
$p_1 1$ to $p_1 3$ first process to third process of f1
$p_2 1/p_2 2$: first process/second process of f2
$p_3 1/p_3 2$ first process/second process of f3
$p_4 1$ process of f4
$p_5 1$ process of f5
10 fermentation bottle (pottery)
20 first medium tank in f1
30 heating kettle in f1
40 second medium tank in f2
50 third medium tank in f3
100 (two) first fermentation tanks in f1 having a volume of 1000 liter
101 shut-off valve for first fermentation tank, utilizing Pascal's principle and hydrostatic equilibrium
110 extraction unit having a shut-off valve for first fermentation tank
200 second fermentation tank in f1 having a volume of 2000 liter
201 shut-off valve for second fermentation tank, utilizing Pascal's principle and hydrostatic equilibrium
210 extraction unit having a shut-off valve for second fermentation tank
300 third fermentation tank in f2 having a volume of 2000 liter
301 shut-off valve for a third fermentation tank, utilizing Pascal's principle and hydrostatic equilibrium
310 extraction unit having a shut-off valve for a third fermentation tank
320 bag-shaped medium filter in f2
330 circulating pump unit in f2
400 fourth fermentation tank in f3 having a volume of 2000 liter
401 shut-off valve for fourth fermentation tank, utilizing Pascal's principle and hydrostatic equilibrium
410 extraction unit having a shut-off valve for fourth fermentation tank
500 fifth fermentation tank in f4 having a volume of 2000 liter
501 shut-off valve for fifth fermentation tank, utilizing Pascal's principle and hydrostatic equilibrium
510 extraction unit having a shut-off valve for fifth fermentation tank
600 sixth fermentation tank in f5 having a volume of 2000 liter
610 cooling unit in f5
620 reserve tank in f5

The invention claimed is:
1. A method for producing a fermented liquid having an acidity of pH 3 to 4 and comprising colloidal particles having a particle size not exceeding 50 nm and short-chain fatty acids, the short-chain fatty acids comprising butyric acid, propionic acid and lactic acid, the method comprising the steps of:
  preparing:
    a soft water having a pH of 7.0 to 7.6;
    three kinds of fermented media consisting of a first fermented medium having a pH of 4.2 to 4.8 produced from dried, ground soybeans, a second fermented medium having a pH of 4.5 to 5.1 produced from dried, ground plants comprising *Lycium* fruit, jujube and turmeric, and a third fermented medium having a pH of 4.1 to 4.7 produced from a material comprising honey; and a seed bacterial liquid having a pH of 5.0 to 5.6 comprising seven species of fermentation bacteria, International Accession Numbers: NITE BP-02945, NITE BP-02946, NITE BP-02947, NITE BP-02948, NITE BP-02949, NITE BP-02950, and NITE BP-02951, the fermentation bacteria producing organic acids comprising short-chain fatty acids;

performing a Process A comprising the steps of:

putting the soft water, the first fermented medium, and the seed bacterial liquid in a volumetric ratio of 1100 to 1300 L of the soft water, 280 L of the first fermented medium, and 270 to 450 L of the seed bacterial liquid, into a first fermentation tank and mixing them to produce a turbid liquid having a pH of 6.1 to 6.7;

fermenting the turbid liquid at a fermentation temperature of 37° C. to 40° C. for 50 to 100 days to form three layers consisting of a supernatant sponge layer containing fermentation gas, a first deposition layer at a bottom, and an intermediate layer of a translucent fermented liquid having a pH of 5.0 to 5.6 between the sponge layer and the first deposition layer; and extracting the translucent fermented liquid from the three layers to produce a first fermented liquid having a pH of 5.0 to 5.6;

performing a Process B comprising the steps of:

transferring the first fermented liquid having a pH of 5.0 to 5.6 into a second fermentation tank, fermenting the first fermented liquid at a fermentation temperature of 37° C. to 40° C. for 3 to 5 days in a fermentation environment without using any fermented medium to form three layers consisting of a supernatant first surface layer containing fermentation gas bubbles, a second deposition layer at a bottom in which a residue of the first fermented medium is deposited, and an intermediate layer of a translucent fermented liquid having a pH of 4.7 to 5.3 between the first surface layer and the second deposition layer; and extracting the translucent fermented liquid from the three layers to produce a second fermented liquid having a pH of 4.7 to 5.3;

performing a Process C comprising the step of:

transferring the second fermented liquid having a pH of 4.7 to 5.3 into a third fermentation tank;

enclosing the second fermented medium in a bag-shaped filter, suspending the bag-shaped filter inside of the third fermentation tank, and fermenting the second fermented liquid at a fermentation temperature of 37° C. to 40° C. for 8 or 9 days, with circulating the second fermented liquid, to form two layers consisting of a supernatant second surface layer containing fermentation gas bubbles, and a bottom layer of a turbid fermented liquid having a pH of having pH 4.2 to 4.8; and extracting the turbid fermented liquid from the two layers to produce a third fermented liquid having a pH of 4.2 to 4.8;

performing a Process D comprising the steps of:

transferring the third fermented liquid having a pH of 4.2 to 4.8 into a fourth fermentation tank, and mixing the third fermented liquid and the third fermented medium in a volumetric ratio of 20 to 1 to produce a turbid liquid;

fermenting the turbid liquid at a fermentation temperature of 37° C. to 40° C. for 30 to 60 days to form three layers consisting of a supernatant third surface layer, a third deposition layer at a bottom, and an intermediate layer of a translucent fermented liquid having a pH of 3.4 to 4.0 between the third surface layer and the third deposition layer; and extracting the translucent fermented liquid from the three layers to produce a fourth fermented liquid having a pH of 3.4 to 4.0;

performing a Process E comprising the steps of:

transferring the fourth fermented liquid having a pH of 3.4 to 4.0 into a fifth fermentation tank;

fermenting the fourth fermented liquid at a fermentation temperature of 37° C. to 40° C. for 30 to 60 days in a fermentation environment without using any fermented medium to produce a translucent fermented liquid having a pH of 3.3 to 3.9 and a fourth deposition layer; and extracting the translucent fermented liquid to produce a fifth fermented liquid having a pH of 3.3 to 3.9; and performing a Process E comprising the steps of:

transferring the fifth fermented liquid having a pH of 3.3 to 3.9 into a reserve tank of a cooling unit, and rapidly cooling the fifth fermented liquid at the fermentation temperature of 37° C. to 40° C. to 5° C. or lower by the cooling unit;

returning the rapidly cooled fifth fermented liquid to an ordinary temperature condition to produce an ordinary temperature fermented liquid;

fermenting the ordinary temperature fermented liquid at an ordinary temperature for 180 to 240 days to produce a transparent fermented liquid having a pH of 3.0 to 3.6; and extracting the transparent fermented liquid to produce a sixth fermented liquid having a pH of 3.0 to 3.6.

2. The method according to claim 1, wherein the Process A is a Process A' comprising the steps of:

preparing two first fermentation tanks;

putting the soft water, the first fermented medium, and the seed bacterial liquid in a volumetric ratio of 1100 to 1300 L of the soft water, 280 L of the first fermented medium, and 270 to 450 L of the seed bacterial liquid, into each of the two first fermentation tanks equally, and mixing them to produce a turbid liquid having a pH of 6.1 to 6.7;

fermenting the turbid liquid at a fermentation temperature of 37° C. to 40° C. for 50 to 100 days to form three layers consisting of a supernatant sponge layer containing fermentation gas, a first deposition layer at a bottom, and an intermediate layer of a translucent fermented liquid having a pH of 5.0 to 5.6 between the sponge layer and the first deposition layer; and extracting the translucent fermented liquid from the three layers to produce the first fermented liquid having a pH of 5.0 to 5.6; and wherein the Process B is a Process B' comprising the steps of:

transferring each of the first fermented liquids having a pH of 5.0 to 5.6 into one second fermentation tank, and mixing them to produce a first fermented liquid having a uniform acidity;

fermenting the first fermented liquid at a fermentation temperature of 37° C. to 40° C. for 3 to 5 days in a fermentation environment without using any fermented medium to form three layers consisting of a supernatant first surface layer containing fermentation gas bubbles, a second deposition layer at a bottom in which a residue of the first fermented medium is deposited, and an intermediate layer of a translucent fermented liquid having a pH of 4.7 to 5.3 between the first surface layer and the second deposition layer; and extracting the translucent fermented liquid from the three layers to produce the second fermented liquid having a pH of 4.7 to 5.3.

3. The method according to claim 1, wherein the fermented liquid having an acidity of a pH of 3 to 4 comprises 0.5 to 0.6 g of the butyric acid per 100 mL of the fermented liquid.

4. The method according to claim 1, wherein, when an amount of the first fermented liquid formed in the three layers in the first fermentation tank is 1200 L, a process for producing the first fermented medium having a pH of 4.2 to 4.8 comprises the steps of:

soaking and reconstituting the dried soybeans corresponding to 6.5 kg in at least 20 L of the soft water in each of four or more fermentation bottles provided with a lid having valve functionality, and putting 250 g of a sugar chain and 140 cc of the seed bacterial liquid into each of the fermentation bottles;

fermenting the contents of the fermentation bottles at a fermentation temperature of 37° C. to 40° C. for 68 to 74 hours to produce a first preliminary fermented liquid and fermented soybeans, corresponding to 35 L in each fermentation bottle;

removing the fermented soybeans from each of the fermentation bottles, grinding the fermented soybeans into a paste by a grinding means, and mixing the ground soybeans and the first preliminary fermented liquid to produce the first preliminary fermented liquid and a soybean paste, corresponding to 35 L;

transferring the first preliminary fermented liquid and the soybean paste, corresponding to 35 L produced in each fermentation bottle, into a heating kettle, and gradually heating them to 55 to 60° C. to produce the first preliminary fermented liquid and the soybean paste, corresponding to 180 L in total; and transferring the first preliminary fermented liquid and the soybean paste, corresponding to 180 L, from the heating kettle into a first medium tank, while avoiding exposure to external air, wherein the soft water for cooling corresponding to 100 L has been preliminarily put into the first medium tank, and stirring them to produce the first fermented medium corresponding to 280 L.

5. The method according to claim 1, wherein, when the first fermented liquid formed in the three layers in the first fermentation tank is 1200 L, the turbid liquid having a pH of 6.1 to 6.7 produced in the first fermentation tank is a second preliminary fermented liquid having a pH of 6.1 to 6.7 corresponding to 1800 L, produced by putting the first fermented medium having a pH of 4.5 to 5.1 corresponding to 280 L, the seed bacterial liquid having a pH of 5.0 to 5.6 corresponding to 270 to 450 L, and the soft water having a pH of 7.0 to 7.6 corresponding to 1100 to 1300 L into the first fermentation tank and stirring and mixing them.

6. The method according to claim 1, wherein, when the third fermented liquid corresponding to 1050 to 1100 L is produced, a process for producing the second fermented medium having a pH of 4.5 to 5.1 comprises the steps of:

mixing 200 to 210 g of the jujube, 110 to 120 g of the *Lycium* fruit, and 25 to 30 g of the turmeric per 35 L of the second fermented liquid in total to produce a mixed medium;

putting the mixed medium and 35 L of the second fermented liquid into a second medium tank, and fermenting the mixed medium and the second fermented liquid for 2 or 3 days to produce a preliminary fermented mixed medium and a third preliminary fermented liquid having a pH of 4.5 to 5.1; and removing the preliminary fermented mixed medium from the second medium tank, grinding the removed preliminary fermented mixed medium by a grinding means, returning the ground preliminary fermented mixed medium to the second medium tank, and blending the preliminary fermented mixed medium and the third preliminary fermented liquid to produce the second fermented medium having a pH of 4.5 to 5.1 corresponding to 35 L.

7. The method according to claim 1, wherein, when the fourth fermented liquid corresponding to 1000 to 1050 L is produced, a process for producing the third fermented medium comprises the steps of:

putting the material comprising honey corresponding to 3 to 5% of the third fermented liquid into a third medium tank, transferring the third fermented liquid corresponding to four times as much as the material comprising honey into the third medium tank, while avoiding exposure to external air, and stirring them to produce a preliminary fermented medium; and fermenting the preliminary fermented medium at a fermentation temperature of 37° C. to 40° C. for 2 or 3 days to produce the third fermented medium having a pH of 4.1 to 4.7.

* * * * *